(12) United States Patent
Kuramitsu et al.

(10) Patent No.: US 6,939,949 B2
(45) Date of Patent: Sep. 6, 2005

(54) DNA REPAIR ENZYMES, NUCLEIC ACIDS ENCODING DNA REPAIR ENZYMES AND METHODS OF USING THEM

(75) Inventors: Seiki Kuramitsu, Tokyo (JP); Shigeyuki Yokoyama, Kanagawa (JP)

(73) Assignee: Riken, Saitama (JP)

( * ) Notice: Subject to any disclaimer, the term of this patent is extended or adjusted under 35 U.S.C. 154(b) by 255 days.

(21) Appl. No.: 09/938,901

(22) Filed: Aug. 24, 2001

(65) Prior Publication Data

US 2003/0008291 A1 Jan. 9, 2003

(30) Foreign Application Priority Data

Feb. 23, 2001 (JP) ........................................ 2001-047762

(51) Int. Cl.$^7$ ............................. C07K 1/00; C12N 9/00; C12N 9/52; C12N 15/00; C12P 21/06
(52) U.S. Cl. ........................ 530/350; 435/183; 435/220; 435/69.1; 435/320.1
(58) Field of Search ..................... 530/350; 435/69.1, 435/320.1, 183, 220

(56) References Cited

U.S. PATENT DOCUMENTS

| 5,879,899 A | 3/1999 | Li |
| 6,046,036 A | 4/2000 | Kelley et al. |
| 6,252,048 B1 | 6/2001 | Kelley et al. |

OTHER PUBLICATIONS

White et al. Genome Sequence of the Radioresistant bacterium Deinococcus radiodurans R1. Science, vol. 286, 1999, pp 1571–1577.*

* cited by examiner

*Primary Examiner*—Gerry Leffers
*Assistant Examiner*—Maria Marvich
(74) *Attorney, Agent, or Firm*—Fish & Richardson P.C.

(57) ABSTRACT

The invention provides novel DNA repair enzymes, genes encoding the enzymes, and methods of using these polypeptides and nucleic acids, including DNA repair.

3 Claims, 36 Drawing Sheets

```
Tth MutY       1                                         MEAWRKAL LAWYREN-ARP PMR------GE------------KDPYRM VSEM LQQTRVE QALPYYRRFL    53
Hsa MutY      51 CDGLARQPEEVVLQASVSSYHLFRDVAEVTAFRGS LSMY DQE-KRD PWRRRADEMDLD ---------RRAYAMAVSEM LQQTQVATVL NYYTGMM   139
Spo MutY       1       MSDSNHFLDLHSYTQLEVEFRESL IDF DKT-KRI PWRKKECIPPSED SPLEDWEQPVQRLY FM VSEI M QQTRVE TVKRYYTKMM    88
Eco MutY       1                                     MQASQFSAQVL DW DKYGRKT PW D---------ID---------KTPYKM SEVM LQQTQVATVI PYFERFM       56
Eco EndoIII    1                                             MNKAKRLE IL TRLREN--NPHPTT---------ELN----------FSSPFELLI AVLLSAQATDVSNKATAKLY  55

Tth MutY      54 ERFP IT KAL AAAS LE-EVLRW QQ GAGYYR- RAEH HRL ARSVEEL-----PPS FAE LR-GL PGL GPYTAAAVI ASI AFGE RVAAV DGNVRRV SRLFL ARES        145
Hsa MutY     140 QKWP IT QDLI ASIAS LE-EVNQ WAGL GYYS- RGRRL DEGAR KVEEL GGHMPRI TAETI QQL PGVGRYTAGAI ASI AFGQ ATGVV DGNVARV CRVRA GA           237
Spo MutY      89 ETLPL IT KSCAE AE MNTQVMPL WSG MGFYT- RCKRL HQACQHL AKLHPSEIPRI TGDE WAKGI PGWGPYTAGAV GSI AMK QPTGI VQGNVI RML SRAL ALHS       187
Eco MutY      57 ARFP IT MTDL ANAP LD-EVLLH WTGL GYYA- RARNL HKAAQQVATLHGGKFPE IT FEEVA-AL PGVGRSTAGAI BL SLGKHFPIL DGNVKRV LARCY AVSG          153
Eco EndoIII   56 PVANTP AAMLE CGV E-GVKTYIKTI GLYNSK AEN IL KTCR LLEEQHNGEVPEDRAA LF-AL PGV GRKTANVV NIAFGWPTI AVD THI FRVCNRTQF APG        153

Tth MutY     146 -PK----EKE FAI AQG L PEGVDPGV WNQA MELG ATVCL PKRPRCGAQ PLG AFCRG----------KEAPGRYP-----APR--------K                        210
Hsa MutY     238 DPSSTLVSQQ LWGL AQQ L WDP-ARPGDF NQA AMEL GATVC TPQRPLCSQCP VES LCRAQRVEQEQLLASGSL SGSPDVEECAPNTGQCHLCLPPSEPWD                 336
Spo MutY     188 DCSKGKANAL IWKL ANE LVDP-VRPGDF NQA MELG AIT CTPQSPRCSVCP ISE ICKAYQ--EQNVIRDGNTIKYD--IEDVPCN-ICITDIPS-----K                  276
Eco MutY     154 WPGKKEVENK LWSL SEQM IPA-VGVER NQAMMDL GAMI CTRSKPKCSLCP LQN GGIA-----AANNSWALYP------GKK--------P-------K                    225
Eco EndoIII  154 -KN----VEQL EFKLLL KMV PA-EFKVDCH HWL LHGRYTCI ARKPRCGSCTI LE DLCEY-                                                        205

Tth MutY     211 RRAK---------------EER-LVALVLLGRKG----VHLER LEGR ----FQGL MGV PLFPP-EEL P--GRE AFGVRS--------RP----L                          266
Hsa MutY     337 QTLGV---VNFPRKASRKPREESSATCVLEQPGA---LGAQIL VQRPNSG LL-AGLL WEF PSVTW-EPSEQLQRKAL LQELQRWAGP--LPATHLRHL                        425
Spo MutY     277 EDLQNWVARYPVHPAKTKQRE-ERALVVIFQKTDPSTKEKFFL RKRP SAGLL AGL WDF PTI EFGQE SMPKDMDA EFQKSI AQWI SNDSRSLIKKYQSR                     375
Eco MutY     226 PER---TGYFLLLQH-------EDEVL LAQRPPSGL WGGL LYC PQDF AD-EES----LRQWLAQRQ-----IAADNLTQL                                         287
Eco EndoIII  206 --K------EKVD I Tth MutY     267 GE VRHAL THRRLR-----------VEWR-GAL WEGEG DPWKRP-LPKLME VLRKA P------------AH--------AGVVPLPDA                                 325
Hsa MutY     426 GE VHITF SHI KLTYQVYGLALEGQTPVTT VPPGARAL TQEE FHTAAVSTAMKKVF RMV QGQQP STCMGSKRSQVSSP CSRKKPRMGQQVLDNFFRSHI ST DA HSLNSAAQ      535
Spo MutY     376 GRYL HLF SHI RKTSHVFYALAS--PDIV TNEDFFWI SQSD LEHVGMC---ELGL KWV RAAL EIKKRK----VTSLSN------FKEPKL TSA RRIVTKAEC                461
Eco MutY     288 TAFR ITF SHF HLD------------I VP----ML PVSSFTGCMD------EGNAL WYNL AQP PSVG----LAAP VER------LLQQL RTG APV                       350
```

FIG. 5

Tth (Thermus thermophilus HBB), Hsa (Homo sapiens), Spo (Schizosaccharomyces pombe), Eco (Escherichia coli)
Residue essential for N-glycosylase activity  * Residues constituting an iron-sulfur cluster

```
                          Motif I
RecJ_Tt    [73]  KRIRVHGDYDADGLTGTAILVRGLAALG  [100]
RecJ_Ec    [73]  TRIIVVGDFDADGATSTALSVLAMRSLG  [100]
RecJ_Aa    [78]  KRIIIYGDYDVDGITGTAILYRVLKLLG  [105]
RecJ_Hp    [47]  TEILVVGDYDADGVISSAIMAKFFESLN  [74]
RecJ_Hi    [68]  QKIVIVGDFDADGATSTALSVLALRQLG  [95]

PPX1_Sc    [30]  TICVGNESADMDSIASAITYSYCQYIYN  [57]
PRUNE_Dm   [38]  HLVMGNESCDLDSAVSAVTLAFVYAASS  [65]
                   Motif II                         Motif III
RecJ_Tt   [129]  SDLFLTVDCGITNHAELRE  [147]  [153]  VEVIVTPHHTPGK  [165]
RecJ_Ec   [131]  AQLIVTVDNGISSHAGVEH  [149]  [155]  IPVIVTPHHLPGD  [167]
RecJ_Aa   [133]  GDFLIITVDNGTSAVEEIDQ [151]  [154]  LETVVIPHHNVPP  [166]
RecJ_Hp   [102]  APLIITVDNGINAFEAARF  [120]  [126]  YTLIITPHHCLHH  [138]
RecJ_Hi   [126]  VQLLMTVDNGVSSFDGVAF  [144]  [150]  IRVLVTPHHLPPE  [162]

PPX1_Sc   [120]  ELNSYLVDNNDTPKNLKNY  [138]  [141]  NVVGIIDHHFDLQ  [153]
PRUNE_Dm   [88]  PLVCEMWDCRARVALPRRY  [106]  [129]  NVTEILDHRPLED  [141]
                   Motif IV                        Specific Motif
RecJ_Tt   [210]  YADLAAVGTIADVAPLWGW  [228]  [386]  DLLLRYGGHKEAAGFAM  [402]
RecJ_Ec   [226]  LLDLVALGTVADVVPLDAN  [244]  [422]  GMMLKFGGHAMAAGLSL  [438]
RecJ_Aa   [215]  FLDLVALGLLADYMPVNPV  [233]  [404]  DMFLKWGGHDKAMGLTL  [420]
RecJ_Hp   [189]  LLCLAGVATIADMMPLTFF  [207]  [372]  SLLLGYGGHRQACGLSV  [388]
RecJ_Hi   [219]  LLDLVALGTIADVVPLDQN  [237]  [415]  NMILKFGGHAMAAGLSI  [431]

PPX1_Sc   [191]  IALLLMGAILIDTSNMRRK  [209]
PRUNE_Dm  [183]  VAQLLHATIVLDTINFAPA  [201]
```

Tt : Thermus thermophilus HB8, Ec : Escherichia coli, Aa : Aquifex aeolicus,
Hp : Helicobacter pyroli, Hi : Haemophilus influenzae Rd,
Sc : Saccharomyces cerevisiae, Dm : Drosophila melanogaster

UvrB-β

TRCF-β

```
UvrB-β  154 RNLVVERGKPYPREVLLERLLELGYQRNDI  184
TRCF-β   86 WRLLLEVGRAYPREALLSRLLKLGYAR---  113
            *  *  *  ****  **  ***  *** *
               . .                        .

UvrB-β  185 DLSPGRFRAKGEVLEIFPAYETEPIRVELF  215
TRCF-β  114 DED---YRVLGEVVELG------EVRLEFF  148
            *        *  *** *           * * *
                                  . .

UvrB-β  216 GDEVERISQVHPVTG-ERLRELPG------  236
TRCF-β  149 GDELERLVVRGEERRRHVLLPKPGKAEGFT  163
            *** **              *    **
                .

UvrB-β  237 ---FMLFPA  242   *Identical Amino Acid Residues
TRCF-β  164 SKKVLHEPG  172   .Homologous Amino Acid Residues
                    **
                 .
```

DNA REPAIR ENZYMES, NUCLEIC ACIDS ENCODING DNA REPAIR ENZYMES AND METHODS OF USING THEM

CROSS-REFERENCES TO RELATED APPLICATIONS

The present application claims priority under 35 U.S.C. §119 to Japan Patent Application No. 47762/2001, filed Feb. 23, 2001. The aforementioned application is explicitly incorporated herein by reference in its entirety and for all purposes.

TECHNICAL FIELD

The present invention relates to DNA repair enzymes, genes encoding the enzymes, and methods of DNA repair.

BACKGROUND

Genomic DNA in cells in which all the information necessary for the maintenance of life is written is always undergoing damage caused by various exogenous and endogenous factors. As exogenous factors, ultraviolet light, ionizing radiation and environmental chemical substances may be enumerated, for example. As endogenous factors, several types of active oxygen generated from energy metabolism and oxidation stress may be enumerated, for example. Further, mismatches that do not pair correctly with the template can be generated during DNA replication.

When these damaged sites or mismatches are left without repair, bases in the relevant sites will be different from what they are supposed to be, resulting in inaccurate genetic information, i.e., mutations. If a mutation has occurred in a coding region for a protein, the protein may have lower activity (or even no activity) than the corresponding native protein, or the protein may not be produced at all. If a mutation has occurred in a regulatory region, the level of synthesis of the protein under the control of this region can be abnormally increased or decreased. Further, control by other proteins may become ineffective. These changes may cause apoptosis or abnormal growth, e.g., canceration, in relevant cells.

Since damages or mismatches in DNA affect the life of cells per se and may even affect the life of the individuals to which the cells belong, cells have mechanisms to repair DNA damages or mismatches and thereby to maintain genetic information accurately. These are called DNA repair mechanisms. There are several types of DNA repair mechanisms, including base excision repair, photoreactivation, nucleotide excision repair, mismatch repair and recombination repair. It is expected that elucidation of DNA repair mechanisms would provide findings useful for the study of diseases such as cancer and the study of effects of environmental factors on living organisms. Furthermore, certain types of proteins involved in DNA repair mechanisms are expected to increase the accuracy of PCR that has become an important technique in various fields beyond the field of molecular biology.

Genes of a number of DNA repair enzymes have already been cloned from various organisms, and three-dimensional structural analysis of proteins has been carried out for some of them. However, most of these studies performed to date are genetic studies, and biochemical studies have been performed little. In order to elucidate DNA repair mechanisms and obtain findings useful in various fields such as medicine, it is necessary to clone all genes involved in DNA repair and to carry out three-dimensional structural analysis and detailed functional analysis of the encoded proteins.

SUMMARY

The invention provides novel DNA repair enzymes, genes encoding the enzymes and methods of DNA repair. As a result of extensive and intensive research toward the solution of the above problem, the present inventors have succeeded in isolation of genes encoding DNA repair enzymes from a highly thermophilic bacterium.

The present invention provides an isolated protein selected from the group consisting of the following (a) and (b): (a) a protein comprising the amino acid sequence as shown in SEQ ID NO: 2, 4, 6 or 8; (b) a protein which comprises the amino acid sequence as shown in SEQ ID NO: 2, 4, 6 or 8 having a deletion(s), substitution(s) or addition(s) of one or several amino acids and which has DNA repair enzyme activity.

The present invention provides a DNA repair enzyme encoded by a nucleic acid, wherein the nucleic acid hybridizes under stringent conditions with a nucleic acid comprising all or a part of the nucleotide sequence as set forth in SEQ ID NO: 1, 3, 5 or 7, or from a complementary strand thereto.

In alternative aspects, the present invention provides DNA repair enzymes comprising an amino acid sequence which has at least 60%, at least 65%, at least 70%, at least 75%, at least 80%, at least 85%, at least 90%, at least 95%, at least 98%, homology to the amino acid sequence as shown in SEQ ID NO: 2, 4, 6 or 8 and which has DNA repair enzyme. In one aspect, a BLAST algorithm is used to determine the sequence identities, as described, below.

The present invention provides an isolated gene encoding a DNA repair enzyme comprising a DNA encoding the following protein (a) or (b): (a) a protein comprising the amino acid sequence as shown in SEQ ID NO: 2, 4, 6 or 8; (b) a protein which comprises the amino acid sequence as shown in SEQ ID NO: 2, 4, 6 or 8 having a deletion(s), substitution(s) or addition(s) of one or several amino acids and which has DNA repair enzyme activity.

The present invention provides an isolated gene for a DNA repair enzyme comprising the following DNA (c), (d), (e) or (f): (c) a DNA comprising the nucleotide sequence as shown in SEQ ID NO: 1, 3, 5 or 7; (d) a complementary strand to (a); (e) a DNA which hybridizes under stringent conditions either with a DNA consisting of the nucleotide sequence as shown in SEQ ID NO: 1, 3, 5 or 7 or with a complementary strand thereto, and which encodes or is complementary to a DNA which encodes a protein having DNA repair enzyme activity; (f) a DNA which hybridizes under stringent conditions with a probe prepared either from a DNA consisting of the whole or a part of the nucleotide sequence as shown in SEQ ID NO: 1, 3, 5 or 7 or from a complementary strand thereto, and which encodes or is complementary to a DNA which encodes a protein having DNA repair enzyme activity.

The present invention provides recombinant vector comprising the above-described gene. The recombinant vector can be a plasmid, a recombinant virus, a cosmid, an artificial chromosome, and the like.

The present invention provides a cell transformant comprising the above-described recombinant vector. The cell can be a bacterial cell, an insect cell, a plant cell, a mammalian cell, a yeast cell, and the like. The invention also provides a transgenic non-human animal comprising a nucleic acid or a polypeptide of the invention.

The present invention provides method of producing a DNA repair enzyme, comprising culturing the above-described transformant and recovering the DNA repair enzyme from the resultant culture.

The present invention provides a method of repairing DNA sequence errors, comprising carrying out a DNA synthesis reaction in the presence of the above-described protein. The method can be carried out in vitro or in vivo.

The present invention provides a method of preventing erroneous synthesis of DNA sequences, comprising carrying out a DNA synthesis reaction in the presence of the above-described protein.

The present invention provides a repair gene-disrupted (i.e., "knockout") strain obtained by transferring into a host a construct comprising a nucleic acid of the invention; in one aspect, a modified gene has been incorporated into the construct. A marker gene may be given with the modified gene, or, in the same construct as the modified gene. As a specific example of a host is a thermophilic bacterium. In one aspect the thermophilic bacterium is a bacterium of the genus *Thermus*, such as *Thermus thermophilus*.

The proteins of the invention can be stable in a temperatures ranging from about 4° C. to about 100° C. In one aspect, the proteins of the invention are stable up to 98° C., up to 95° C., up to 90° C., up to 80° C., up to 75° C.

The invention also provides arrays (i.e., a "biochip") comprising a nucleic acid as set forth in SEQ ID NO: 1, 3, 5 or 7, and, arrays comprising a nucleic acid of the invention.

The invention provides a method of screening a composition for its ability to specifically bind to a DNA repair enzyme comprising: (a) contacting the a DNA repair enzyme with the composition, wherein the DNA repair enzyme is a polypeptide encoded by a nucleic acid sequence of the invention; and, (b) determining if the composition specifically binds to the DNA repair enzyme.

The invention provides a method for inhibiting the expression of a DNA repair enzyme encoding nucleic acid in a cell, the method comprising the following steps: (a) providing a nucleic acid operably linked to a promoter that expresses an inhibitory sequence, wherein the inhibitory sequence comprises all or part of a nucleic acid sequence of the invention and is expressed in a form sufficient to inhibit expression of a DNA repair enzyme message; and, (b) expressing the inhibitory nucleic acid in an amount sufficient to inhibit the expression of the DNA repair enzyme encoding nucleic acid in the cell. In one aspect, the inhibitory sequence comprises an antisense sequence. In one aspect, the inhibitory sequence comprises a ribozyme sequence.

The invention provides a method of expressing a heterologous nucleic acid sequence in a cell comprising: a) transforming the cell with a heterologous nucleic acid operably linked to a promoter, wherein the heterologous nucleic acid comprises a nucleic acid sequence of the invention; and, b) growing the cell under conditions where the heterologous nucleic acid sequence is expressed in the cell.

The invention provides a method for detecting a nucleic acid in a nucleic acid-containing biological sample, the method comprising the following steps: (a) contacting the sample with a nucleic acid probe comprising a nucleic acid sequence of the invention; (b) hybridizing the nucleic acid probe to the nucleic acid in the sample; and, (c) detecting hybridization of the nucleic acids.

The invention provides a fusion protein comprising a first amino acid sequence as set forth in SEQ ID NO: 2, 4, 6 or 8, or a subsequence thereof, and a second heterologous sequence.

The invention provides an isolated antibody specifically reactive with a polypeptide of the invention or a polypeptide encoded by a nucleic acid of the invention. In one aspect, the antibody is a monoclonal antibody. The invention provides a hybridoma cell comprising a monoclonal antibody of the invention.

The details of one or more aspects of the invention are set forth in the accompanying drawings and the description below. Other features, objects, and advantages of the invention will be apparent from the description and drawings, and from the claims.

All publications, GenBank Accession references (sequences), ATCC Deposits, patents and patent applications cited herein are hereby expressly incorporated by reference for all purposes.

DESCRIPTION OF DRAWINGS

FIG. 5 is an alignment of the amino acid sequence of the MutY of the invention with amino acid sequences of other MutY proteins (Tth MutY—SEQ ID NO:2; Has MutY—SEQ ID NO:20; Spo MutY—SEQ ID NO:21; Eco MutY—SEQ ID NQ:22; and Eco EndoIII—SEQ ID NO:23).

FIG. 14 is an alignment of the amino acid sequence of the RecJ of the invention with amino acid sequences of other RecJ proteins (SEQ ID NOs: 24–56).

FIG. 27 is an alignment of the amino acid sequence of the RecF of the invention with amino acid sequences of other RecF proteins (Tth—SEQ ID NO:58; Eco—SEQ ID NO:59; Ppu—SEQ ID NO:60; Bsu—SEQ ID NO:61; Mtu—SEQ ID NO:62; and Dra—SEQ ID NO:63).

Like reference symbols in the various drawings indicate like elements.

DETAILED DESCRIPTION

Figure 1:
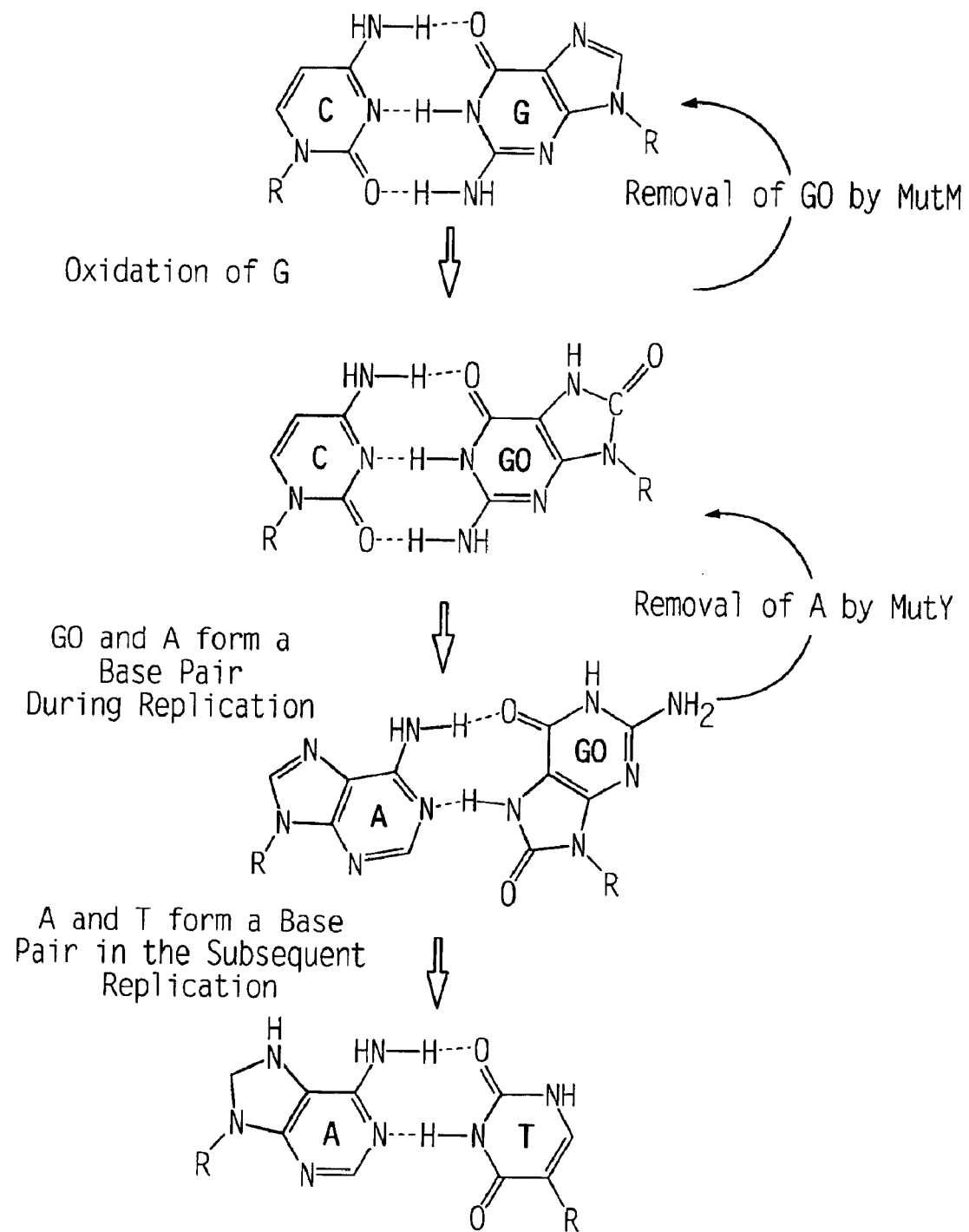
FIG. 1 is a diagram showing the function of MutY.

The invention provides novel DNA repair enzymes and nucleic acids encoding them. As described above, it is important to clone a large number of genes of highly stable DNA repair enzymes derived from highly thermophilic bacteria in order to elucidate DNA repair mechanisms and to obtain findings useful in various fields. The present invention has been achieved using genes of DNA repair enzymes derived from highly thermophilic bacteria belonging to the genus *Thermus*, in particular *Thermus thermophilus*, that are highly thermostable and suitable for three-dimensional structural analysis or molecular function analysis. These enzyme proteins were produced in a large scale and subjected to analysis of substrate recognition mechanism to thereby complete the invention.

One exemplary DNA repair enzyme of the invention is a MutY enzyme, having a molecular weight approximately 31 kDa to 36 kDa, with a sequence as shown in SEQ ID NO: 2. MutY recognizes A:GO mismatches, A:G mismatches and G:GO mismatches, and removes inappropriate bases. See Example section below.

One exemplary DNA repair enzyme of the invention is a RecJ enzyme, having exonuclease activity that degrades single-stranded DNA only in the 5' to 3' direction. It has a molecular weight of approximately 50 kDa, with a sequence as shown in SEQ ID NO: 4. RecJ has specificity to single-stranded DNA, and a Km value of 6.2 $\mu$M. See Example section below.

One exemplary DNA repair enzyme of the invention is a RecF enzyme, having a molecular weight of approximately 37.8 kDa to 22 kDa, with a sequence as shown in SEQ ID NO: 8. RecF prevents replication at damaged sites. Briefly, when damage has occurred in DNA and the reaction of a replication complex stops at that site, a complex of RecF-RecO-RecR proteins binds to the DNA (see Example section below). The Km value is 31 $\mu$M at 37° C. and 32 $\mu$M at 25° C.

One exemplary DNA repair enzyme of the invention is TRCF. TRCF interacts with UvrA and promotes the repair of damage-containing transcribed strands (see Example section below). Nucleotide excision repair mechanism in prokaryotes is also described below. Briefly, the complex UvrAB recognizes a damaged site and binds thereto. Damage in transcribed strands is recognized by TRCF and UvrA. TRCF has a molecular weight of approximately 37.8 kDa, and the theoretical molecular weight of TRCF-β region that is believed to be the binding site for UvrA is approximately 14.4 kDa. TRCF has a sequence as shown in SEQ ID NO: 6.

Definitions

Unless defined otherwise, all technical and scientific terms used herein have the meaning commonly understood by a person skilled in the art to which this invention belongs. As used herein, the following terms have the meanings ascribed to them unless specified otherwise.

The term "nucleic acid" as used herein refers to a deoxyribonucleotide (DNA) or ribonucleotide (RNA) in either single- or double-stranded form. The term encompasses nucleic acids containing known analogues of natural nucleotides. The term encompasses mixed oligonucleotides comprising an RNA portion bearing 2'-O-alkyl substituents conjugated to a DNA portion via a phosphodiester linkage, see, e.g., U.S. Pat. No. 5,013,830. The term also encompasses nucleic-acid-like structures with synthetic backbones. DNA backbone analogues provided by the invention include phosphodiester, phosphorothioate, phosphorodithioate, methylphosphonate, phosphoramidate, alkyl phosphotriester, sulfamate, 3'-thioacetal, methylene (methylimino), 3'-N-carbamate, morpholino carbamate, and peptide nucleic acids (PNAs); see Oligonucleotides and Analogues, a Practical Approach, edited by F. Eckstein, IRL Press at Oxford University Press (1991); Antisense Strategies, Annals of the New York Academy of Sciences, Volume 600, Eds. Baserga and Denhardt (NYAS 1992); Milligan (1993) J. Med. Chem. 36:1923–1937; Antisense Research and Applications (1993, CRC Press). PNAs contain non-ionic backbones, such as N-(2-aminoethyl) glycine units. Phosphorothioate linkages are described, e.g., by U.S. Pat. Nos. 6,031,092; 6,001,982; 5,684,148; see also, WO 97/03211; WO 96/39154; Mata (1997) Toxicol. Appl. Pharmacol. 144:189–197. Other synthetic backbones encompassed by the term include methyl-phosphonate linkages or alternating methylphosphonate and phosphodiester linkages (see, e.g., U.S. Pat. No. 5,962,674; Strauss-Soukup (1997) Biochemistry 36:8692–8698), and benzylphosphonate linkages (see, e.g., U.S. Pat. No. 5,532,226; Samstag (1996) Antisense Nucleic Acid Drug Dev 6:153–156). The term nucleic acid is used interchangeably with gene, DNA, RNA, cDNA, mRNA, oligonucleotide primer, probe and amplification product.

The terms "polypeptide," "protein," and "peptide" include compositions of the invention that also include "analogs," or "conservative variants" and "mimetics" or "peptidomimetics" with structures and activity that substantially correspond to the polypeptide from which the variant was derived, as discussed in detail, below.

The terms "array" or "microarray" or "biochip" or "chip" as used herein is an article of manufacture, a device, comprising a plurality of immobilized target elements, each target element comprising a "cluster" or "biosite" or defined area comprising a nucleic acid molecule or polypeptide of the invention immobilized to a solid surface, as discussed in further detail, below.

Generation and Genetic Engineering of Nucleic Acids

This invention provides novel nucleic acids encoding DNA repair enzymes of the invention, including antisense sequences, expression vectors, probes, PCR primers and the like. As the genes and vectors of the invention can be made and expressed in vitro or in vivo, the invention provides for a variety of means of making and expressing these genes and vectors. One of skill will recognize that desired phenotypes for altering and controlling nucleic acid expression can be obtained by modulating the expression or activity of the genes and nucleic acids (e.g., promoters, enhancers and the like) within the vectors of the invention. Any of the known methods described for increasing or decreasing expression or activity can be used for this invention. The invention can be practiced in conjunction with any method or protocol known in the art, which are well described in the scientific and patent literature.

The nucleic acid sequences of the invention and other nucleic acids used to practice this invention, whether RNA, cDNA, genomic DNA, vectors, viruses or hybrids thereof, may be isolated from a variety of sources, genetically engineered, amplified, and/or expressed recombinantly. Any recombinant expression system can be used, including, in addition to mammalian cells, e.g., bacterial, yeast, insect or plant systems.

Alternatively, these nucleic acids can be synthesized in vitro by well-known chemical synthesis techniques, as described in, e.g., Carruthers (1982) Cold Spring Harbor Symp. Quant. Biol. 47:411–418; Adams (1983) J. Am. Chem. Soc. 105:661; Belousov (1997) Nucleic Acids Res. 25:3440–3444; Frenkel (1995) Free Radic. Biol. Med. 19:373–380; Blommers (1994) Biochemistry 33:7886–7896; Narang (1979) Meth. Enzymol. 68:90; Brown (1979) Meth. Enzymol. 68:109; Beaucage (1981) Tetra. Lett. 22:1859; U.S. Pat. No. 4,458,066. Double stranded DNA fragments may then be obtained either by synthesizing the complementary strand and annealing the strands together under appropriate conditions, or by adding the complementary strand using DNA polymerase with an appropriate primer sequence.

Techniques for the manipulation of nucleic acids, such as, e.g., generating mutations in sequences, subcloning, labeling probes, sequencing, hybridization and the like are well described in the scientific and patent literature, see, e.g., Sambrook, ed., MOLECULAR CLONING: A LABORATORY MANUAL (2ND ED.), Vols. 1–3, Cold Spring Harbor Laboratory, (1989); CURRENT PROTOCOLS IN MOLECULAR BIOLOGY, Ausubel, ed. John Wiley & Sons, Inc., New York (1997); LABORATORY TECHNIQUES IN BIOCHEMISTRY AND MOLECULAR BIOLOGY: HYBRIDIZATION WITH NUCLEIC ACID PROBES, Part I. Theory and Nucleic Acid Preparation, Tijssen, ed. Elsevier, N.Y. (1993).

Nucleic acids, vectors, capsids, polypeptides, and the like can be analyzed and quantified by any of a number of general means well known to those of skill in the art. These include, e.g., analytical biochemical methods such as NMR, spectrophotometry, radiography, electrophoresis, capillary electrophoresis, high performance liquid chromatography (HPLC), thin layer chromatography (TLC), and hyperdiffusion chromatography, various immunological methods, e.g. fluid or gel precipitin reactions, immunodiffusion, immuno-electrophoresis, radioimmunoassays (RIAs), enzyme-linked immunosorbent assays (ELISAs), immuno-fluorescent assays, Southern analysis, Northern analysis, dot-blot analysis, gel electrophoresis (e.g., SDS-PAGE), RT-PCR, quantitative PCR, other nucleic acid or target or signal amplification methods, radiolabeling, scintillation counting, and affinity chromatography.

In addition to "full length" DNA repair enzyme sequences (as determined by identity to the exemplary sequences of the invention, or, by functional criteria, e.g., based on a DNA repair activity, as described in detail in the examples, below), the invention also provides nucleic acid and polypeptides molecules that are only a portion of a "full length" sequence. For example, such a nucleic acid molecule can include a subsequence or fragment which can be used as a probe or primer or a fragment encoding a portion of a DNA repair enzyme domain, e.g., an immunogenic or biologically active portion of a DNA repair enzyme of the invention.

In another aspect, a nucleic acid of the invention includes a nucleotide sequence that includes part, or all, of the coding region and extends into either (or both) the 5' or 3' noncoding region, including both transcribed and non-transcribed sequences. Other embodiments include a fragment that includes a nucleotide sequence encoding an amino acid fragment described herein. Nucleic acid fragments can encode a specific domain or site described herein or fragments thereof.

DNA repair enzyme probes and primers are provided. Typically a probe/primer is an isolated or purified oligonucleotide. The oligonucleotide typically includes a region of nucleotide sequence that hybridizes under stringent conditions (see below) to at least about 7, about 12, about 15, about 20, about 25, about 30, about 35, about 40, about 45, about 50, about 55, about 60, about 65, or about 75 consecutive nucleotides of a sense or antisense sequence of the exemplary sequences described herein. In one embodiment, the nucleic acid is a probe which is at least about 5 or about 10, and less than about 200 or less than 100 or less than 50 base pairs in length. In various embodiment, the probe or primer can be identical, or differ by 1, or less than about 5 or about 10 bases, from an exemplary sequence of the invention (while still capable of hybridizing under stringent conditions). If alignment is needed for this comparison the sequences can be aligned for maximum homology. "Looped" out sequences from deletions or insertions, or mismatches, are considered differences.

Amplification of Nucleic Acids

The invention provides oligonucleotide primers that can amplify DNA repair enzyme nucleic acids of the invention. The term "amplifying" and "amplification" as used herein incorporates its common usage and refers to the use of any suitable amplification methodology for generating or detecting recombinant or naturally expressed nucleic acid. For example, the invention provides methods and reagents (e.g., specific degenerate oligonucleotide primer pairs) for amplifying (e.g., by polymerase chain reaction, PCR) naturally expressed (e.g., genomic or mRNA) or recombinant (e.g., cDNA) nucleic acids of the invention in vivo or in vitro.

The nucleic acids of the invention can also be cloned or measured quantitatively using amplification techniques. Using the exemplary degenerate primer pair sequences of the invention (see below), the skilled artisan can select and design suitable oligonucleotide amplification primers. Amplification methods are also well known in the art, and include, e.g., polymerase chain reaction, PCR (PCR PROTOCOLS, A GUIDE TO METHODS AND APPLICATIONS, ed. Innis, Academic Press, N.Y. (1990) and PCR STRATEGIES (1995), ed. Innis, Academic Press, Inc., N.Y., ligase chain reaction (LCR) (see, e.g., Wu (1989) Genomics 4:560; Landegren (1988) Science 241:1077; Barringer (1990) Gene 89:117); transcription amplification (see, e.g., Kwoh (1989) Proc. Natl. Acad. Sci. USA 86:1173); and, self-sustained sequence replication (see, e.g., Guatelli (1990) Proc. Natl. Acad. Sci. USA 87:1874); Q Beta replicase amplification (see, e.g., Smith (1997) J. Clin. Microbiol. 35:1477–1491), automated Q-beta replicase amplification assay (see, e.g., Burg (1996) Mol. Cell. Probes 10:257–271) and other RNA polymerase mediated techniques (e.g., NASBA, Cangene, Mississauga, Ontario); see also Berger (1987) Methods Enzymol. 152:307–316; Sambrook; Ausubel; U.S. Pat. Nos. 4,683,195 and 4,683,202; Sooknanan (1995) Biotechnology 13:563–564.

Once amplified, the libraries can be cloned, if desired, into any of a variety of vectors using routine molecular biological methods; methods for cloning in vitro amplified nucleic acids are described, e.g., U.S. Pat. No. 5,426,039. To facilitate cloning of amplified sequences, restriction enzyme sites can be "built into" the PCR primer pair. The primers can encode amino acid residues that are conservative substitutions (e.g., hydrophobic for hydrophobic residue) or functionally benign substitutions (e.g., retaining DNA repair activity).

Paradigms to design degenerate primer pairs are well known in the art. For example, a COnsensus-DEgenerate Hybrid Oligonucleotide Primer (CODEHOP) strategy computer program can be directly linked from the BlockMaker™ multiple sequence alignment site for hybrid primer prediction beginning with a set of related protein sequences. Means to synthesize oligonucleotide primer pairs are well known in the art. "Natural" base pairs or synthetic base pairs can be used. For example, use of artificial nucleobases offers a versatile approach to manipulate primer sequence and generate a more complex mixture of amplification products. Various families of artificial nucleobases are capable of assuming multiple hydrogen bonding orientations through internal bond rotations to provide a means for degenerate molecular recognition. Incorporation of these analogs into a single position of a PCR primer allows for generation of a complex library of amplification products. See, e.g., Hoops (1997) Nucleic Acids Res. 25:4866–4871. Nonpolar molecules can also be used to mimic the shape of natural DNA bases. A non-hydrogen-bonding shape mimic for adenine can replicate efficiently and selectively against a nonpolar shape mimic for thymine (see, e.g., Morales (1998) Nat. Struct. Biol. 5:950–954).

The invention provides sets of amplification primers capable of amplifying all or a portion of any DNA repair enzyme nucleic acid sequence of the invention, particularly, the exemplary sequence described herein. Thus, in one embodiment a set (pair) of primers is provided, e.g., primers suitable for use in a PCR, which can be used to amplify a selected region of a DNA repair enzyme sequence. In various embodiment, the primers can be at least about 5, about 10, or about 50 base pairs in length and can be less than about 100, or less than about 200, base pairs in length. The primers can be identical, or differ by one or more base residues from an exemplary sequence of the invention.

Generating Nucleic Acids from Cells

The invention provides method for generating nucleic acids that encode DNA repair enzymes by, e.g., amplification (e.g., PCR) of appropriate nucleic acid sequences using degenerate primer pairs, or traditional cloning using cDNA or genomic libraries, or, phage display libraries, or the like.

Genetic Engineering of DNA Repair Enzyme-Encoding Sequences

The nucleic acid sequences of the invention can be operably linked to transcriptional or translational control elements, e.g., transcription and translation initiation sequences, promoters and enhancers, transcription and translation terminators, polyadenylation sequences, and other sequences useful for transcribing DNA into RNA. In construction of recombinant expression cassettes, vectors, transgenics, of the invention, a promoter fragment can be employed to direct expression of the desired nucleic acid in all tissues. Transcriptional or translational control elements can be isolated from natural sources, obtained from such sources as ATCC or GenBank libraries, or prepared by synthetic or recombinant methods.

The term "expression vector" refers to any recombinant expression system for the purpose of expressing a nucleic acid sequence of the invention in vitro or in vivo, constitutively or inducibly, in any cell, including prokaryotic, yeast, fungal, plant, insect or mammalian cell. The term includes linear or circular expression systems. The term includes expression systems that remain episomal or integrate into the host cell genome. The expression systems can have the ability to self-replicate or not, i.e., drive only transient expression in a cell. The term includes recombinant expression "cassettes" which contain only the minimum elements needed for transcription of the recombinant nucleic acid.

The invention also provides fusion proteins comprising the polypeptides of the invention and heterologous domains, e.g., for protein detection, purification, or other applications. Detection and purification facilitating domains include, e.g., metal chelating peptides such as polyhistidine tracts or histidine- tryptophan modules or other domains that allow purification on immobilized metals; maltose binding protein; protein A domains that allow purification on immobilized immunoglobulin; or the domain utilized in the FLAGS extension/affinity purification system (Immunex Corp, Seattle Wash.).

The inclusion of a cleavable linker sequences such as Factor Xa (see, e.g., Ottavi (1998) Biochimie 80:289–293), subtilisin protease recognition motif (see, e.g., Polyak (1997) Protein Eng. 10:615–619); enterokinase (Invitrogen, San Diego Calif.), and the like, can be useful to facilitate purification. For example, one construct can include a polypeptide-encoding nucleic acid sequence linked to six histidine residues followed by a thioredoxin, an enterokinase cleavage site (see, e.g., Williams (1995) Biochemistry 34:1787–1797), and an amino terminal translocation domain. The histidine residues facilitate detection and purification while the enterokinase cleavage site provides a means for purifying the desired protein(s) from the remainder of the fusion protein. Technology pertaining to vectors encoding fusion proteins and application of fusion proteins are well described in the scientific and patent literature, see e.g., Kroll (1993) DNA Cell. Biol., 12:441–53.

Cloning and Construction of Expression Vectors

The invention provides expression vectors comprising the DNA repair enzyme nucleic acid sequences of the invention. These nucleic acids may be introduced into a genome or into the cytoplasm or a nucleus of a cell and expressed by a variety of conventional techniques, well described in the scientific and patent literature. See, e.g., Roberts (1987) Nature 328:731; Schneider (1995) Protein Expr. Purif. 6435:10; Sambrook, Tijssen or Ausubel. Product information from manufacturers of biological reagents and experimental equipment also provide information regarding known biological methods. The vectors can be isolated from natural sources, obtained from such sources as ATCC or GenBank libraries, or prepared by synthetic or recombinant methods.

The nucleic acids of the invention can be expressed in expression cassettes, vectors or viruses which are stably or transiently expressed in cells (e.g., episomal expression systems). Selection markers can be incorporated into expression cassettes and vectors to confer a selectable phenotype on transformed cells and sequences. For example, selection markers can code for episomal maintenance and replication such that integration into the host genome is not required. For example, the marker may encode antibiotic resistance (e.g., chloramphenicol, kanamycin, G418, bleomycin, hygromycin) to permit selection of those cells transformed with the desired DNA sequences.

Inhibitory Sequences

The invention further provides for nucleic acids complementary to, i.e., antisense sequences to, the DNA repair enzyme sequences of the invention. Antisense sequences are capable of inhibiting the transport, splicing or transcription of DNA repair enzyme-encoding genes. The inhibition can be effected through the targeting of genomic DNA or messenger RNA. The transcription or function of targeted nucleic acid can be inhibited, e.g., by hybridization and/or cleavage. One particularly useful set of inhibitors provided by the present invention includes oligonucleotides that are able to either bind DNA repair enzyme gene or message, in either case preventing or inhibiting the production or function of DNA repair enzymes. The association can be though sequence specific hybridization. Such inhibitory nucleic acid sequences can, e.g., be used to completely inhibit or depress the ability of DNA repair enzymes to repair DNA. Another useful class of inhibitors includes oligonucleotides that cause inactivation or cleavage of message. The oligonucleotide can have enzyme activity that causes such cleavage, such as ribozymes. The oligonucleotide can be chemically modified or conjugated to an enzyme or composition capable of cleaving the complementary nucleic acid. One may screen a pool of many different such oligonucleotides for those with the desired activity.

The invention provides for with antisense oligonucleotides capable of binding message that can inhibit DNA repair enzyme activity by targeting mRNA. Strategies for designing antisense oligonucleotides are well described in the scientific and patent literature, and the skilled artisan can design such oligonucleotides using the novel reagents of the invention. In some situations, naturally occurring nucleic acids used as antisense oligonucleotides may need to be relatively long (18 to 40 nucleotides) and present at high concentrations. A wide variety of synthetic, non-naturally occurring nucleotide and nucleic acid analogues are known which can address this potential problem. For example, peptide nucleic acids (PNAs) containing non-ionic backbones, such as N-(2-aminoethyl) glycine units can be used. Antisense oligonucleotides having phosphorothioate linkages can also be used, as described in WO 97/03211; WO 96/39154; Mata (1997) *Toxicol Appl Pharmacol* 144:189–197; Antisense Therapeutics, ed. Agrawal (Humana Press, Totowa, N.J., 1996). Antisense oligonucleotides having synthetic DNA backbone analogues provided by the invention can also include phosphoro-dithioate, methylphosphonate, phosphoramidate, alkyl phosphotriester, sulfamate, 3'-thioacetal, methylene (methylimino), 3'-N-carbamate, and morpholino carbamate nucleic acids, as described herein.

Combinatorial chemistry methodology can be used to create vast numbers of oligonucleotides that can be rapidly screened for specific oligonucleotides that have appropriate binding affinities and specificities toward any target, such as the sense and antisense DNA repair enzyme sequences of the invention (for general background information, see, e.g., Gold (1995) *J. of Biol. Chem.* 270:13581–13584). Combinatorial chemistry methodology can also be used to screen for agonist or antagonist ligands for DNA repair enzymes.

In yet another embodiment, the antisense nucleic acid molecule of the invention can be α-anomeric nucleic acid molecule. An α-anomeric nucleic acid molecule forms specific double-stranded hybrids with complementary RNA in which, contrary to the usual β-units, the strands run parallel to each other (Gaultier et al. (1987) *Nucleic Acids. Res.* 15:6625–6641). The antisense nucleic acid molecule can also comprise a 2'-o-methylribonucleotide (Inoue et al. (1987) *Nucleic Acids Res.* 15:6131–6148) or a chimeric RNA-DNA analogue (Inoue et al. (1987) *FEBS Lett.* 215:327–330).

The invention provides for with ribozymes capable of binding DNA repair enzyme message which can inhibit DNA repair enzyme activity by targeting mRNA. Strategies for designing ribozymes and selecting the DNA repair enzyme-specific antisense sequence for targeting are well described in the scientific and patent literature, and the skilled artisan can design such ribozymes using the novel reagents of the invention. Ribozymes act by binding to a target RNA through the target RNA binding portion of a ribozyme which is held in close proximity to an enzymatic portion of the RNA that cleaves the target RNA. Thus, the ribozyme recognizes and binds a target RNA through complementary base-pairing, and once bound to the correct site, acts enzymatically to cleave and inactivate the target RNA. Cleavage of a target RNA in such a manner will destroy its ability to direct synthesis of an encoded protein if the cleavage occurs in the coding sequence.

The enzymatic ribozyme RNA molecule can be formed in a hammerhead motif, but may also be formed in the motif of a hairpin, hepatitis delta virus, group I intron or RNaseP-like RNA (in association with an RNA guide sequence). Examples of such hammerhead motifs are described by Rossi (1992) *Aids Research and Human Retroviruses* 8:183; hairpin motifs by Hampel (1989) *Biochemistry* 28:4929, and Hampel (1990) *Nuc. Acids Res.* 18:299; the hepatitis delta virus motif by Perrotta (1992) *Biochemistry* 31:16; the RNaseP motif by Guerrier-Takada (1983) *Cell* 35:849; and the group I intron by Cech U.S. Pat. No. 4,987,071. The recitation of these specific motifs is not intended to be limiting; those skilled in the art will recognize that an enzymatic RNA molecule of this invention has a specific substrate binding site complementary to one or more of the target gene RNA regions, and has nucleotide sequence within or surrounding that substrate binding site which imparts an RNA cleaving activity to the molecule.

The inhibitory (e.g., antisense) nucleic acid molecules of the invention are typically administered to a subject (e.g., by direct injection at a tissue site), or generated in situ such that they hybridize with or bind to cellular mRNA and/or genomic DNA encoding a DNA repair enzyme to thereby inhibit expression of the protein, e.g., by inhibiting transcription and/or translation. Alternatively, inhibitory nucleic acid molecules can be modified to target selected cells and then administered systemically. For systemic administration, inhibitory molecules can be conjugated with carriers that specifically bind to a receptor or an antigen expressed on a selected cell surface, e.g., by linking the inhibitory nucleic acid molecules to peptides or antibodies that bind to DNA repair enzymes or antigens. This linking can be direct or indirect, e.g., as by using liposomes. The inhibitory nucleic acid molecules can also be delivered to cells using the vectors such as viruses. To achieve sufficient intracellular concentrations of the inhibitory molecules, vector constructs in which the inhibitory nucleic acid molecule is placed under the control of a strong constitutive or inducible promoter, e.g., a pol II or a pol III promoter.

In other embodiments, a nucleic acid of the invention can also include other appended groups such as peptides (e.g., for targeting host cells in vivo), or agents facilitating transport across the cell membrane (see, e.g., Letsinger et al. (1989) *Proc. Natl. Acad. Sci. USA* 86:6553–6556; Lemaitre et al. (1987) *Proc. Natl. Acad. Sci. USA* 84:648–652; PCT Publication No. WO88/09810) or the blood-brain barrier (see, e.g., PCT Publication No. WO89/10134). In addition, nucleic acids (e.g., oligonucleotides) can be modified with hybridization-triggered cleavage agents (See, e.g., Krol (1988) *Bio-Techniques* 6:958–976) or intercalating agents. (See, e.g., Zon (1988) *Pharm. Res.* 5:539–549). To this end, the oligonucleotide may be conjugated to another molecule, (e.g., a peptide, hybridization triggered cross-linking agent, transport agent, or hybridization-triggered cleavage agent).

Transformed Bacterium, Transgenic and "Knockout" Cells and Organisms

The invention provides non-human transgenic (i.e., transformed) bacteria, animals and plants comprising the DNA repair enzyme nucleic acids of the invention or DNA repair enzyme "knockout" bacterial and animals generated using the nucleic acids of the invention. Such bacteria and animals are useful for studying the function and/or activity of DNA repair enzymes and for identifying and/or evaluating natural ligand, second messengers, modulators and other ligands of DNA repair enzyme activity. As used herein, a "transgenic animal" is a non-human animal, e.g., a mammal or a rodent, such as a rat or mouse, in which one or more of the cells of the animal includes a transgene (or is a "knockout"). Other examples of transgenic animals include non-human primates, sheep, dogs, cows, goats, chickens, amphibians, and the like. A transgene as used herein includes, e.g., exogenous DNA or a rearrangement, e.g., a deletion of endogenous chromosomal DNA, which preferably is integrated into or occurs in the genome of the cells of a transgenic bacteria or animal. A transgene can direct the expression of an encoded gene product in one cell (e.g., in a bacterium), or cells or tissues of a transgenic animal, other transgenes, e.g., a knockout, to reduce expression. Thus, a transgenic bacteria or animal can be one in which an endogenous DNA repair enzyme gene has been altered by, e.g., by homologous recombination between the endogenous gene and an exogenous DNA molecule introduced into a cell, e.g., a bacterium or, an embryonic cell of an animal, prior to development of the animal.

DNA Repair Enzymes

The invention provides DNA repair enzymes, peptides, and fusion protein comprising these proteins, or subsequences thereof. An "isolated" or "purified" polypeptide or protein is substantially free of cellular material or other contaminating proteins from the cell or tissue source from which the protein is derived, or substantially free from chemical precursors or other chemicals when chemically synthesized. In one embodiment, the language "substantially free" means preparation of DNA repair enzyme having less than about 30%, 20%, 10% and more preferably 5% (by dry weight), of non- DNA repair enzyme. When DNA repair enzymes or biologically active portions thereof are recombinantly produced, they can be prepared to be substantially free of culture medium, i.e., culture medium represents less than about 20%, or less than about 10%, or less than about 5% of the volume of the protein preparation. In alternative embodiments, the invention provides isolated or purified preparations of at least 0.01, 0.1, 1.0, and 10 milligrams in dry weight.

The invention provides DNA repair enzymes with non-essential amino acid residue substitutions. A "non-essential" amino acid residue is a residue that can be altered from the exemplary DNA repair enzyme sequences provided herein without abolishing or without substantially altering a binding or biological activity, whereas an "essential" amino acid residue results in such a change.

The invention provides DNA repair enzymes with conservative amino acid substitutions. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted nonessential amino acid residue in a DNA repair enzyme can be replaced with another amino acid residue from the same side chain family. Alternatively, in another embodiment, mutations can be introduced randomly along all or part of a DNA repair enzyme coding sequence, such as by saturation mutagenesis, and the resultant mutants can be screened for DNA repair biological activity to identify mutants that retain activity. An alternative exemplary guideline uses the following six groups, each containing amino acids that are conservative substitutions for one another: 1) Alanine (A), Serine (S), Threonine (T); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); and 6) Phenylalanine (F), Tyrosine (Y), Tryptophan (W); (see also, e.g., Creighton (1984) Proteins, W. H. Freeman and Company; Schulz and Schimer (1979) Principles of Protein Structure, Springer-Verlag). One of skill in the art will appreciate that the above-identified substitutions are not the only possible conservative substitutions. For example, for some purposes, one may regard all charged amino acids as conservative substitutions for each other whether they are positive or negative. In addition, individual substitutions, deletions or additions that alter, add or delete a single amino acid or a small percentage of amino acids in an encoded sequence can also be considered "conservatively modified variations."

The invention also provides mimetic and peptidomimetic DNA repair enzymes. The terms "mimetic" and "peptidomimetic" refer to a synthetic chemical compound that has substantially the same structural and/or functional characteristics of enzymes, e.g., DNA repair. The mimetic can be either entirely composed of synthetic, non-natural analogues of amino acids, or, is a chimeric molecule of partly natural peptide amino acids and partly non-natural analogs of amino acids. The mimetic can also incorporate any amount of natural amino acid conservative substitutions as long as such substitutions also do not substantially alter the mimetic's structure and/or activity. As with polypeptides of the invention which are conservative variants, routine experimentation will determine whether a mimetic is within the scope of the invention, i.e., that its structure and/or function is not substantially altered. Polypeptide mimetic compositions can contain any combination of non-natural structural components, which are typically from three structural groups: a) residue linkage groups other than the natural amide bond ("peptide bond") linkages; b) non-natural residues in place of naturally occurring amino acid residues; or c) residues which induce secondary structural mimicry, i.e., to induce or stabilize a secondary structure, e.g., a beta turn, gamma turn, beta sheet, alpha helix conformation, and the like. A polypeptide can be characterized as a mimetic when all or some of its residues are joined by chemical means other than natural peptide bonds. Individual peptidomimetic residues can be joined by peptide bonds, other chemical bonds or coupling means, such as, e.g., glutaraldehyde, N-hydroxysuccinimide esters, bifunctional maleimides, N,N'-dicyclohexylcarbodiimide (DCC) or N,N'-diisopropylcarbodiimide (DIC). Linking groups that can be an alternative to the traditional amide bond ("peptide bond") linkages include, e.g., ketomethylene (e.g., —C(=O)—CH$_2$— for —C(=O)—NH—), aminomethylene (CH$_2$—NH), ethylene, olefin (CH=CH), ether (CH$_2$—O), thioether (CH$_2$—S), tetrazole (CN$_4$—), thiazole, retroamide, thioamide, or ester (see, e.g., Spatola (1983) in Chemistry and Biochemistry of Amino Acids, Peptides and Proteins, Vol. 7, pp 267–357, "Peptide Backbone Modifications," Marcell Dekker, N.Y.). A polypeptide can also be characterized as a mimetic by containing all or some non-natural residues in place of naturally occurring amino acid residues; non-natural residues are well described in the scientific and patent literature.

The invention provides polypeptides that are less than "full length" such that they only comprise a ligand domain for purposes of screening studies, directed mutagenesis, biological studies, as immunogens, for fusion proteins, and the like. As used herein, a "biologically active portion" of a DNA repair enzyme includes a fragment of a DNA repair enzyme that participates in a DNA repair activity. Biologically active portions of DNA repair enzymes include peptides comprising amino acid sequences sufficiently homologous to or derived from the amino acid sequence of an exemplary DNA repair enzymes of the invention. These peptides can include less amino acids than "full length" DNA repair enzymes, and can exhibit at least one activity (e.g., DNA binding or biological activity or immunogenic property) of a "full length" DNA repair enzyme. Typically, biologically active portions comprise a complete domain or motif with at least one activity of the DNA repair enzyme, e.g., specific binding to a DNA base pair mismatch. A biologically active portion of a DNA repair enzyme can be a polypeptide that is, e.g., 10, 25, 50, 100, 200 or more amino acids in length. Biologically active portions of a DNA repair enzymes can be used as targets for developing agents which modulate a DNA repair enzyme mediated activity.

Fusion proteins of the invention can also include all or a part of a serum protein, e.g., an IgG constant region, or human serum albumin. The fusion proteins of the invention can be incorporated into pharmaceutical compositions and administered to a subject in vivo. These fusion proteins can be used to affect the bioavailability of a DNA repair enzyme substrate or pharmaceutical composition. Fusion proteins as pharmaceutical compositions can be useful therapeutically for the treatment of disorders caused by, for example, (i) aberrant modification or mutation of a gene encoding a DNA repair enzyme; (ii) mis-regulation of a DNA repair enzyme gene of the invention; and (iii) aberrant post-translational modification of a DNA repair enzyme.

Sequence Homology Determinations

The invention provides several subfamilies, or genuses, of nucleic acids and DNA repair enzymes (as set forth by the exemplary sequences of the invention, and as described in detail herein), members of which are determined to be within the scope of the invention by calculations of their homology, or sequence identity, to the exemplary sequences of the invention. To determine the percent identity of two amino acid sequences, or of two nucleic acid sequences (to determine if they are within the scope of the invention), the sequences are aligned for optimal comparison purposes (e.g., gaps can be introduced in one or both of a first and a second amino acid or nucleic acid sequence for optimal alignment and non-homologous sequences can be disregarded for comparison purposes). In one embodiment, the length of a reference sequence aligned for comparison purposes is at least 30%, or at least 40%, or at least 50%, or at least 60%, or at least 70%, 80%, 90%, or 100% of the length of the reference sequence (e.g., when aligning a second sequence to exemplary DNA repair enzyme amino acid sequences. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In one embodiment, the percent identity between two amino acid sequences is determined using the algorithm described in Needleman (1970) J. Mol. Biol. (48):444–453, and variations thereof; this algorithm has been incorporated into the GAP program in the GCG software package (available at http://www.gcg.com), using either a Blossum 62 matrix or a PAM250 matrix, and a gap weight of 16, 14, 12, 10, 8, 6, or 4 and a length weight of 1, 2, 3, 4, 5, or 6. In yet another embodiment, the percent identity between two nucleotide sequences is determined using the GAP program in the GCG software package (available at http://www.gcg.com), using a NWSgapdna.CMP matrix and a gap weight of 40, 50, 60, 70, or 80 and a length weight of 1, 2, 3, 4, 5, or 6.

The percent identity between two amino acid or nucleotide sequences also can be determined using the algorithm of E. Meyers and W. Miller (CABIOS, 4:11–17 (1989)) which has been incorporated into the ALIGN program (version 2.0), using a PAM120 weight residue table, a gap length penalty of 12 and a gap penalty of 4.

The nucleic acid and protein sequences described herein can be used as a "query sequence" to perform a search against public databases to, e.g., to identify other DNA repair enzyme family members. Such searches can be performed using the NBLAST and XBLAST programs (version 2.0) of Altschul, et al. (1990) J. Mol. Biol. 215:403-10. BLAST nucleotide searches can be performed with the NBLAST program, score =100, wordlength=12 to obtain nucleotide sequences homologous to nucleic acid molecules of the invention. BLAST protein searches can be performed with the XBLAST program, score=50, wordlength=3 to obtain amino acid sequences homologous to DNA repair enzyme molecules of the invention. To obtain gapped alignments for comparison purposes, Gapped BLAST can be utilized as described in Altschul et al., (1997) *Nucleic Acids Res.* 25(17):3389–3402. When utilizing BLAST and Gapped BLAST programs, the default parameters of the respective programs (e.g., XBLAST and NBLAST) can be used. See http://www.ncbi.nlm.nih.gov.

Stringent Hybridization Methods

Nucleic acids with the scope of the invention can also be determined by their ability to hybridize to an exemplary nucleic acid of the invention by stringent hybridization. The phrase "stringent conditions" refers to hybridization or wash conditions under which a nucleic acid, e.g., a sample nucleic acid or a probe will primarily hybridize to its target subsequence, typically in a complex mixture of nucleic acid, but to no other sequences in significant amounts. A positive signal (e.g., identification of a nucleic acid of the invention) is about 10 times background hybridization. Stringent conditions are sequence-dependent and will be different in different circumstances. Longer sequences hybridize specifically at higher temperatures. An extensive guide to the hybridization of nucleic acids is found in Tijssen, Techniques in Biochemistry and Molecular Biology—Hybridization with Nucleic Probes, "Overview of principles of hybridization and the strategy of nucleic acid assays" (1993). Generally, stringent conditions are selected to be about 5–10° C. lower than the thermal melting point (Tm) for the specific sequence at a defined ionic strength and pH. The Tm is the temperature (under defined ionic strength, pH, and nucleic acid concentration) at which 50% of the probes complementary to the target hybridize to the target sequence at equilibrium (as the target sequences are present in excess, at Tm, 50% of the probes are occupied at equilibrium).

Stringent conditions will be those in which the salt concentration is less than about 1.0 M sodium ion, typically about 0.01 to 1.0 M sodium ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide.

Stringent hybridization conditions that can be used to identify nucleic acids within the scope of the invention can include hybridization in a buffer comprising 50% formamide, 5×SSC, and 1% SDS at 42° C., or hybridization in a buffer comprising 5×SSC and 1% SDS at 65° C., both with a wash of 0.2×SSC and 0.1% SDS at 65° C. Exemplary stringent hybridization conditions can also include a hybridization in a buffer of 40% formamide, 1 M NaCl, and 1% SDS at 37° C., and a wash in 1×SSC at 45° C. Alternatively, hybridization to filter-bound DNA in 0.5 M NaHPO$_4$, 7% sodium dodecyl sulfate (SDS), 1 mM EDTA at 65° C., and washing in 0.1×SSC/0.1% SDS at 68° C. can be used to identify and isolate nucleic acids within the scope of the invention. Those of ordinary skill will readily recognize that alternative but comparable hybridization and wash conditions can be utilized to provide conditions of similar stringency.

However, the selection of a hybridization format is not critical, as is known in the art, it is the stringency of the wash conditions that set forth the conditions which determine whether a nucleic acid is within the scope of the invention. Wash conditions used to identify nucleic acids within the scope of the invention include, e.g.: a salt concentration of about 0.02 molar at pH 7 and a temperature of at least about 50° C. or about 55° C. to about 60° C.; or, a salt concentration of about 0.15 M NaCl at 72° C. for about 15 minutes; or, a salt concentration of about 0.2×SSC at a temperature of at least about 50° C. or about 55° C. to about 60° C. for about 15 to about 20 minutes; or, the hybridization complex is washed twice with a solution with a salt concentration of about 2×SSC containing 0.1% SDS at room temperature for 15 minutes and then washed twice by 0.1×SSC containing 0.1% SDS at 68° C. for 15 minutes; or, equivalent conditions. Stringent conditions for washing can also be 0.2×SSC/ 0.1% SDS at 42° C. In instances wherein the nucleic acid molecules are deoxyoligonucleotides ("oligos"), stringent conditions can include washing in 6×SSC/0.05% sodium pyrophosphate at 37° C. (for 14 base oligos), 48° C. (for 17-base oligos), 55° C. (for 20-base oligos), and 60° C. (for 23-base oligos). See Sambrook, ed., MOLECULAR CLONING: A LABORATORY MANUAL (2ND ED.), Vols. 1–3, Cold Spring Harbor Laboratory, (1989); CURRENT PROTOCOLS IN MOLECULAR BIOLOGY, Ausubel, ed. John Wiley & Sons, Inc., New York (1997), or Tijssen (1993) supra, for detailed descriptions of equivalent hybridization and wash conditions and for reagents and buffers, e.g., SSC buffers and equivalent reagents and conditions.

Anti-DNA Repair Enzyme Antibodies

The invention also provides antibodies specifically reactive with the DNA repair enzymes of the invention. The term "antibody" as used herein refers to an immunoglobulin molecule or immunologically active portion thereof, i.e., an antigen-binding portion. Examples of immunologically active portions of immunoglobulin molecules include F(ab) and F(ab')$_2$ fragments which can be generated by treating the antibody with an enzyme such as pepsin. The antibody can be a polyclonal, monoclonal, recombinant, e.g., a chimeric or humanized, fully human, non-human, e.g., murine, or single chain antibody. In one embodiment the antibody has an effector function and can fix complement. The antibody can be coupled to a toxin or imaging agent.

A full-length DNA repair enzyme or, an antigenic peptide fragment thereof, can be used as an immunogen or can be used to identify anti-DNA repair enzyme antibodies made with other immunogens, e.g., cells, membrane preparations, and the like. In various embodiments, antigenic peptides of a DNA repair enzyme can include at least about 8, at least about 8, at least about 15, at least about 20, at least about 25, or at least about 30 amino acid residues of an exemplary sequence of the invention.

Subsequences or fragments of DNA repair enzyme can be used as immunogens or used to characterize the specificity of an antibody. In various embodiments, antibodies of the invention bind to hydrophilic regions of the protein, or, extracellular or, intracellular, or loop, or ligand or second messenger binding regions or motifs (and can also have agonist or antagonist activity). Antibodies reactive with, or specific for, any of these regions, or other regions or domains described herein are provided.

Exemplary epitopes encompassed by DNA repair enzyme antigenic peptides of the invention are regions located on the surface of the protein, e.g., hydrophilic regions, as well as regions with high antigenicity. For example, an Emini surface probability analysis of the protein sequence can be used to indicate the regions that have a particularly high probability of being localized to the surface or solvent (e.g., extracellular or intracellular fluids) of the protein and are thus likely to constitute surface residues useful for targeting antibody production.

Chimeric, humanized, or completely human antibodies are desirable for applications which include repeated administration, e.g., therapeutic treatment (and some diagnostic applications) of human patients. The anti-DNA repair enzyme antibody can be a single chain antibody. A single-chain antibody (scFV) may be engineered (see, for example, Colcher (1999). *Ann. N Y Acad. Sci.* 880:263–80; Reiter (1996) *Clin. Cancer Res.* 2:245–252. The single chain antibody can be dimerized or multimerized to generate multivalent antibodies having specificities for different epitopes of the same target DNA repair enzyme.

An antibody of the invention (e.g., monoclonal antibody or antiserum) can be used to isolate DNA repair enzymes by standard techniques, such as affinity chromatography or immunoprecipitation. Moreover, an anti-DNA repair enzyme antibody can be used to detect DNA repair enzymes (e.g., in a cellular lysate or cell supernatant) in order to evaluate the abundance and pattern of expression of the protein. Anti-DNA repair enzyme antibodies can be used diagnostically to monitor protein levels in tissue as part of a clinical testing procedure, e.g., to, for example, determine the efficacy of a given treatment regimen. Detection can be facilitated by coupling (i.e., physically linking) the antibody to a detectable substance (i.e., antibody labeling). Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}$I, $^{131}$I, $^{35}$S or $^{3}$H.

Methods for Identifying DNA Repair Enzyme Agonists and Antagonists

The invention provides methods (also referred to herein as "screening assays") for identifying modulators, i.e., candidate or test compounds or agents (e.g., proteins, peptides, peptidomimetics, peptoids, small molecules or other drugs) which bind to DNA repair enzymes, have a stimulatory or inhibitory effect on, e.g., DNA repair enzyme expression or activity, or have a stimulatory or inhibitory effect on, e.g., the expression or activity of a DNA repair enzyme. Compounds thus identified can be used to modulate the activity of target gene products (e.g., DNA repair enzyme genes) in a therapeutic protocol, to elaborate the biological function of the target gene product, or to identify compounds that disrupt normal target gene interactions. Exemplary protocols that can be used to measure DNA repair activity are well known in the art, see, e.g., the Examples, below.

The invention provides methods and compositions for determining whether a test compound specifically binds to a DNA repair enzyme in vitro or in vivo. The invention also provides methods and compositions for determining whether a test compound can effect the physiology of a cell expressing a DNA repair enzyme. Any aspect of cell physiology can be monitored to assess the effect of ligand binding to a DNA repair enzyme of the invention.

The invention also provides bacterium and non-human animals expressing one or more DNA repair enzyme sequences of the invention. Such expression can be used to determine whether a test compound specifically binds to a DNA repair enzyme in vivo by contacting a stably or transiently infected organism with a nucleic acid of the invention with a test compound and determining whether the cell or animal reacts to the test compound by specifically binding to the DNA repair enzyme.

The DNA repair enzymes of the invention can be expressed in vivo by delivery with an infecting agent, a vector, or a virus, e.g., adenovirus expression vector. Bacterium and animals infected with the vectors of the invention are particularly useful for assays to identify and characterize ligands that can bind to (and act as antagonists or agonists) of subfamilies of DNA repair enzymes. Such vector-infected animals can be used for in vivo screening of putative ligands and their effect on, e.g., cell physiology, e.g., as with DNA repair.

Test compounds can be obtained using any of the numerous approaches in combinatorial library methods known in the art, including: biological libraries; peptoid libraries (libraries of molecules having the functionalities of peptides, but with a novel, non-peptide backbone which are resistant to enzymatic degradation but which nevertheless remain bioactive, see, e.g., Zuckermann (1994) *J. Med. Chem.* 37: 2678–85; spatially addressable parallel solid phase or solution phase libraries; synthetic library methods requiring deconvolution; the "one-bead one-compound" library method; and synthetic library methods using affinity chromatography selection. The biological library and peptoid library approaches are limited to peptide libraries, while the other four approaches are applicable to peptide, non-peptide oligomer or small molecule libraries of compounds (see, e.g., Lam (1997) *Anticancer Drug Des.* 12:145).

Examples of methods for the synthesis of molecular libraries can be found in the art, for example in: DeWitt (1993) *Proc. Natl. Acad. Sci. U.S.A.* 90:6909; Erb (1994) *Proc. Natl. Acad. Sci. USA* 91:11422; Zuckermann (1994). *J. Med. Chem.* 37:2678; Cho (1993) *Science* 261:1303; Carrell (1994) *Angew. Chem. Int. Ed. Engl.* 33:2059; Carell (1994) *Angew. Chem. Int. Ed. Engl.* 33:2061; Gallop (1994) *J. Med. Chem.* 37:1233. Libraries of compounds may be presented in solution (see, e.g., Houghten (1992) *Biotechniques* 13:412–421), or on beads (see, e.g., Lam (1991) *Nature* 354:82–84), chips (see, e.g., Fodor (1993) *Nature* 364:555–556), bacteria (see, e.g., Ladner U.S. Pat. No. 5,223,409), spores (see, e.g., Ladner U.S. Pat. No. '409), plasmids (see, e.g., Cull (1992) *Proc. Natl. Acad. Sci. USA* 89:1865–1869) or on phage (see, e.g., Scott (1990) *Science* 249:386–390; Cwirla (1990) *Proc. Natl. Acad. Sci.* 87:6378–6382; Felici (1991) *J. Mol Biol* 222:301–310).

In yet another embodiment, a cell-free assay is provided in which a DNA repair enzyme or biologically active portion thereof is contacted with a test compound and the ability of the test compound to bind to the DNA repair enzyme or biologically active portion thereof is evaluated. Biologically active portions of the DNA repair enzymes can be used in assays of the present invention include fragments which participate in interactions with non-DNA repair enzymes, e.g., fragments with high surface probability scores.

Cell-free assays involve preparing a reaction mixture of the target gene protein and the test compound under conditions and for a time sufficient to allow the two components to interact and bind, thus forming a complex that can be removed and/or detected. The interaction between two molecules can also be detected, e.g., using fluorescence energy transfer (FET) (see, for example, Lakowicz et al., U.S. Pat. No. 5,631,169; Stavrianopoulos, et al., U.S. Pat. No. 4,868,103). A fluorophore label on the first, 'donor' molecule is selected such that its emitted fluorescent energy will be absorbed by a fluorescent label on a second, 'acceptor' molecule, which in turn is able to fluoresce due to the absorbed energy. Alternately, the 'donor' protein molecule may simply utilize the natural fluorescent energy of tryptophan residues. Labels are chosen that emit different wavelengths of light, such that the 'acceptor' molecule label may be differentiated from that of the 'donor'. Since the efficiency of energy transfer between the labels is related to the distance separating the molecules, the spatial relationship between the molecules can be assessed. In a situation in which binding occurs between the molecules, the fluorescent emission of the 'acceptor' molecule label in the assay should be maximal. An FET binding event can be conveniently measured through standard fluorometric detection means well known in the art (e.g., using a fluorimeter).

Determining the ability of DNA repair enzymes to bind to a target molecule can be accomplished using real-time Biomolecular Interaction Analysis (BIA) (see, e.g., Sjolander, S. and Urbaniczky, C. (1991) Anal. Chem. 63:2338–2345 and Szabo et al. (1995) Curr. Opin. Struct. Biol. 5:699–705). "Surface plasmon resonance" or "BIA" detects biospecific interactions in real time, without labeling any of the interactants (e.g., BIAcore). Changes in the mass at the binding surface (indicative of a binding event) result in alterations of the refractive index of light near the surface (the optical phenomenon of surface plasmon resonance (SPR)), resulting in a detectable signal which can be used as an indication of real-time reactions between biological molecules.

The target gene product or the test substance can be anchored onto a solid phase. The target gene product/test compound complexes anchored on the solid phase can be detected at the end of the reaction. Preferably, the target gene product can be anchored onto a solid surface, and the test compound, (which is not anchored), can be labeled, either directly or indirectly, with detectable labels discussed herein.

It may be desirable to immobilize either DNA repair enzymes, an anti-antibody or DNA repair enzyme target molecules to facilitate separation of complexed from uncomplexed forms of one or both of the proteins, as well as to accommodate automation of the assay. Binding of a test compound to a DNA repair enzyme, or interaction of DNA repair enzymes with a target molecule in the presence and absence of a candidate compound, can be accomplished in any vessel suitable for containing the reactants. Examples of such vessels include microtiter plates, test tubes, and microcentrifuge tubes. In one embodiment, a fusion protein can be provided which adds a domain that allows one or both of the proteins to be bound to a matrix. For example, glutathione-S-transferase/DNA repair enzyme fusion proteins or glutathione-S-transferase/target fusion proteins can be adsorbed onto glutathione Sepharose™ beads (Sigma Chemical, St. Louis, Mo.) or glutathione derivatized microtiter plates, which are then combined with the test compound or the test compound and either the non-adsorbed target protein or DNA repair enzyme, and the mixture incubated under conditions conducive to complex formation (e.g., at physiological conditions for salt and pH). Following incubation, the beads or microtiter plate wells are washed to remove any unbound components, the matrix immobilized in the case of beads, complex determined either directly or indirectly, for example, as described above. Alternatively, the complexes can be dissociated from the matrix, and the level of DNA repair enzyme binding or activity determined using standard techniques.

Other techniques for immobilizing either DNA repair enzymes or a target molecule on matrices include using conjugation of biotin and streptavidin. Biotinylated DNA repair enzyme or target molecules can be prepared from biotin-NHS (N-hydroxy-succinimide) using techniques known in the art (e.g., biotinylation kit, Pierce Chemicals, Rockford, Ill.), and immobilized in the wells of streptavidin-coated 96 well plates (Pierce Chemical).

Kits

The invention provides kits that contain DNA repair enzymes of the invention. The invention provides kits that contain oligonucleotide primer pairs and/or probes capable of amplifying and/or identifying nucleic acids of the invention. The kit can contain instructional material teaching methodologies, e.g., means to repair DNA using the DNA repair enzymes of the invention.

In one embodiment, the kit can include a compound or agent capable of detecting a DNA repair enzyme of the invention or a corresponding mRNA in a biological sample. A standard can be included. The compound or agent can be packaged in a suitable container. The kit can further comprise instructions for using the kit to detect DNA repair enzyme or nucleic acid.

For antibody-based kits, the kit can include: (1) a first antibody (e.g., attached to a solid support) which binds to a polypeptide corresponding to a DNA repair enzyme of the invention; and, optionally, (2) a second, different antibody which binds to either the polypeptide or the first antibody and is conjugated to a detectable agent.

For oligonucleotide-based kits, the kit can include: (1) an oligonucleotide, e.g., a detectably labeled oligonucleotide, which hybridizes to a nucleic acid sequence encoding a polypeptide corresponding to a marker of the invention or (2) a pair of primers useful for amplifying a nucleic acid molecule corresponding to a marker of the invention. The kit can also includes a buffering agent, a preservative, or a protein stabilizing agent. The kit can also includes components necessary for detecting the detectable agent (e.g., an enzyme or a substrate).

The kit can also contain a control sample or a series of control samples which can be assayed and compared to the test sample contained. Each component of the kit can be enclosed within an individual container and all of the various containers can be within a single package, along with instructions for interpreting the results of the assays performed using the kit.

EXAMPLES

The following examples are offered to illustrate, but not to limit the claimed invention.

Example 1

Isolation and Characterization of DNA Repair Enzyme Sequences

The following example describes the isolation and identification of the novel DNA Repair Enzyme sequences of the invention.

In nature, DNA is undergoing damage caused by endogenous factors, such as various types of active oxygen generated from energy metabolism or oxidation stress, and exogenous factors, such as ultraviolet light, ionizing radiation, or chemical substances. Further, mismatches that do not pair correctly with the template may be generated during DNA replication. For example, accurate DNA strands may not be synthesized in polymerase chain reaction (PCR) depending on the DNA polymerase used. The proteins of the invention are enzymes that repair these mismatches and bring about proper base pairs.

The DNA repair enzymes isolated in the present invention are the four enzymes of MutY, RecJ, RecF and TRCF.

(1) MutY

DNA in aerobic organisms is always being damaged by active oxygen generated from energy metabolism or stress. Guanine is susceptible to oxidation into 8-oxoguanine (GO), which not only pairs with cytosine but also mispairs with adenine during replication, giving rise to C:G to A:T transversion (FIG. 1). In order to prevent this mutation, MutY recognizes A:GO mismatches and removes adenine; recognizes G:GO mismatches and removes guanine; and also recognizes A:G mismatches and removes adenine.

Figure 2:
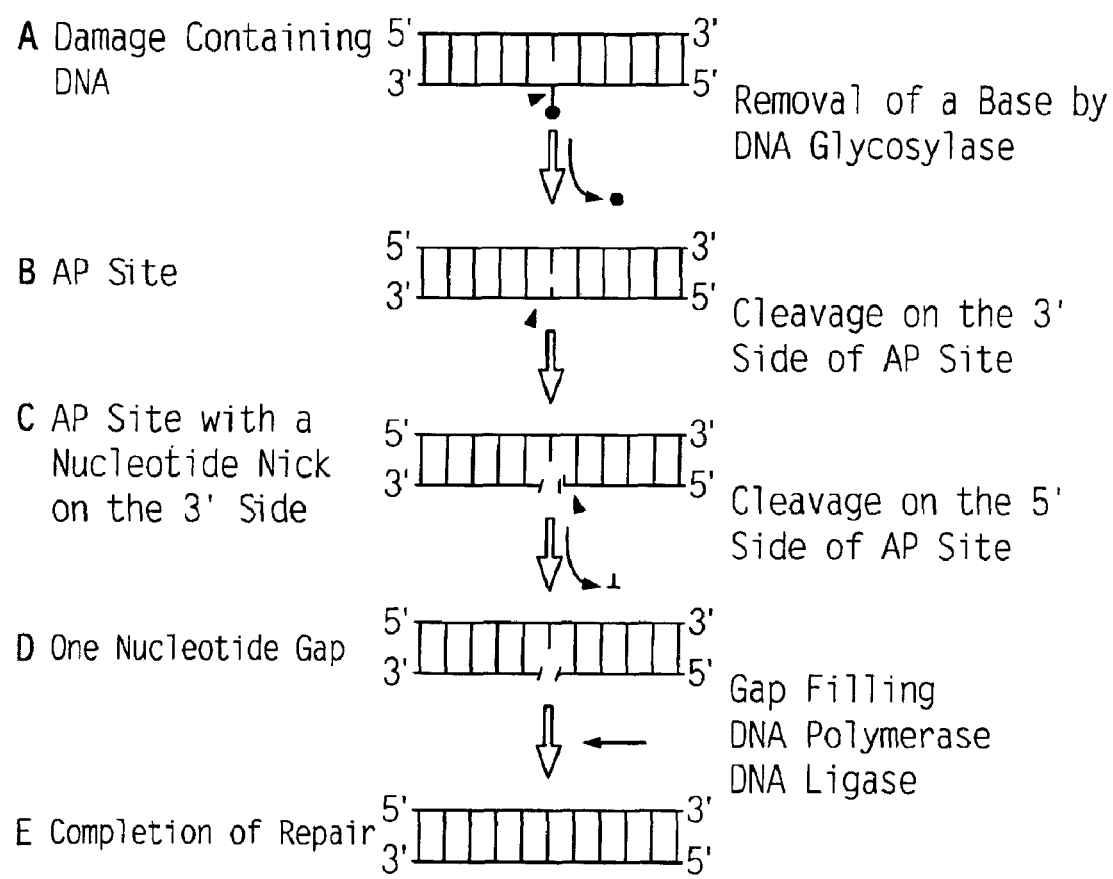
FIG. 2A–E is a diagram showing the base excision repair mechanism of MutY.

Action: Steps of repairing are shown in FIG. 2 (Panels A–E). First, MutY removes the inappropriate base from the damaged site in DNA by its DNA glycosylase activity (Panel A). Then, MutY cuts the DNA strand on the 3' side of the base-removed site (AP site) by its AP lyase activity (Panel B). Finally, the gap is filled by the actions of esterase, DNA polymerase and DNA ligase. Thus, the repair is completed (Panel E).

Figure 3:
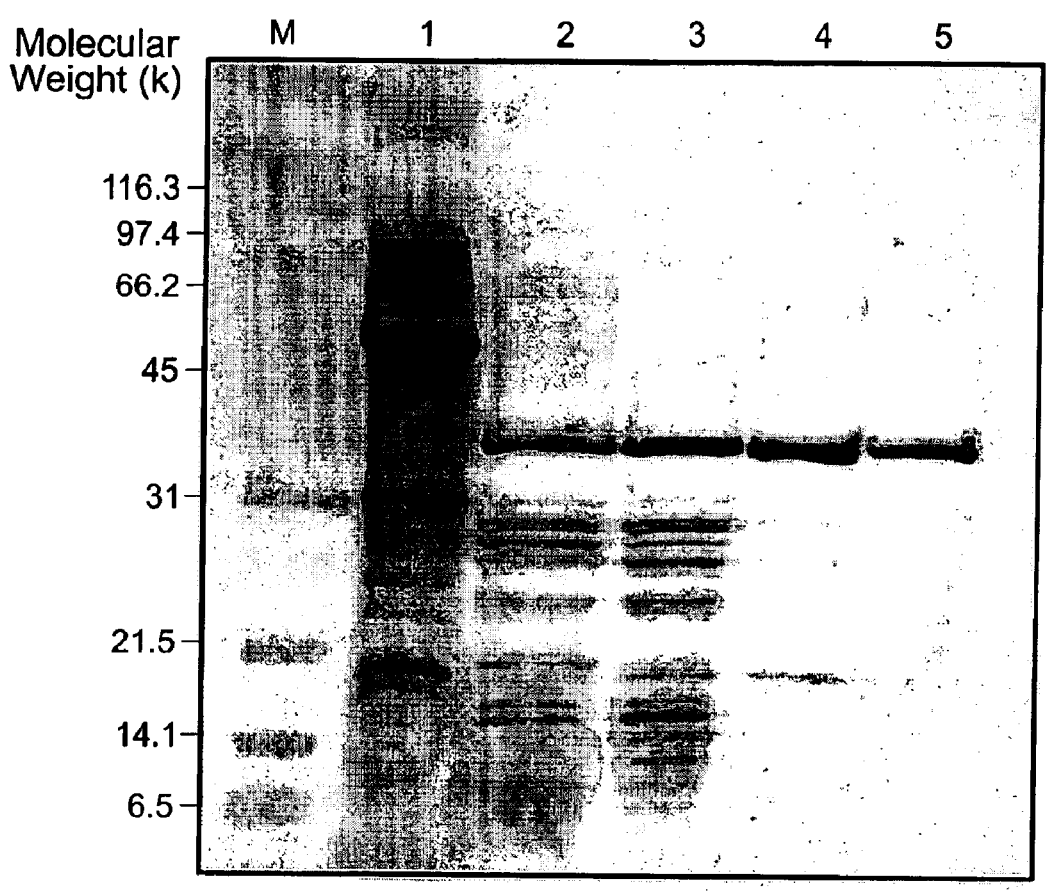
FIG. 3 is a representation of a photograph showing the results of SDS-polyacrylamide gel electrophoresis of MutY.
Figure 4:
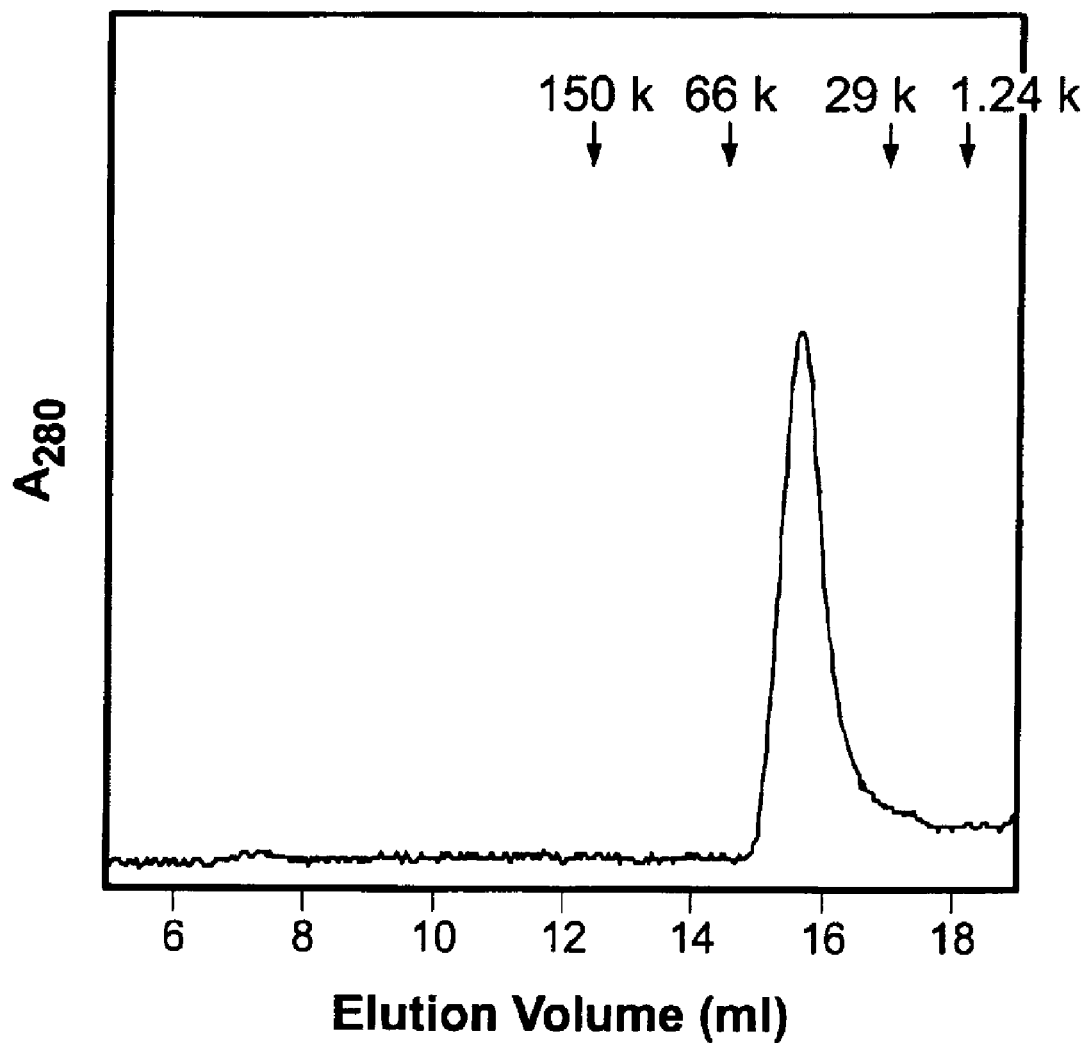
FIG. 4 is a chart showing the results of gel filtration of MutY.
Figure 6:
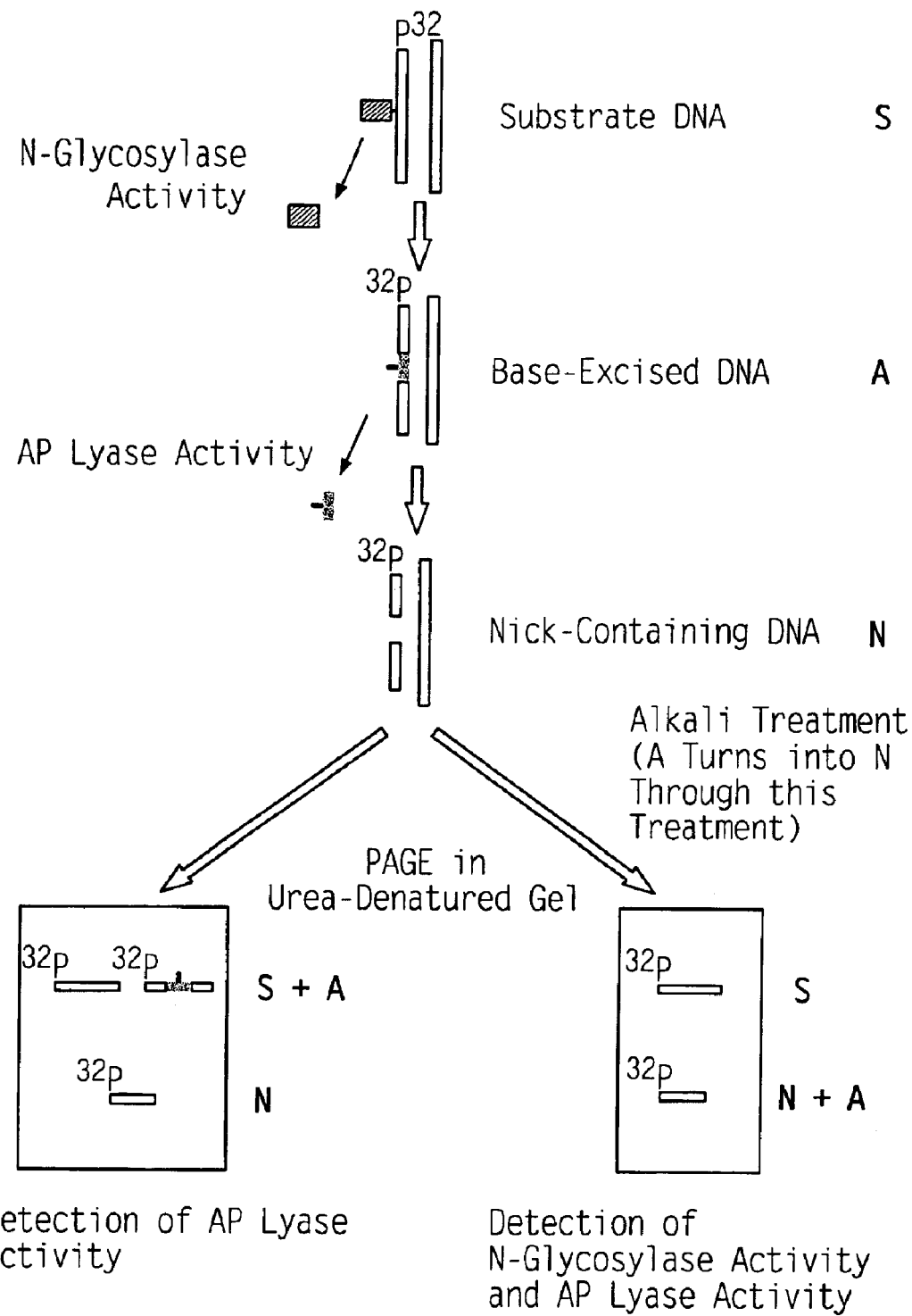
FIG. 6 is a diagram showing an outline of the method of measurement of MutY activities.
Figure 7:
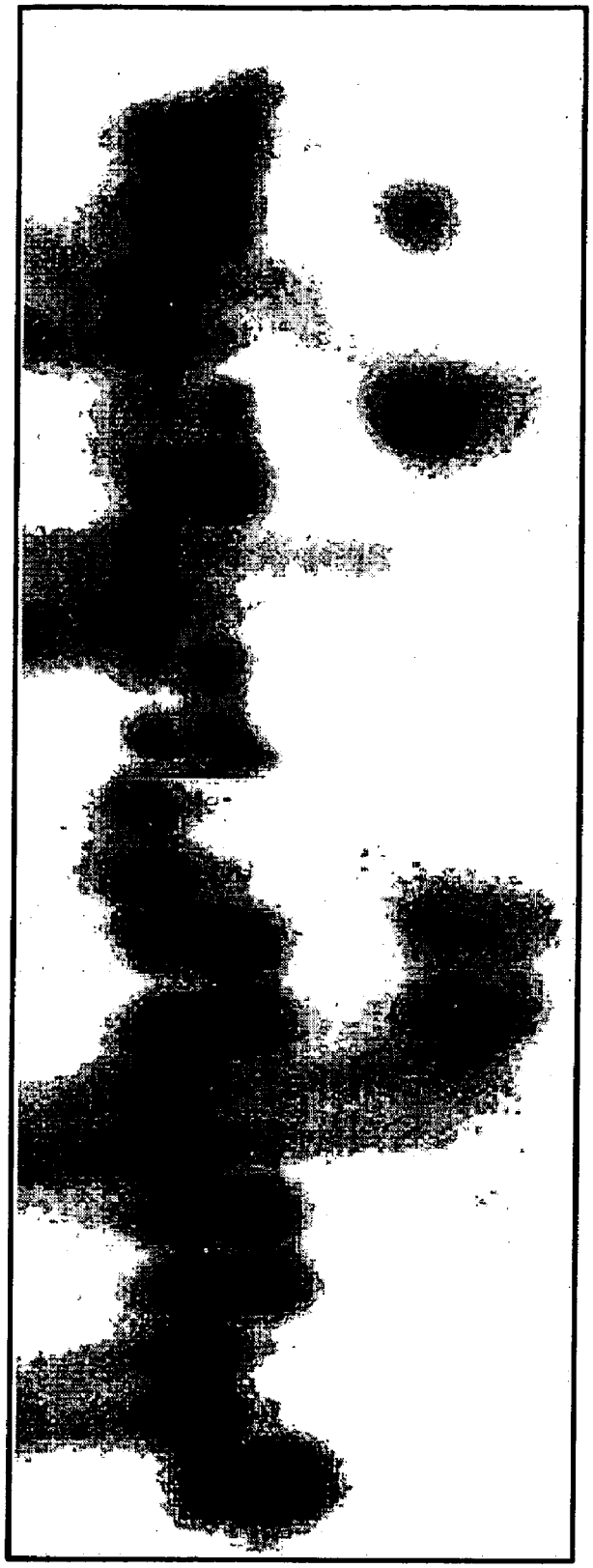
FIG. 7 is a diagram showing the substrate specificity of MutY.

Molecular Weight: The theoretical molecular weight of the MutY of the invention calculated from its amino acid sequence is 36 kDa; the molecular weight estimated from SDS-polyacrylamide gel electrophoresis is ~36 kDa (FIG. 3); and the molecular weight estimated from gel filtration (Superdex 200HR™, 50 mM Tris-HCl (pH 8), 0.5 M NaCl) is 31 kDa (FIG. 4).

Amino Acid Sequence: The sequence is shown in SEQ ID NO: 2. Comparison of this sequence with amino acid sequences of other microorganisms-derived MutY proteins reveals that the residue essential for N-glycosylase activity and residues constituting an iron-sulfur cluster are conserved (FIG. 5).

Substrate Specificity: MutY recognizes A:GO mismatches, A:G mismatches and G:GO mismatches, and removes inappropriate bases.

Figure 8:
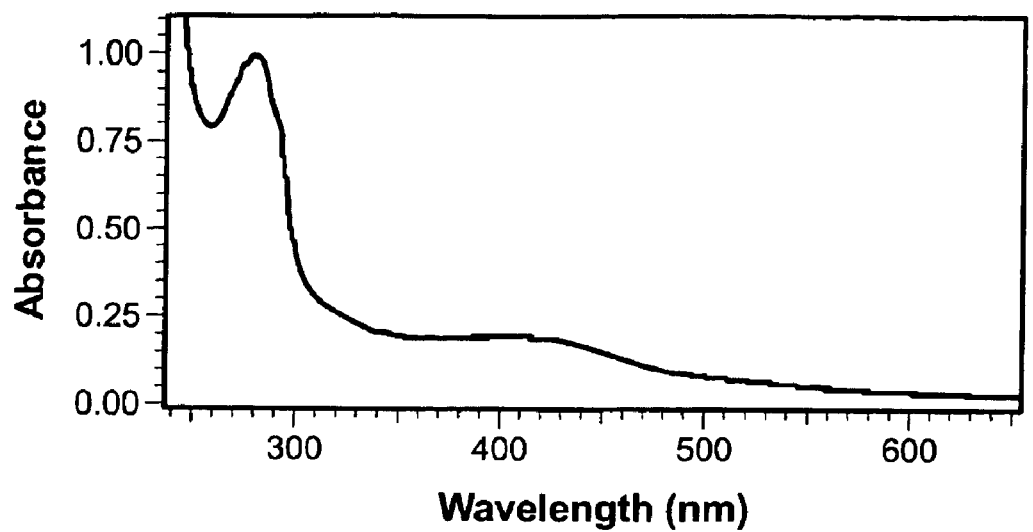
FIG. 8 is a chart showing the absorption spectrum of MutY.
Figure 9:
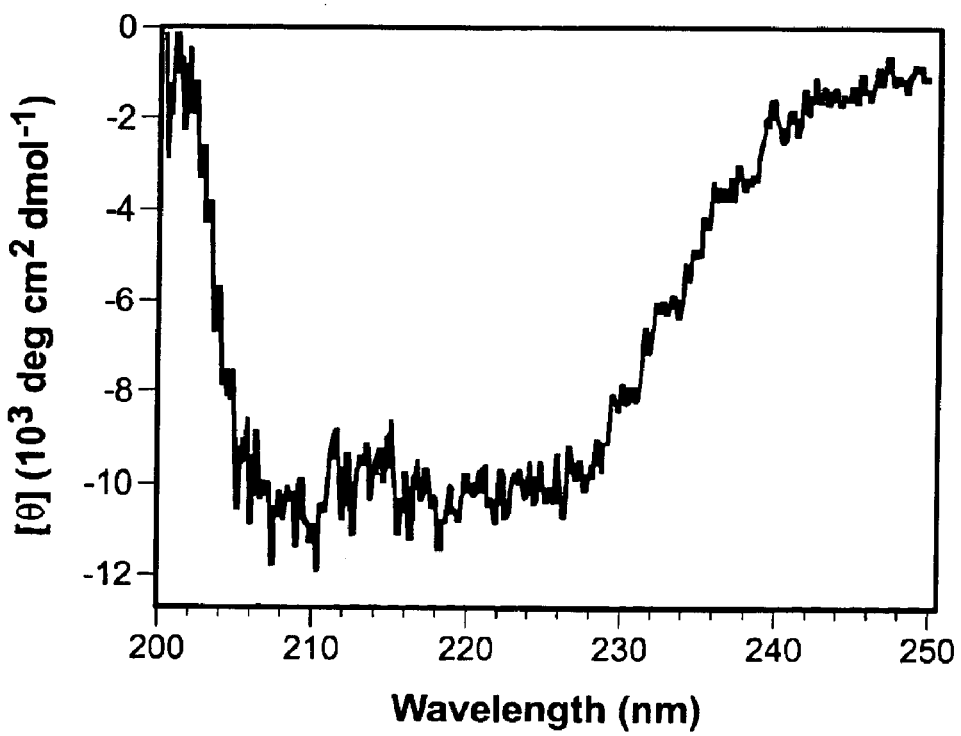
FIG. 9 is a chart showing the CD spectrum of MutY.

Absorption Spectrum: The results of measurement in solution containing 50 mM potassium phosphate (pH 7.5), 0.8 M KCl, 1 mM DTT, 1 mM EDTA and 10% glycerol revealed that MutY has a spectrum peculiar to an iron-sulfur cluster at around 410 nm (FIG. 8).

α-Helix Content: The results of CD spectrum analysis in a solution containing 50 mM Tris-HCl (pH 8.0), 0.1 M KCl, 1 mM DTE, 1 mM EDTA and 20% glycerol revealed that α-helix content is ~40% (FIG. 9).

Figure 10:
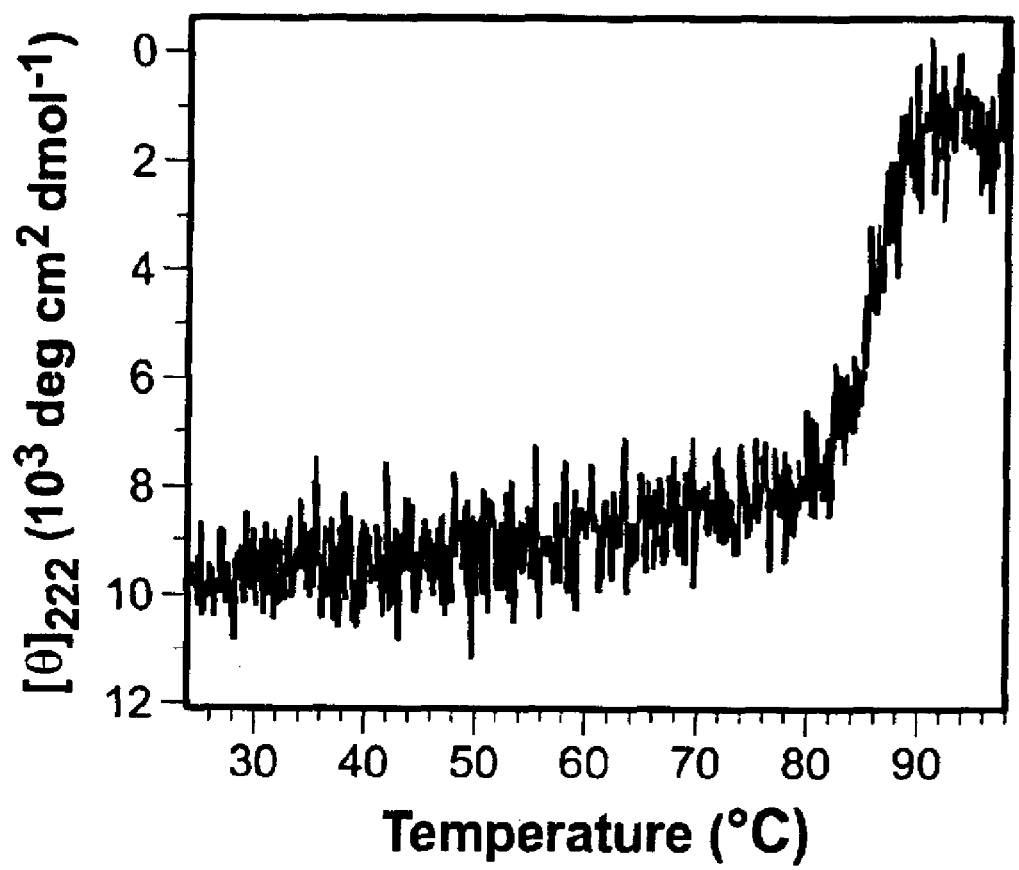
FIG. 10 is a chart showing the thermostability of MutY.
Figure 11:
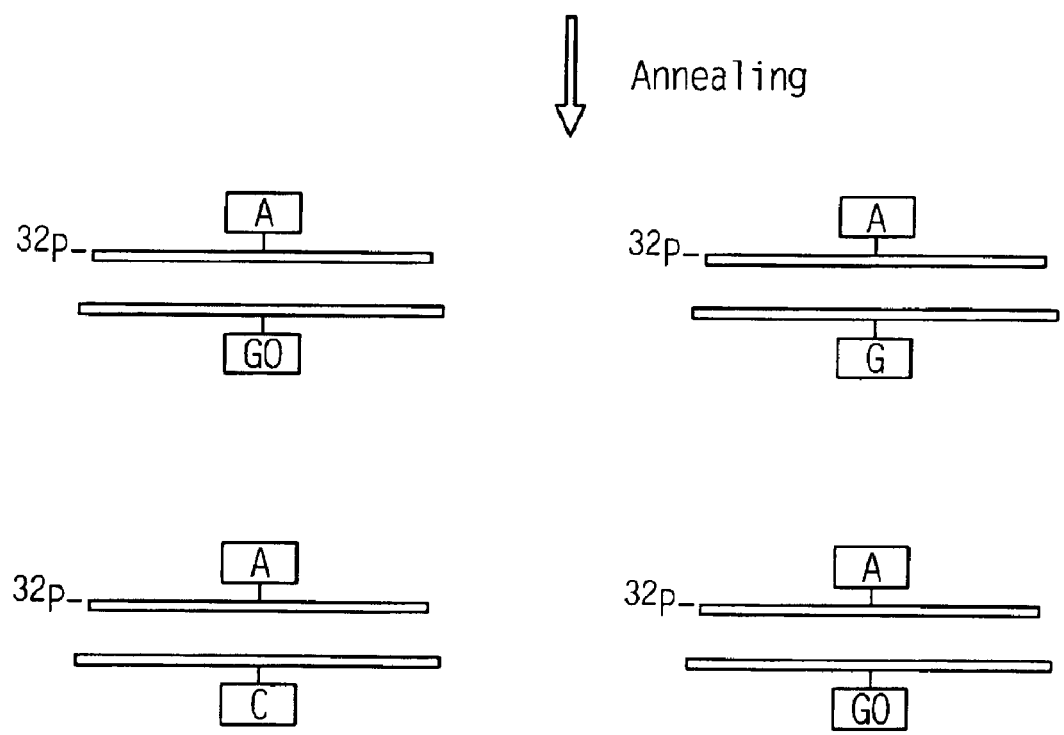
FIG. 11 is a diagram showing substrate DNA and 32P-labeled site (SEQ ID NOs: 18 and 19).

Thermostability: The results of analysis of CD spectrum at varied temperatures in a solution containing 50 mM potassium phosphate (pH 7.5), 0.1 M KCl, 1 mM DTE, 1 mM EDTA and 20% glycerol revealed that MutY is stable at temperatures from 24° C. to 80° C. (especially, up to 75° C.) under neutral conditions (pH 7.5) (FIG. 10).

(2) RecJ

Figure 12:
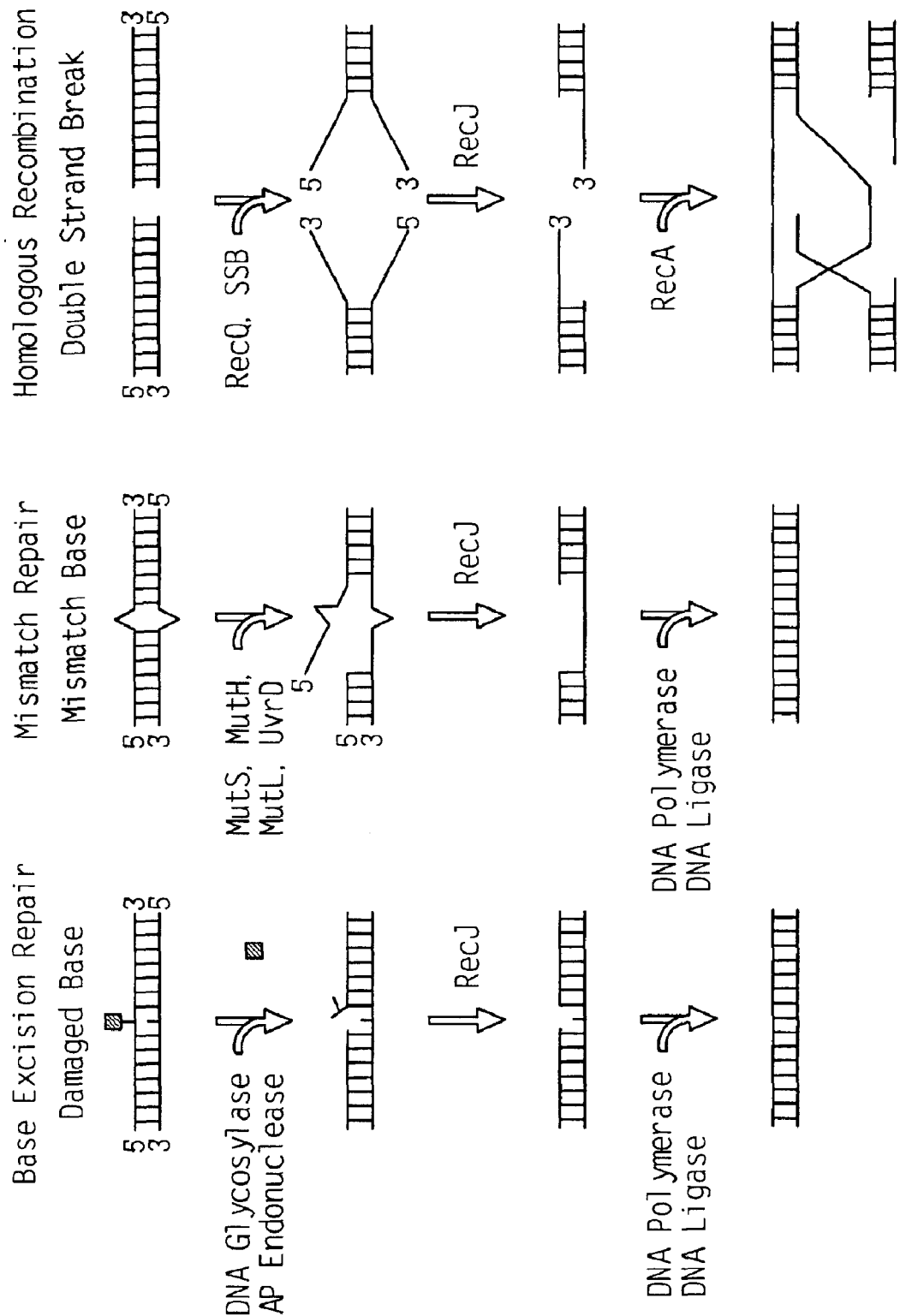
FIG. 12 is a diagram showing the function of RecJ.

RecJ is a DNA repair enzyme with both exonuclease activity specific to single-stranded DNA and deoxyribodiesterase activity, and is involved in both base excision repair system and mismatch repair system (FIG. 12). It is also known that RecJ carries out the initial process of homologous recombination in cooperation with RecQ and SSB (both of which are single-stranded DNA-binding proteins).

In base excision repair system, the function of RecJ is to cut the DNA strand on the 3' side of the nick generated by the actions of DNA glycosylase and AP endonuclease (FIG. 12, Left Panel).

In mismatch repair system, the function of RecJ is to degrade from the 5' to 3' direction the single-stranded DNA generated by the action of MutS, MutH, MutL or UvrD (FIG. 12, Central Panel).

In homologous recombination system, the function of RecJ is to degrade from the 5' to 3' direction the single-stranded DNA generated by the action of RecQ or SSB (FIG. 12, Right Panel).

RecJ homologues are found widely not only in prokaryotes but also in eukaryotes, such as yeast and *Drosophila*, and share characteristic motifs (FIG. 14).

Action: RecJ has exonuclease activity that degrades single-stranded DNA only in the 5' to 3' direction (FIG. 12).

Figure 13:
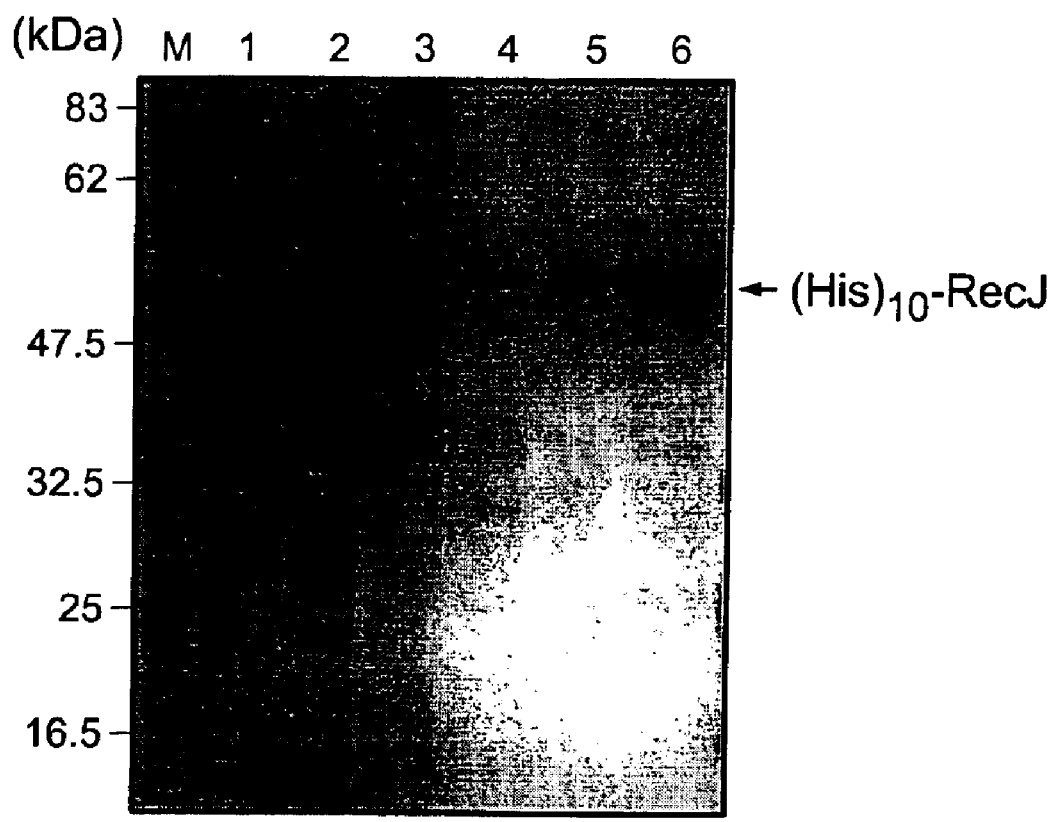
FIG. 13 is a representation of a photograph showing the results of SDS-polyacrylamide gel electrophoresis of RecJ.

Molecular Weight: The theoretical molecular weight of the RecJ of the invention calculated from its amino acid sequence is ~50 kDa, and the molecular weight estimated from SDS-polyacrylamide gel electrophoresis is ~50 kDa (FIG. 13).

Amino Acid Sequence: The sequence is shown in SEQ ID NO: 4.

Figure 15:
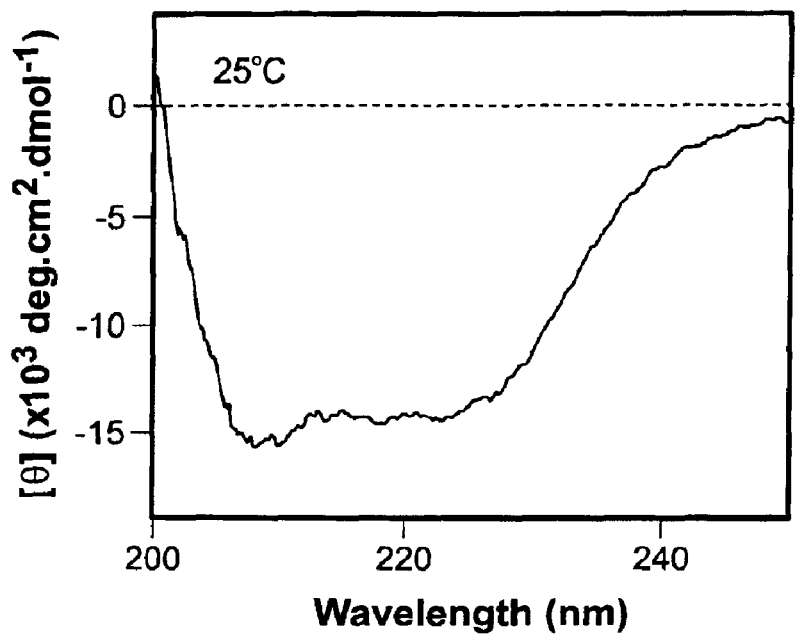
FIG. 15 is a chart showing the CD spectrum of RecJ.

Substrate Specificity: RecJ has specificity to single-stranded DNA, and the Km value is 6.2 μM (FIGS. 17–23).

α-Helix Content: The results of CD spectrum analysis in a solution containing 50 mM K-Pi, 100 mM KCl, 0.1 mM DTE and 0.1 mM EDTA (pH 7.2) revealed that α-helix content is ~50% (FIG. 15).

Figure 16:
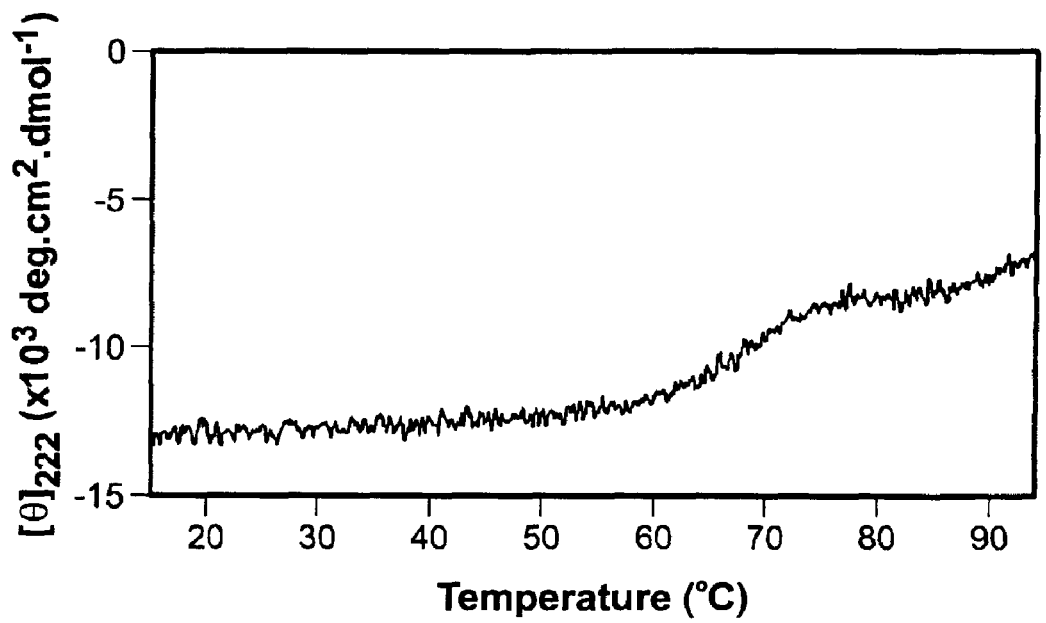
FIG. 16 is a chart showing the thermostability of RecJ.

Thermostability: The results of measurement of CD spectrum at varied temperatures using 1.6 μM RecJ in a solution containing 50 mM K-Pi, 100 mM KCl, 0.1 mM DTE and 0.1 mM EDTA (pH 7.2) revealed that the RecJ of the invention is stable up to 60° C. (FIG. 16).

(3) RecF

From the results of genetic analyses so far made, it is known that RecF protein performs important functions in DNA recombinatorial repair, genetic recombination and DNA replication.

Figure 24:
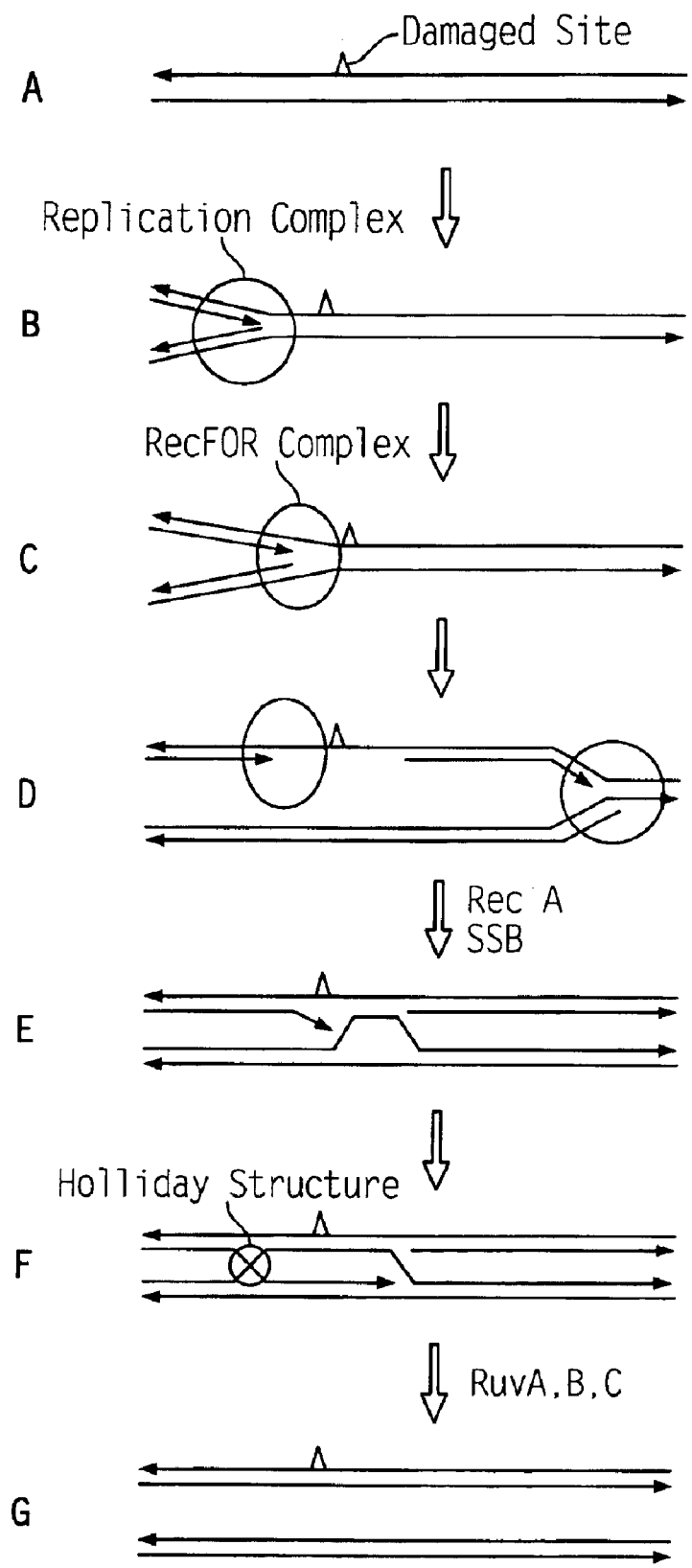
FIG. 24A–G is a diagram sowing thr reaction pathway of RecF.

Action: In cooperation with RecO and RecR proteins, RecF prevents replication at damaged sites (FIG. 24). Briefly, when damage has occurred in DNA (Panel A) and the reaction of a replication complex stops at that site (Panel B), a complex of RecF-RecO-RecR proteins (RecFOR) binds to the DNA (Panel C). Then, replication re-starts (Panel D), and RecA causes pairing of homologous regions (Panel E), leading to strand exchange and DNA synthesis (Panel F). Subsequently, RuvA, RuvB and RuvC dissolve the Holliday structure formed by the pairing of homologous strands (a structure in which a homologous daughter strand is paired with each strand of a double-stranded DNA) to complete the repair (Panel G).

Figure 25:
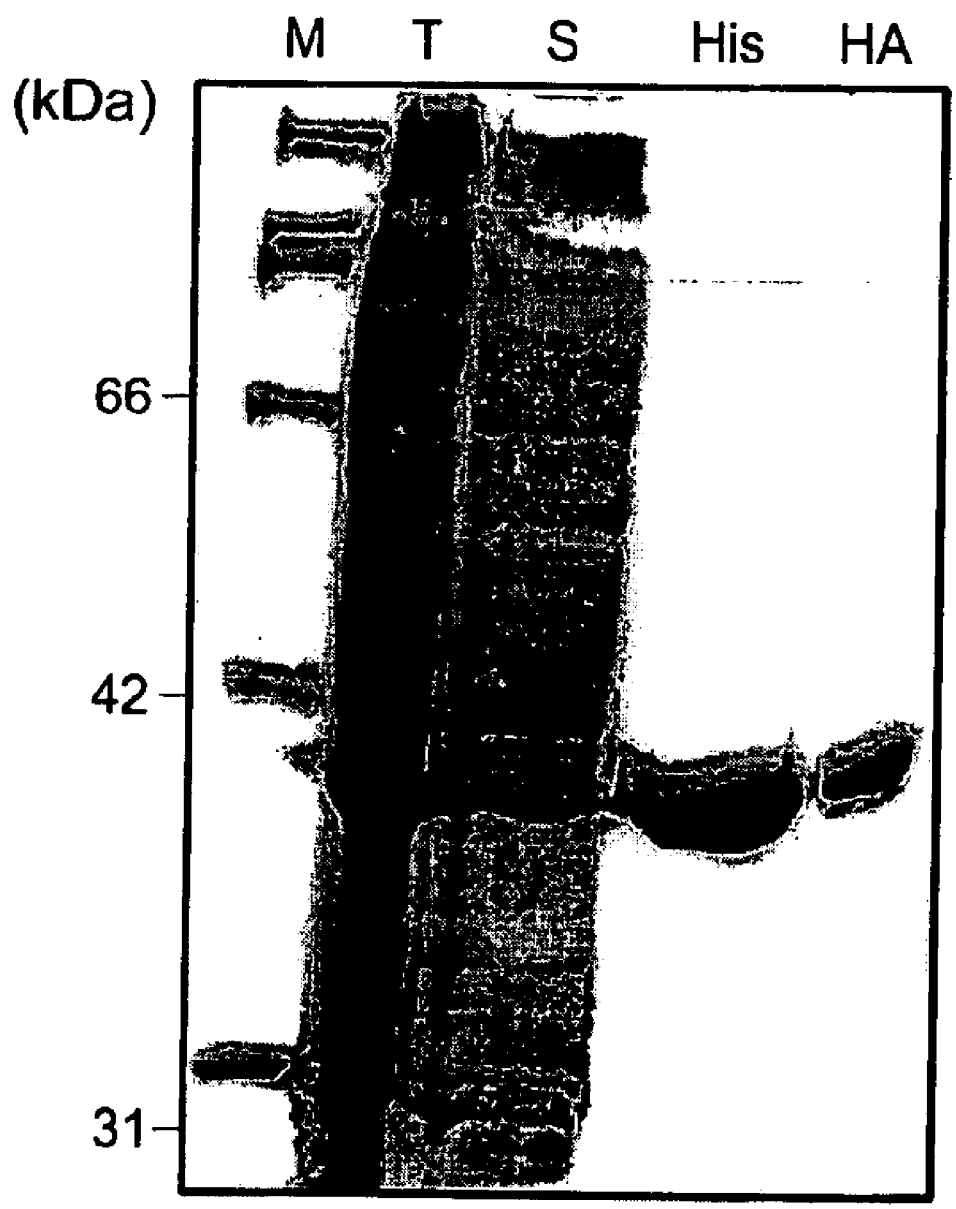
FIG. 25 is a representation of a photograph showing the results of SDS-polyacrylamide gel electrophoresis of RecF.
Figure 26:
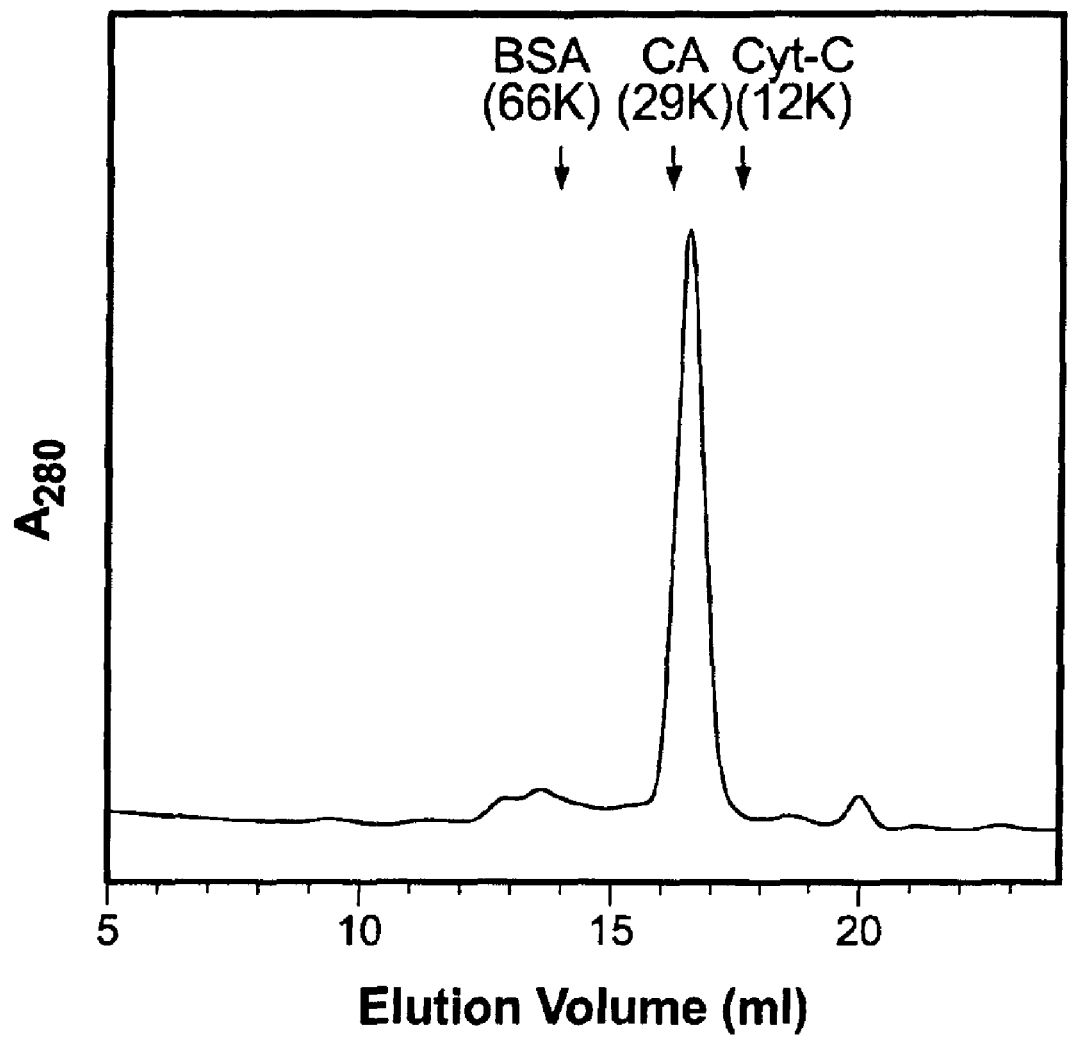
FIG. 26 is a chart showing the results of gel filtration of RecF.

Molecular Weight: The theoretical molecular weight of the RecF of the invention calculated from its amino acid sequence is 37.8 kDa; the molecular weight estimated from gel filtration (Superdex 200HR™, 50 mM Tris-HCl, 2.0 M KCl (pH 7.5)) is 22 kDa (FIG. 26); and the molecular weight estimated from SDS-polyacrylamide gel electrophoresis is 37 kDa (FIG. 25).

Figure 27:
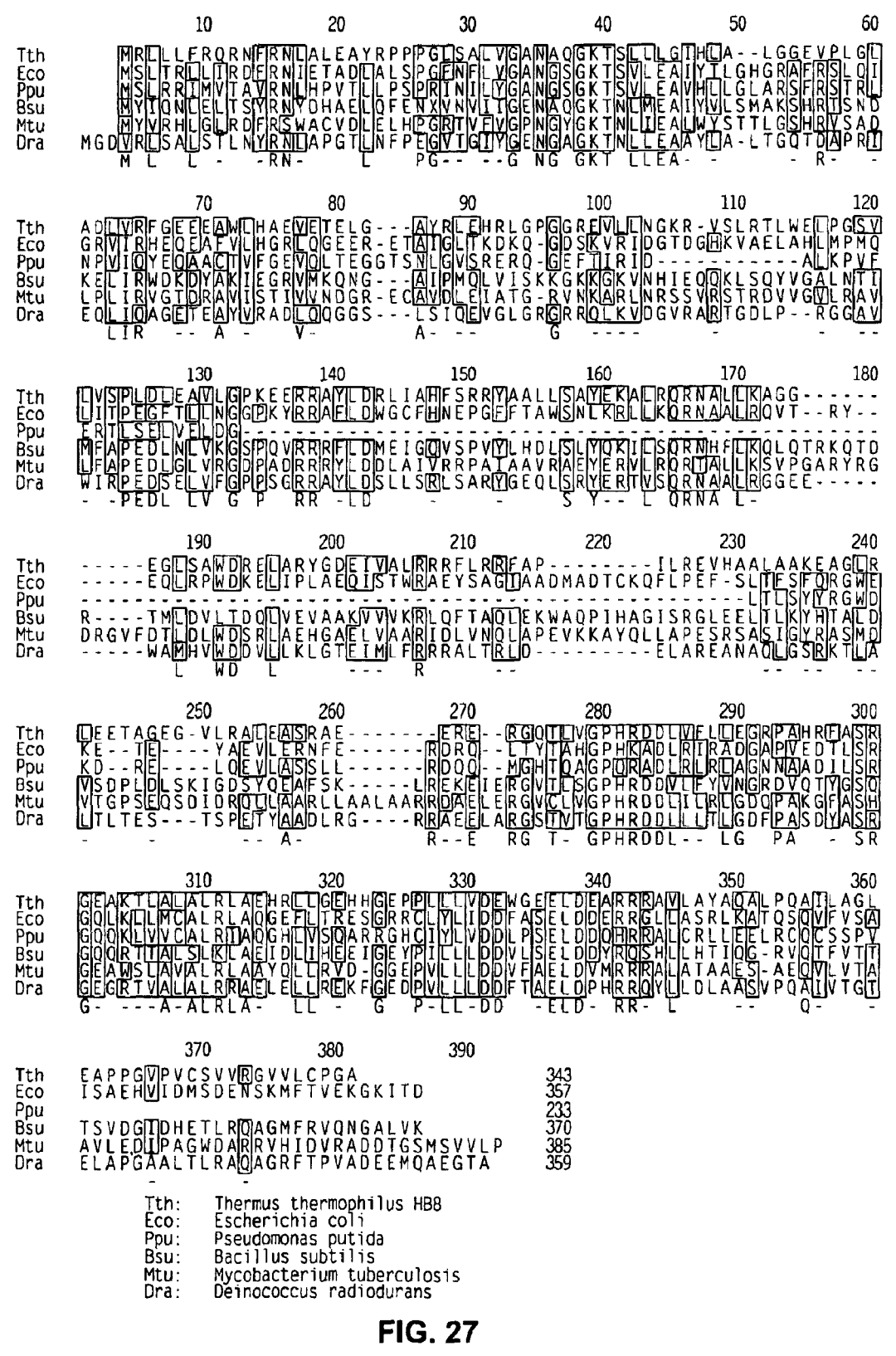

Amino Acid Sequence: The sequence is shown in SEQ ID NO: 8. When this sequence is compared with amino acid sequences of other microorganisms-derived RecF proteins, high homology is observed partially (FIG. 27).

Substrate Specificity: The Km value is 31 μM at 37° C. and 32 μM at 25° C.

α-Helix Content: The results of CD spectrum analysis in a solution containing 50 mM Tris-HCl and 100 mM KCl (pH7.2) revealed that a-helix content is ~40%.

Thermostability: The results of CD spectrum analysis revealed that RecF is stable up to ~50° C. at pH 7.5.

Figure 29:
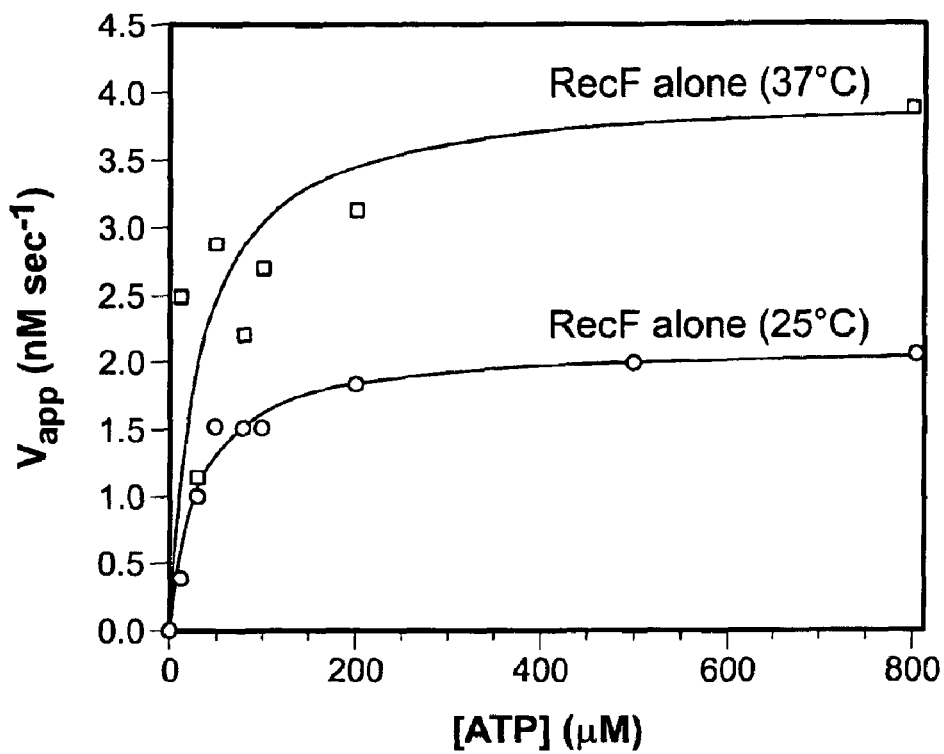
FIG. 29 is a graph showing ATPase activity.
Figure 30:
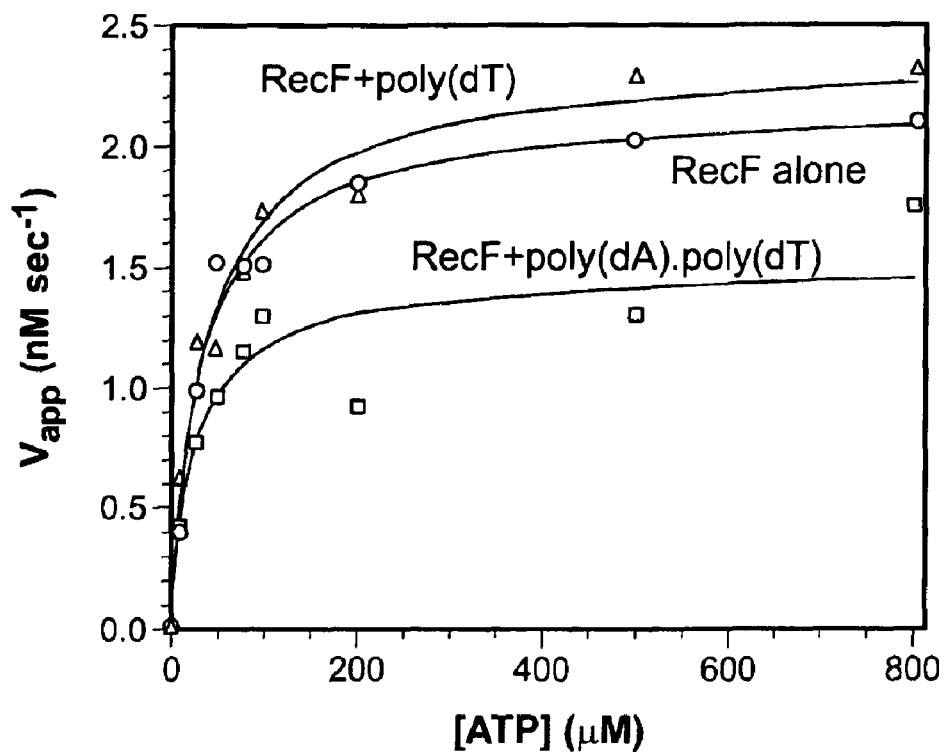
FIG. 30 is a graph showing ATPase activity (DNA dependency).

ATPase Activity: RecF, even alone, has ATPase activity (FIG. 29). This activity is increased when the substrate is single-stranded DNA, and decreased when the substrate is double-stranded DNA (FIG. 30).

(4) TRCF

Figure 32:
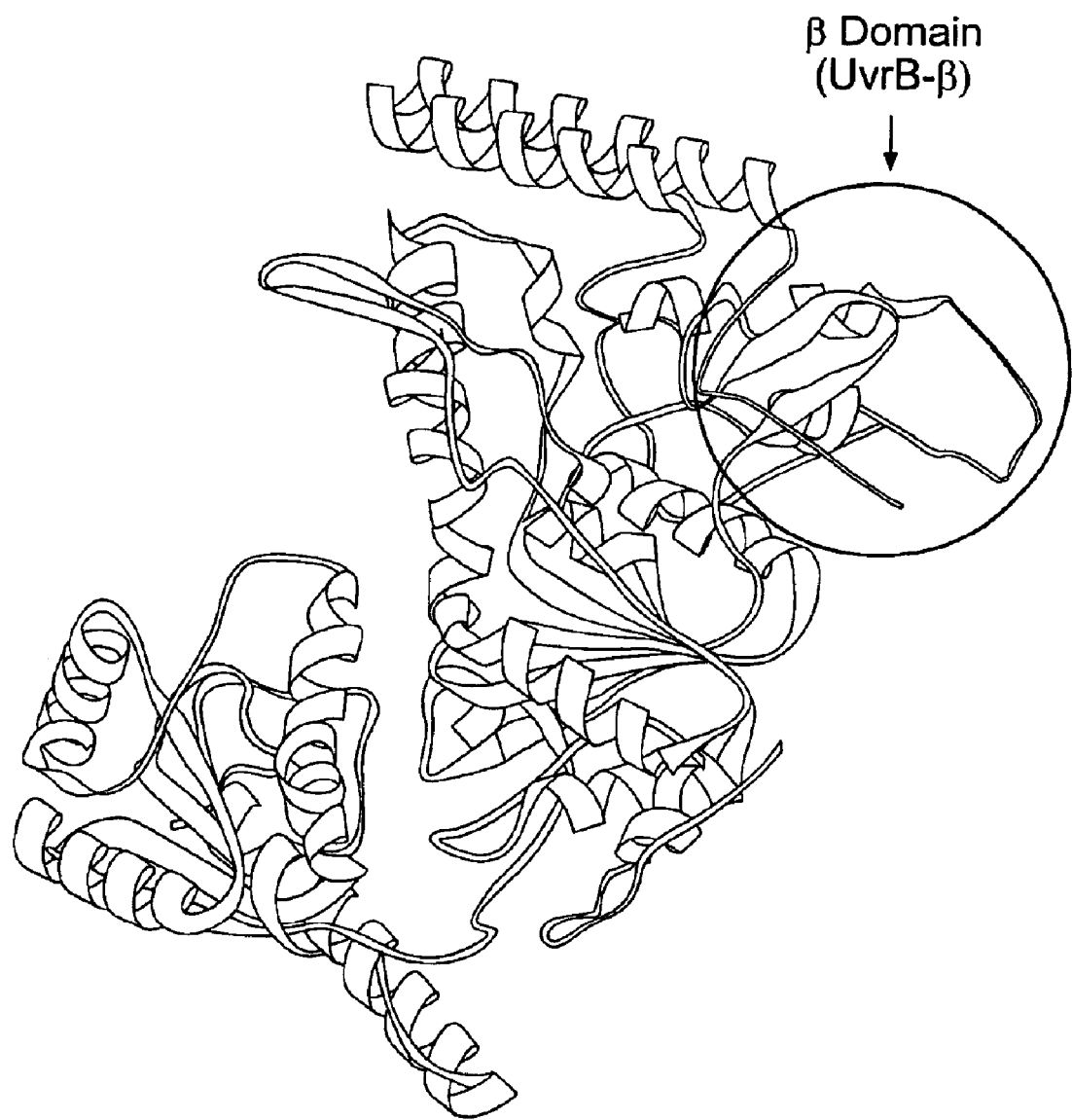
FIG. 32 is a drawing showing the three-dimensional structure of UvrB.

Nucleotide excision repair performed by UvrA, UvrB and UvrC proteins is a mechanism which can recognize and remove DNA damage in the most wide range. Of these proteins, UvrA and UvrB form a complex, UvrAB, which specifically recognizes DNA damage. The results of three-dimensional structural analysis of UvrB revealed that a region that is believed to interact with UvrA forms one domain comprising β-sheet (UvrB-β) (FIG. 32) (Nakagawa et al., J. Biochem. 126, 986–990, 1999). TRCF (transcription-repair coupling factor) is a factor that interacts with UvrA and promotes the repair of damage-containing transcribed strands. TRCF has a region (TRCF-β homologous to the amino acid sequence of UvrB-β. This region is believed to be the binding site for UvrA.

Figure 31:
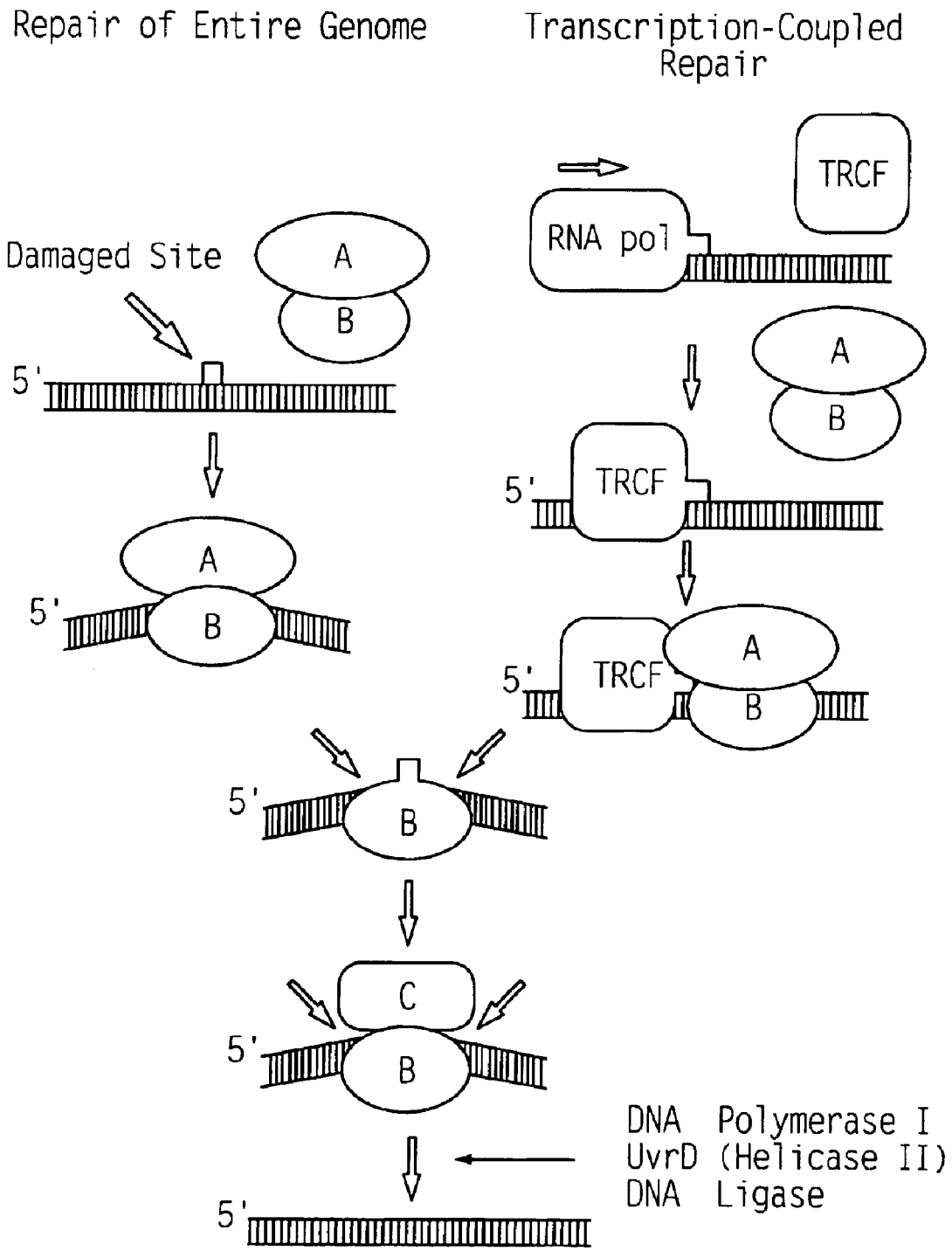
FIG. 31 is a diagram showing the nucleotide excision repair mechanism of TRCF.

Action: TRCF interacts with UvrA and promotes the repair of damage-containing transcribed strands (FIG. 31). Nucleotide excision repair mechanism in prokaryotes is as described below (FIG. 31). Briefly, the complex UvrAB recognizes a damaged site and binds thereto. Damage in transcribed strands is recognized by TRCF and UvrA. Then, the both ends of the damaged site are cut by the action of UvrC, and the site is removed. Subsequently, repair synthesis is completed by the actions of UvrD (helicase II), DNA polymerase I and DNA ligase.

Figure 33A:
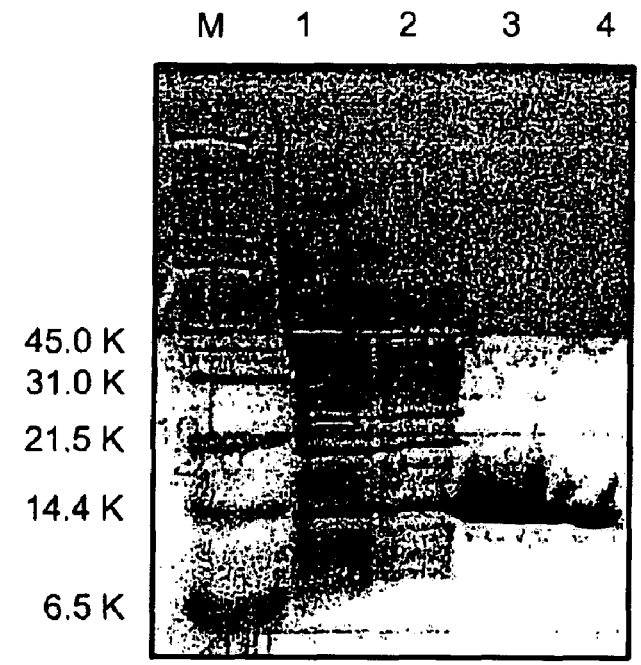
FIG. 33 is a representation of photographs showing the results of SDS-polyacrylamide gel electrophoresis of TRCF-β and UvrB-β, respectively.
Figure 33B:
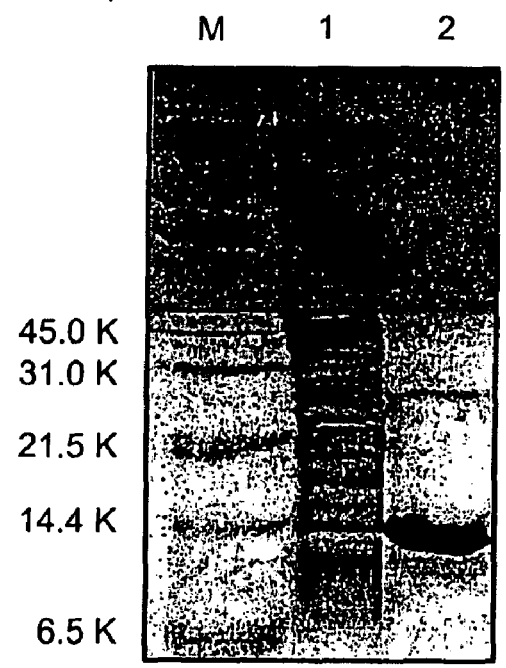

Molecular Weight: The theoretical molecular weight of the TRCF of the invention calculated from its amino acid sequence is 37.8 kDa, and the theoretical molecular weight of TRCF-β region that is believed to be the binding site for UvrA is 14.4 kDa. The molecular weight of TRCF-β region estimated from SDS-polyacrylamide gel electrophoresis is 14.4 kDa (FIG. 33, Lower Panel).

Figure 34:
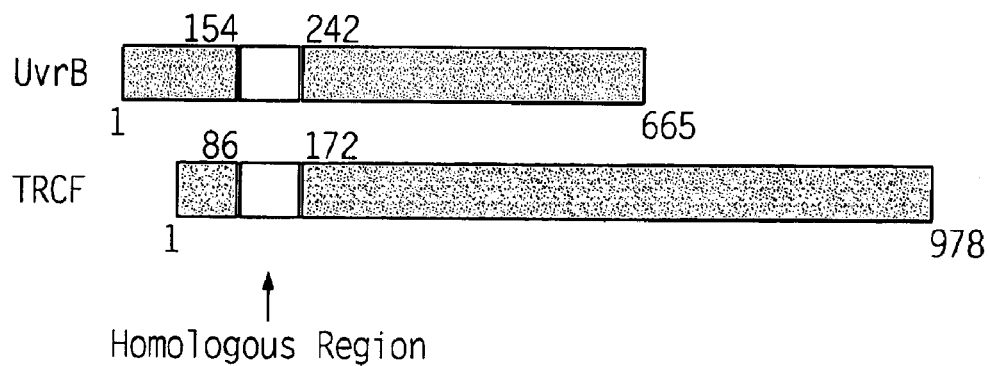
FIG. 34 is an alignment of the amino acid sequence of TRCF-β (SEQ ID NO:65) and UvrB-β (SEQ ID NO:64).

Amino Acid Sequence: The sequence is shown in SEQ ID NO: 6. The amino acid sequences of the homologous regions between UvrB and TRCF (i.e., UvrB-β and TRCF-β) are highly conserved (FIG. 34).

Figure 35A:
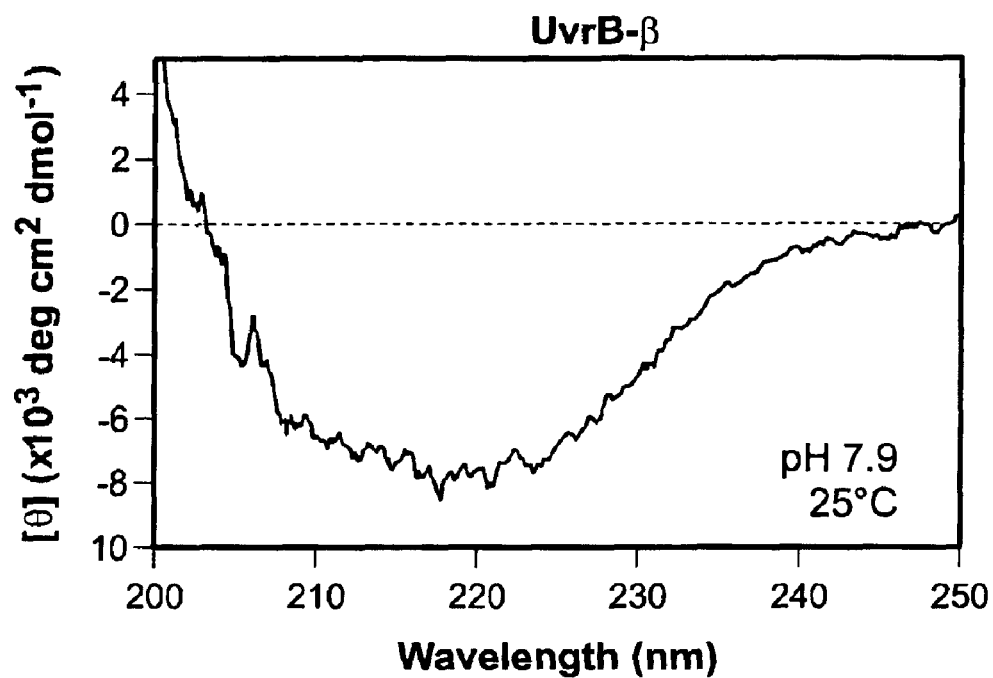
FIG. 35 presents charts showing the SD spectra of TRCF-β and UvrB-β, respectively.
Figure 35B:
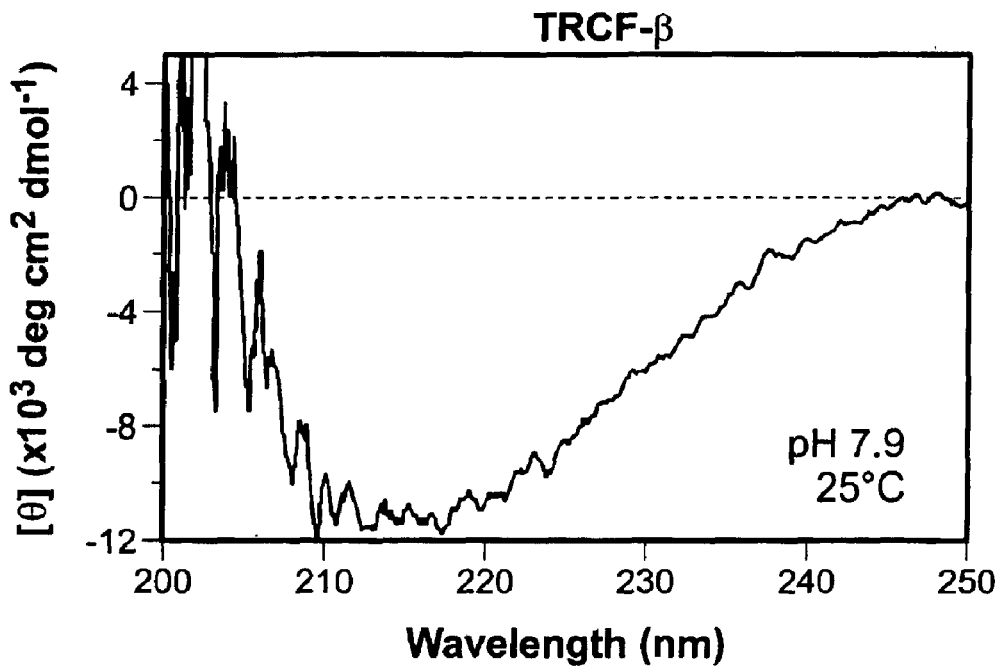

CD Spectrum: The CD spectrum of TRCF-β measured in a buffer containing 50 mM Tris-HCl, 100 mM KCl (pH 7.9) resembles the CD spectrum of UvrB-β measured under the same conditions (FIG. 35).

Figure 36A:
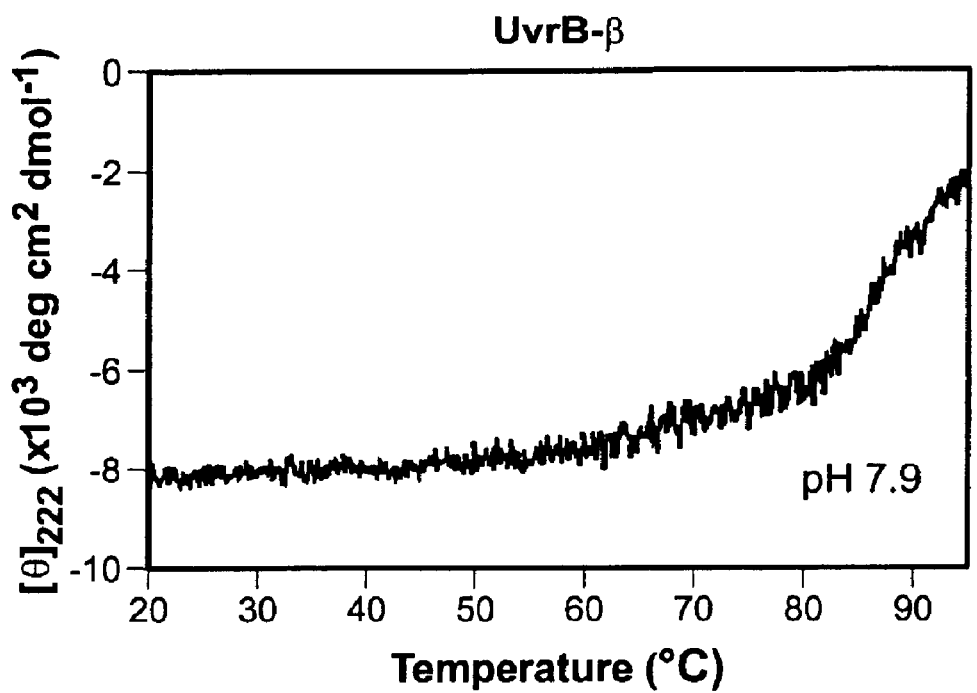
FIG. 36 presents charts showing the thermostabilities of TRCF-β and UvrB-β, respectively.
Figure 36B:
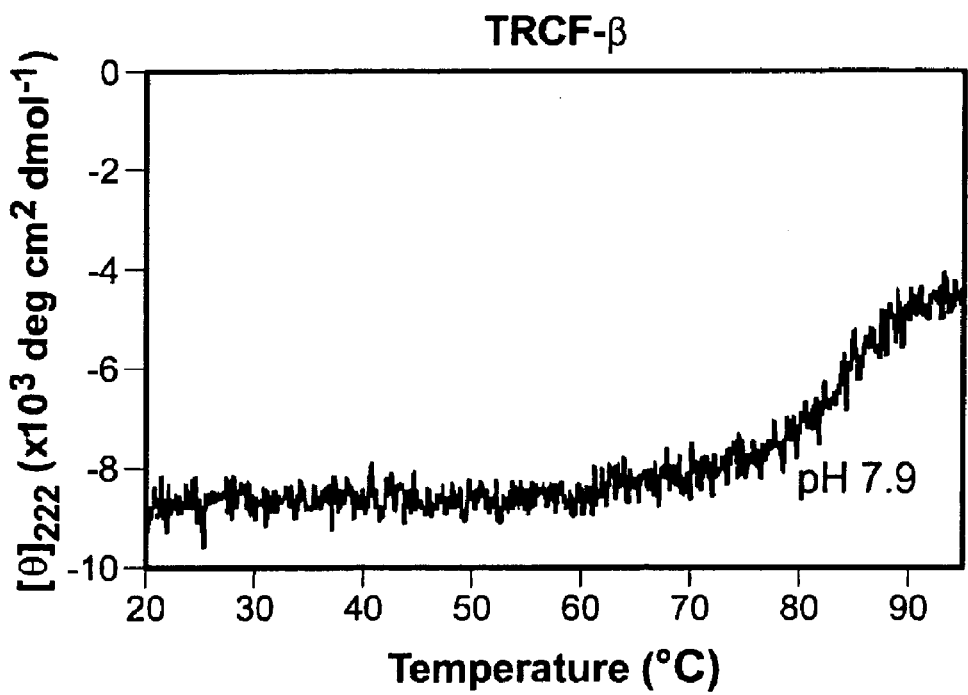
Figure 37A:
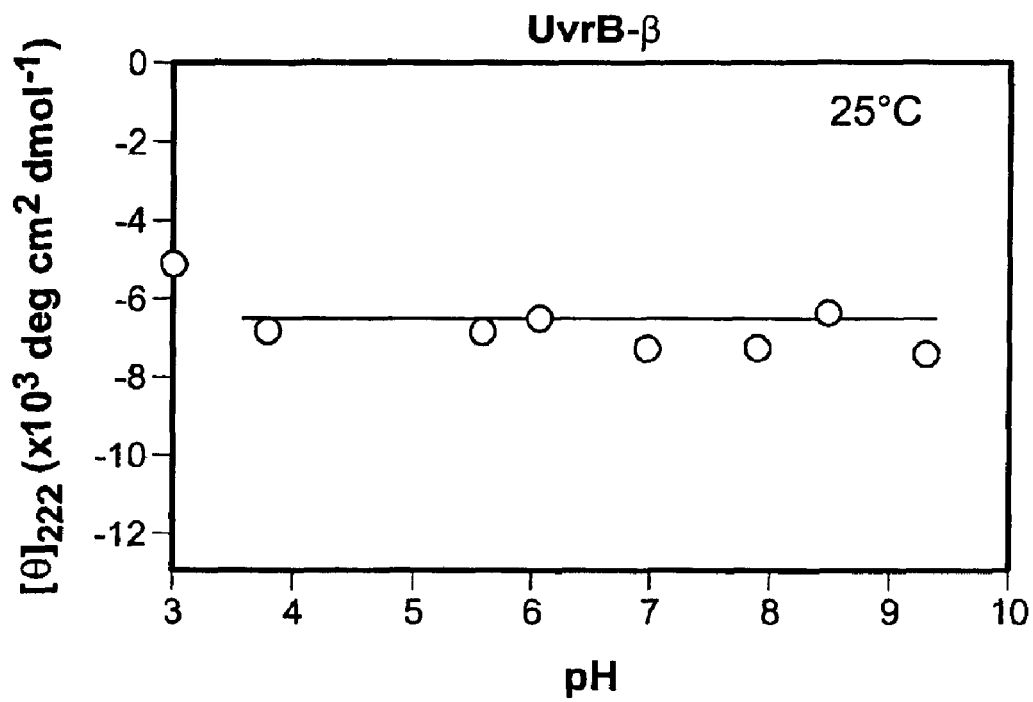
FIG. 37 presents charts showing the pH stabilities of TRCF-β and UvrB-β, respectively.
Figure 37B:
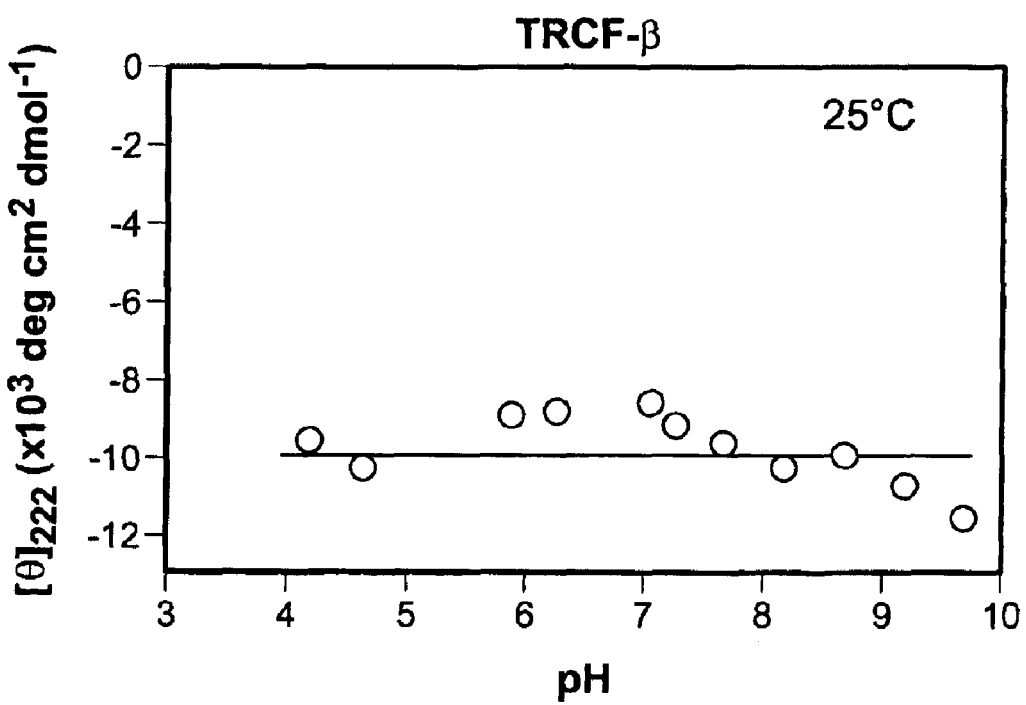

Thermostability: The results of measurement of TRCF-β CD spectrum in a buffer containing 50 mM Tris-HCl, 100 mM KCl (pH 7.9) revealed that TRCF-β is stable at temperatures 20° C.–75° C. (FIG. 36).

pH Stability: The results of measurement of TRCF-β CD spectrum in various buffers containing 100 mM KCl revealed that TRCF-β is stable in a range from pH 4 to pH 9 at 25° C. (FIG. 37).

Figure 38:
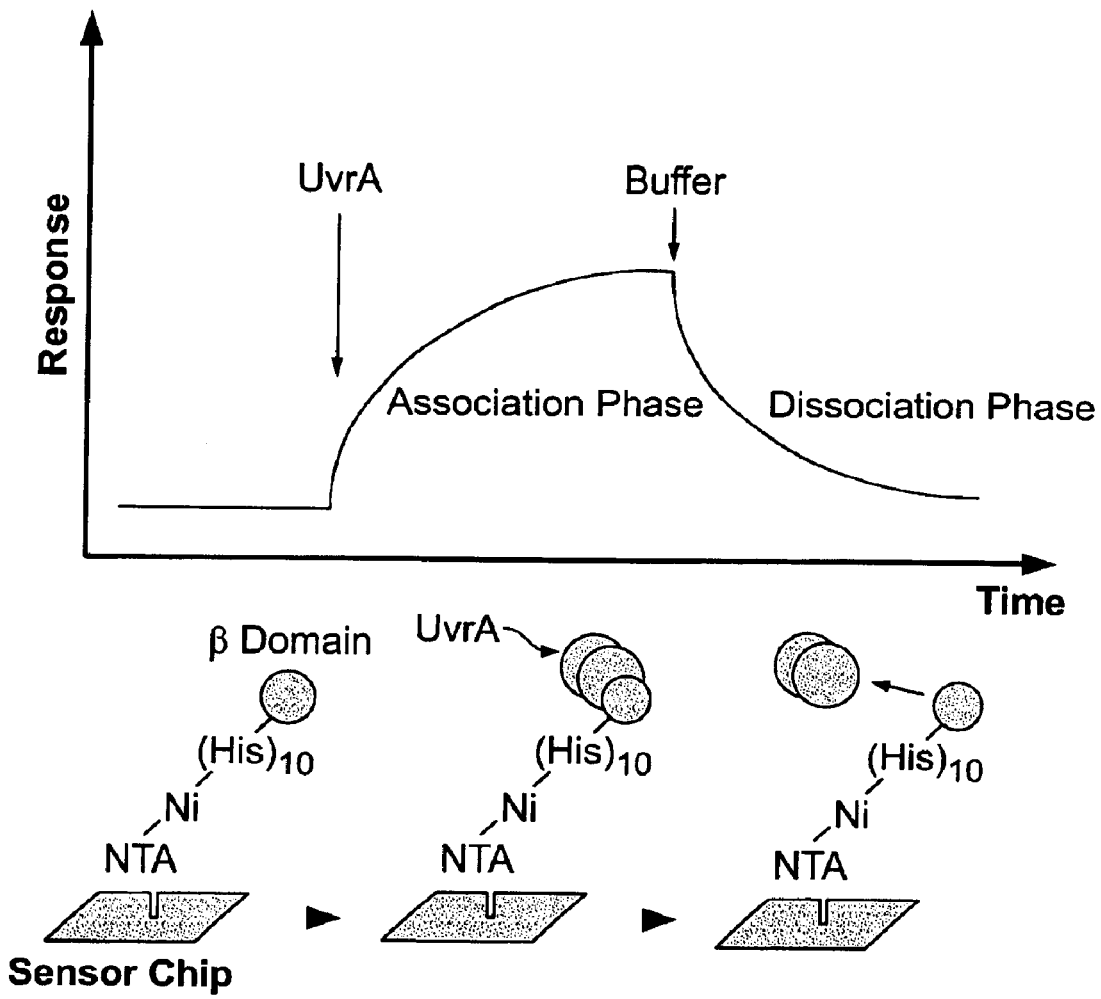
FIG. 38 shows the results of measurement of TRCF interactions using a BIAcore system.
Figure 39:
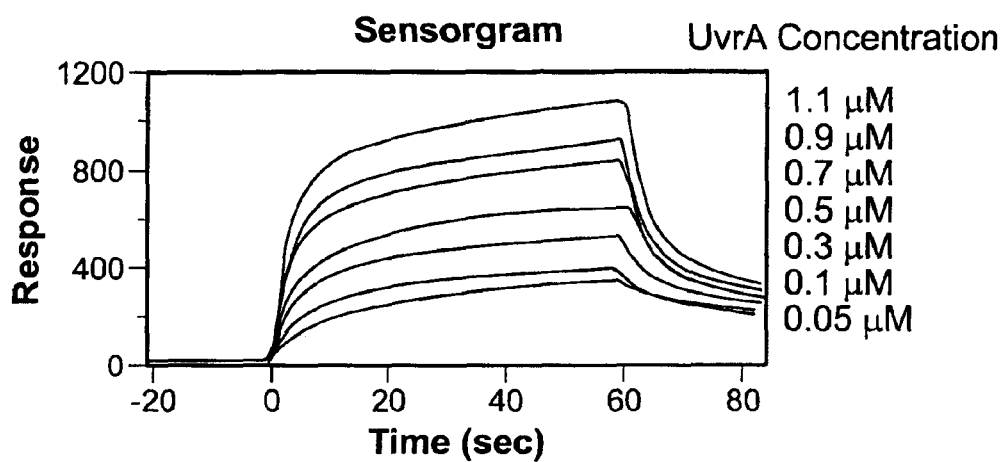
FIG. 39 shows the results of measurement of the interaction between TRCF and UvrA.

The results of analysis of the interaction between TRCF and UvrA using a BIACORE sensor chip revealed that TRCF binds to UvrA. The dissociation constant of this binding is 0.5 µM in the presence of ATP and 1.3 µM in the absence of ATP (FIGS. 38 and 39).

Example 2

Isolation and Characterization of DNA Repair Gene Sequences

The following example describes the isolation (cloning) and identification of the novel DNA Repair Enzyme gene sequences of the invention.

The genes of the invention encode the above-described DNA repair enzymes. These genes can be obtained by the cloning technique described below. Hereinbelow, the cloning of the genes of the invention will be described specifically.

The genes of the invention can be isolated from the genomic DNA of *Thermus thermophilus*, a highly thermophilic bacterium.

Example 3

Preparation of DNA Repair Enzyme Genomic DNA

The following example describes the preparation of DNA Repair Enzyme genomic DNA sequences of the invention.

Genomic DNA may be prepared from cells of the above-mentioned bacterium by conventional methods. For example, cells are disrupted in a guanidine-containing buffer followed by phenol extraction to obtain crude DNA fraction. This fraction is subjected to cesium chloride gradient ultracentrifugation to obtain purified genomic DNA. The thus obtained genomic DNA is digested with an appropriate restriction enzyme (e.g., EcoRI, BamHI, or Sau3AI). For ligation of DNA fragments, T4 DNA ligase is used, for example.

DNA fragments treated with the above-mentioned restriction enzyme are ligated to a vector that has been digested with the same restriction enzyme used in the above treatment (e.g., EcoRI or BamHI) or a restriction enzyme that will generate a cohesive end complimentary to the digestion site generated by the enzyme used in the above treatment (e.g., BamHI against Sau3AI). It is also possible to construct a library from the resultant vector. Prior to the ligation, DNA fragments of interest may be amplified by PCR or the like. As a vector, a phage or plasmid capable of autonomous replication in a host organism is used. Specific examples of phage vector include EMBL3, M13 and λgt11. Specific examples of plasmid vector include pET systems (pET-3a, etc.), pBR systems (pBR322, etc.), pUC systems (pUC18, etc.) and pBluescript II (Stratagene). Further, various shuttle vectors may also be used in addition to those vectors capable of autonomous replication in two or more host organisms such as *Escherichia coli* or *Bacillus subtilis*. For the ligation of the DNA fragments and the vector fragments, a known DNA ligase (e.g., T4 DNA ligase) is used. The DNA fragments and vector fragments are ligated after annealing. The resultant vector is transferred into a host microorganism. DNA transfer into a host microorganism may be performed using any of conventional methods. For example, when the host is *E. coli,* such method as electroporation or the calcium phosphate method may be used. When a phage DNA is introduced into *E. coli,* an in vitro packaging method using a kit (Gigapack II™; Stratagene) may be used, for example.

Subsequently, host cells surviving in a medium containing antibiotics are screened by colony hybridization, etc. Plasmids are recovered from the selected host cells by the alkali-SDS method or the like, to thereby obtain a genomic DNA fragment containing the gene of the invention.

The method of sequencing of the resultant DNA is not particularly limited. For example, a sequencing reaction may carried out using a PRISM™ sequencing kit containing a fluorescent dideoxyterminator (Perkin Elmer), followed by determination of the nucleotide sequence with an autosequencer from Applied Biosystems (e.g. Model ABI377).

In the present invention, MutY, RecJ, RecF and TRCF have been obtained as repair enzyme genes. SEQ ID NO: 1 shows the nucleotide sequence of the MutY gene of the invention, and SEQ ID NO: 2 shows the amino acid sequence encoded by this gene. SEQ ID NO: 3 shows the nucleotide sequence of the RecJ gene of the invention, and SEQ ID NO: 4 shows the amino acid sequence encoded by this gene. SEQ ID NO: 5 shows the nucleotide sequence of the RecF gene of the invention, and SEQ ID NO: 6 shows the amino acid sequence encoded by this gene. SEQ ID NO: 7 shows the nucleotide sequence of the TRCF gene of the invention, and SEQ ID NO: 8 shows the amino acid sequence encoded by this gene. It should be noted here that each of the above-mentioned amino acid sequences may have a mutation(s) such as deletion, substitution or addition of one or several amino acids, as long as a protein comprising that amino acid sequence retains DNA repair enzyme activity and is stable in a temperature range from 4° C. to between 15–300 mM, preferably 15–75 mM, and temperatures between 50–60° C., preferably 55–60° C.

Once the nucleotide sequence of the gene of the invention has been established, the gene of the invention can be obtained by chemical synthesis, by PCR using the cloned cDNA as a template, or by hybridization using a DNA fragment having the determined nucleotide sequence as a probe. Further, by using a technique such as site-specific mutagenesis, it is also possible to synthesize mutants of the gene of the invention that can express proteins with DNA repair enzyme activity.

TABLE 1

| Substrate DNA | A:G | | A:T | | | A:G O | | | A:C | | | A:G | | | G:G O | | |
|---|---|---|---|---|---|---|---|---|---|---|---|---|---|---|---|---|---|
| MutY | − | | + | | | + | | | + | | | + | | | + | | |
| NaOH treatment | + | − | − | + | + | − | − | + | + | − | − | + | + | − | − | + | + | − | − | + | + |
| Temperature (° C.) | 25 | 25 | 50 | 25 | 50 | 25 | 50 | 25 | 50 | 25 | 50 | 25 | 50 | 25 | 50 | 25 | 50 | 25 | 50 | 25 | 50 |
| Lane No. | 1 | 2 | 3 | 4 | 5 | 6 | 7 | 8 | 9 | 10 | 11 | 12 | 13 | 14 | 15 | 16 | 17 | 18 | 19 | 20 | 21 |

100° C., up to 95° C.; up to 90° C.; up to 80° C., and up to 75° C.

For example, 1–10 amino acids, preferably 1–5 amino acids, may be deleted from the amino acid sequence as shown in SEQ ID NO: 2, 4, 6 or 8; 1–10 amino acids, preferably 1–5 amino acids, may be added to the amino acid sequence as shown in SEQ ID NO: 2, 4, 6 or 8; or 1–10 amino acids, preferably 1–5 amino acids, may be replaced with other amino acids in the amino acid sequence as shown in SEQ ID NO: 2, 4, 6 or 8. By creating mutants having such deletion, addition or substitution, it is possible to obtain proteins that are thermally more stable.

The term "DNA repair enzyme activity" used herein means activity that can recognize various types of damage caused in DNA and mismatch sites resulting from such damage, remove damaged sites or mismatch sites and fill the resultant gaps. Specific examples of target damage for repair include damage caused by active oxygen, damage generated by UV irradiation, damage caused by chemical substances, and damage caused by PCR error.

The term "stability" used herein means that the structure of a protein as determined by CD spectrum analysis or the like is not changed up to 80° C., preferably up to 75° C., in a temperature range from 4° C. to 100° C.

Also, the gene of the present invention may comprise a complementary strand to a DNA comprising the nucleotide sequence as shown in SEQ ID NO: 1, 3, 5 or 7.

Further, the gene of the present invention may comprise a DNA that can hybridize under stringent conditions either with the DNA repair enzyme gene or with a complementary strand thereto of the invention is included in the gene of the invention. Further, the gene of the present invention may comprise a DNA which hybridizes under stringent conditions with a probe prepared either from the above-described DNA of the invention (SEQ ID NO: 1, 3, 5 or 7) or from a complementary strand thereto, and which encodes a protein having DNA repair enzyme activity. The term "probe" used herein refers to a probe having a complementary sequence to the full-length sequence or a partial sequence consisting of at least 17 consecutive bases of the nucleotide sequence as shown in SEQ ID NO: 1, 3, 5 or 7. The term "stringent conditions" used herein refers to sodium concentrations These results demonstrate that MutY detected these mismatches and cut the substrate DNAs at the mismatch sites with its N-glycosylase activity and AP lyase activity.

Example 4

Preparation of *Thermus thermophilus* HB8-Derived RecJ Gene Product

Using genomic DNA from *Thermus thermophilus* HB8 as a template, a PCR reaction was carried out in the same manner as in Example 1, except that the following primers were used.

(SEQ ID NO:11)
5' primer: 5'-ATCATATgAgAgACCgggTCCgCTggCgggT-3'

(SEQ ID NO:12)
3' primer: 5'-ATAgATCTTTACAggTCCACCgCCTggACCTC-3'

A vector pET-19b that had been digested with NdeI and BamHI and treated with a bacterial alkaline phosphatase for removal of its terminal phosphate group was ligated in a ligation reaction to the PCR product treated as described in Example 1 to thereby obtain a recombinant vector pET-19b-RecJ. Using this recombinant vector, *E. coli* BL21 (DE3) pLysE was transformed.

The nucleotide sequence of the gene encoding RecJ was determined in the same manner as in Example 1. As a result, the nucleotide sequence as shown in SEQ ID NO: 3 was obtained. The amino acid sequence encoded by this gene is shown in SEQ ID NO: 4.

The transformant prepared above was inoculated into 2 ml of LBamp medium and cultured at 37° C. for 16 hrs. The resultant culture broth was added to 1 L of LBamp medium and cultured at 37° C. for 3–4 hr. When cells reached the logarithmic phase, 50 μg/ml isopropyl-1-thio-β-D-galactoside (IPTG) was added thereto, followed by cultivation for 5–6 hr. The cells were harvested by centrifugation, washed with TE buffer and suspended in 20 ml of an adsorption buffer (20 mM Tris-HCl, 0.2 M NaCl, 5 mM imidazol and 1 mM 2-mercaptoethanol, pH 8.0), followed by sonication to disrupt cells. The resultant disrupted material was centrifuged at 10,000 g for 30 min to obtain a precipitate.

The thus obtained precipitate was dissolved in 6 M urea-containing adsorption buffer. Histidine-tagged RecJ protein in this solution was adsorbed onto chelating Sepharose. Briefly, the solution of the precipitate was added to chelating Sepharose that had been bound to Ni ions and washed sufficiently with 6 M urea-containing adsorption buffer. The resultant mixture was incubated at 4° C. for 1 hr. Then, the Sepharose carrier was recovered by centrifugation and washed sufficiently with the adsorption buffer. Subsequently, the Sepharose carrier was washed with adsorption buffers of gradually lowered urea concentrations (i.e., 4 M, 3 M, 2 M and 1 M) to thereby refold His-tagged RecJ protein. The RecJ protein was eluted with an elution buffer (20 mM Tris-HCl, 0.5 M NaCl, 500 mM imidazol, 1 mM 2-mercaptoethanol, pH 8.0). The purity of this His-tagged RecJ protein was confirmed by 12.5% SDS-polyacrylamide gel electrophoresis (FIG. 13). In FIG. 13, individual lanes are as follows:

M: molecular weight marker

Lane 1: total cell lysate

Lane 2: cell lysate (supernatant)

Lane 3: cell lysate (pellet)

Lane 4: chromatography fraction (Ni-NTA column)

Lane 5: refolding

Lane 6: anion exchange chromatography fraction (MonoQ column)

The bands indicated by an arrowhead represent His-tagged RecJ protein [(His)$_{10}$-RecJ].

Purified His-tagged RecJ protein was partially degraded with 100 units of thermolysin (Sigma) at 25° C. for 6 hr to thereby obtain a soluble core domain with a molecular weight of 45 kDa.

Example 5

Physicochemical Properties of *Thermus thermophilus* HB8-Derived RecJ Protein (1) CD Spectrum CD spectrum was measured on 1.6 μM RecJ in a solution containing 50 mM potassium phosphate, 100 mM KCl, 0.1 mM DTE and 0.1 mM EDTA (pH 7.2). The results are shown in FIG. 15. From this Figure, it was found that the α-helix content of RecJ is ~50%.

(2) Thermostability Test

Thermostability was examined by analyzing the CD spectrum of the core domain obtained in Example 4 (1.6 μM) in a buffer containing 100 mM KCl, 0.1 mM dithiothreitol, 0.1 mM EDTA and 50 mM potassium phosphate (pH 7.5) while varying temperatures. As a result, it was found that the core domain of RecJ protein is stable at temperatures from 15° C. to 60° C. (FIG. 16).

Example 6

Figure 17:
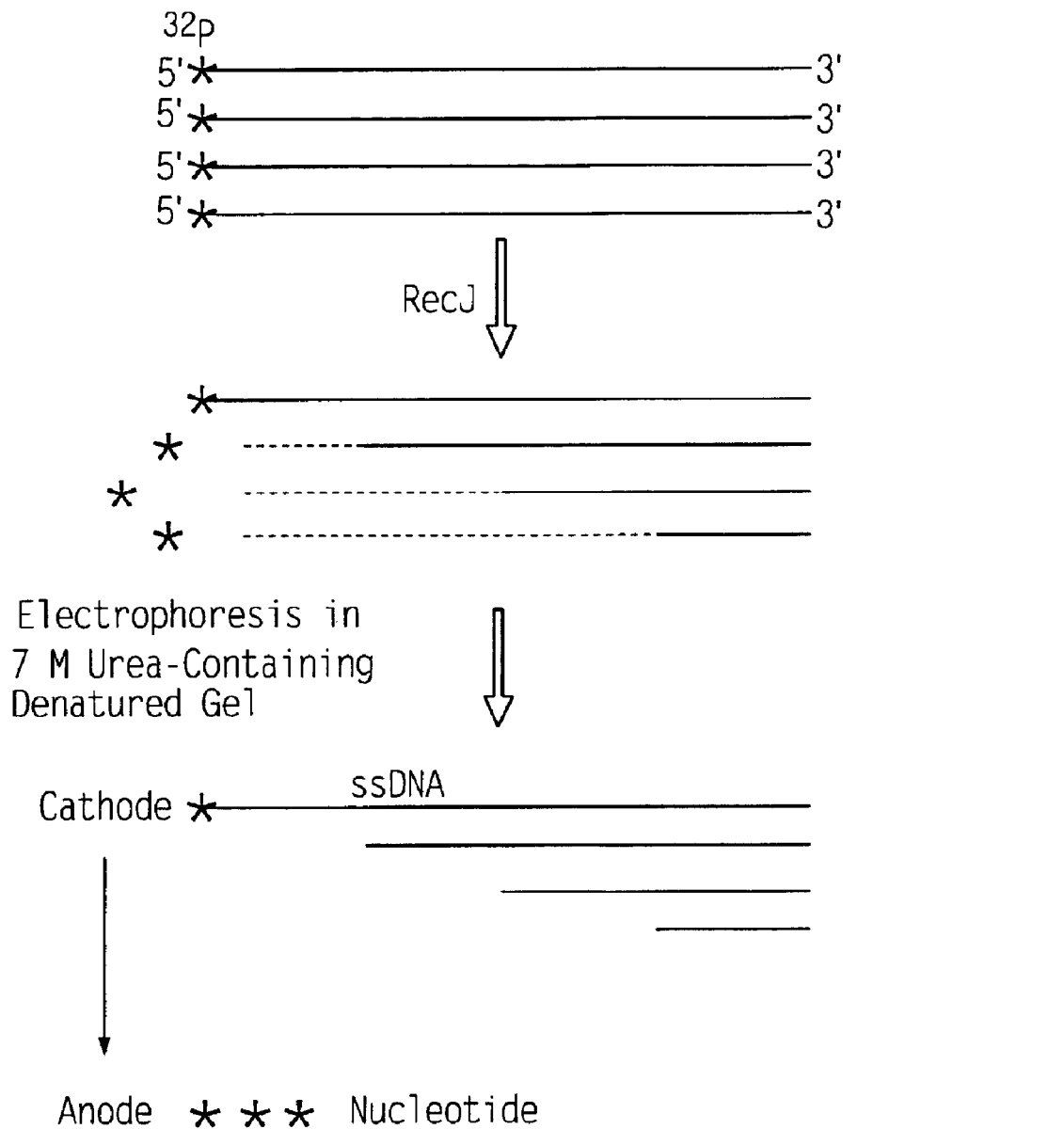
FIG. 17 is a diagram showing the method of measurement of the exonuclease activity of RecJ (also shown is SEQ ID NO:57).

Measurement of the Exonuclease Activity of *Thermus thermophilus* HB8-Derived RecJ Protein The His-tagged RecJ protein obtained in Example 4 was degraded with thrombin to remove the tag. To a reaction solution (20 mM Tris-HCl, 10 mM MgCl$_2$, 100 mM KCl, 1 mM DTT, pH 7.5) containing 0.1 mM tag-removed RecJ protein, a single-stranded DNA of 49-mer (as shown below) whose 5' end had been labeled with a radioactive phosphate group was added as a substrate and reacted at 25° C., 37° C. or 50° C. (FIG. 17).

Single-stranded DNA:
5'-ACTACTTggTACACTgACgCgAgCACgCAggAg CTCATTCCAgTgCGCA-3' (SEQ ID NO: 13)

The reaction products were analyzed by polyacrylamide gel electrophoresis. The results confirmed decrease of the substrate and increase of liberated, radioactive phosphate-labeled nucleotides with the passage of time. The results also indicated that RecJ protein has 5' to 3' exonuclease activity (FIG. 18).

Figure 18A:
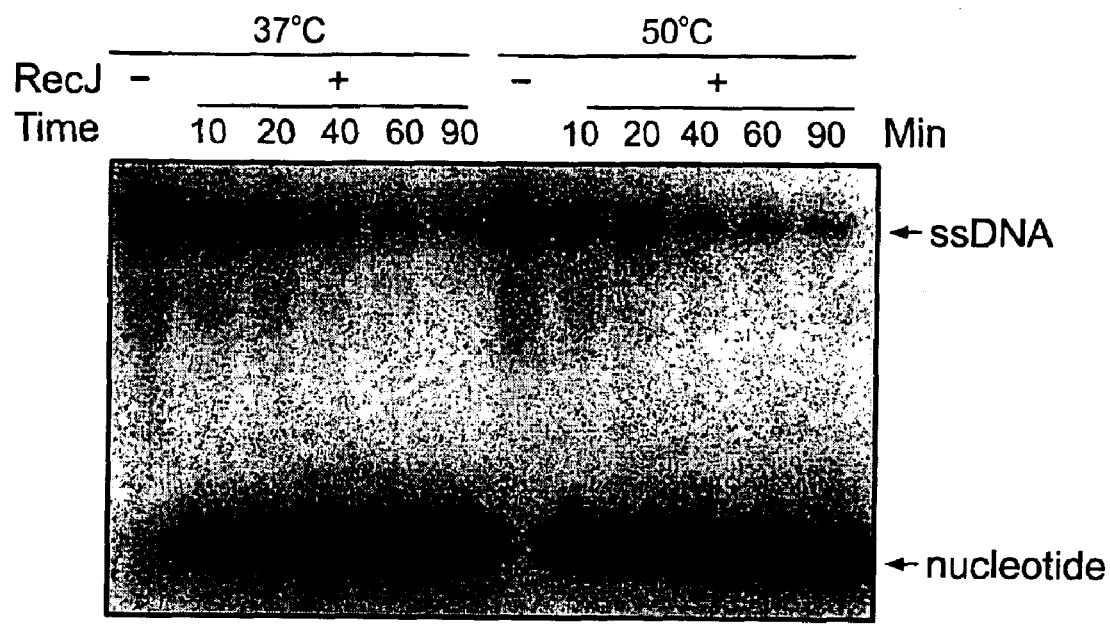
FIG. 18 shows results of measurement of the exonuclease activity of RecJ.
Figure 18B:
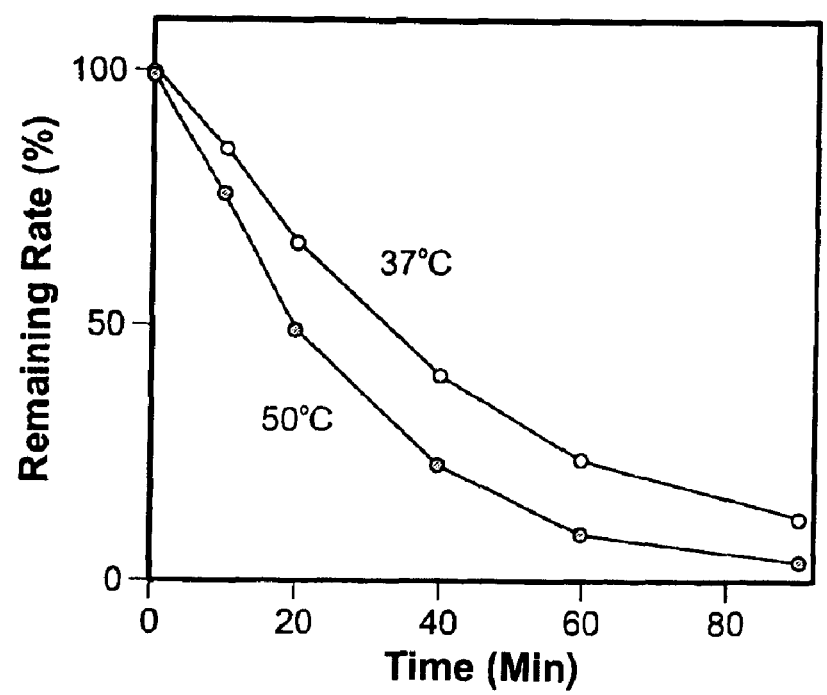
Figure 19:
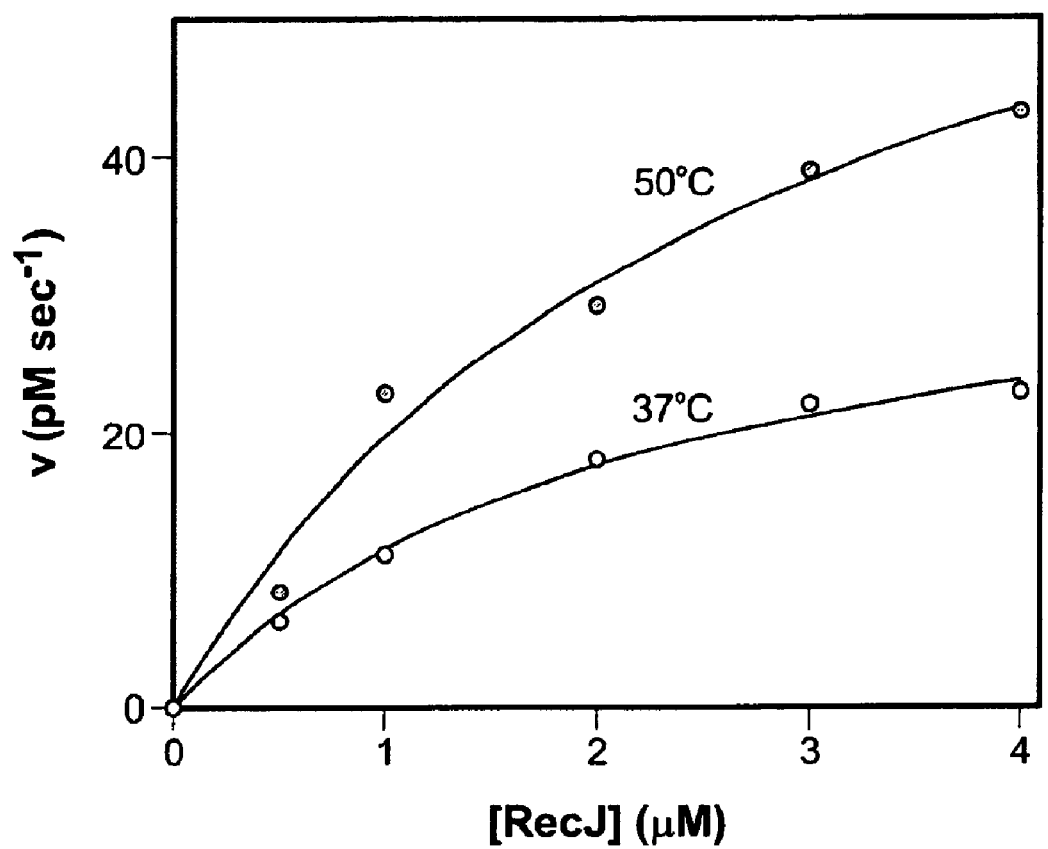
FIG. 19 shows results of measurement of the exonuclease activity of RecJ (dependency on RecJ concentration).

FIG. 18 shows the 5' to 3' exonuclease activity of RecJ. FIG. 19 shows the dependency on RecJ concentration of the exonuclease activity. The exonuclease activity of RecJ increased depending on the RecJ concentration. Also, the activity increased further at a high temperature (50° C.).

Figure 20:
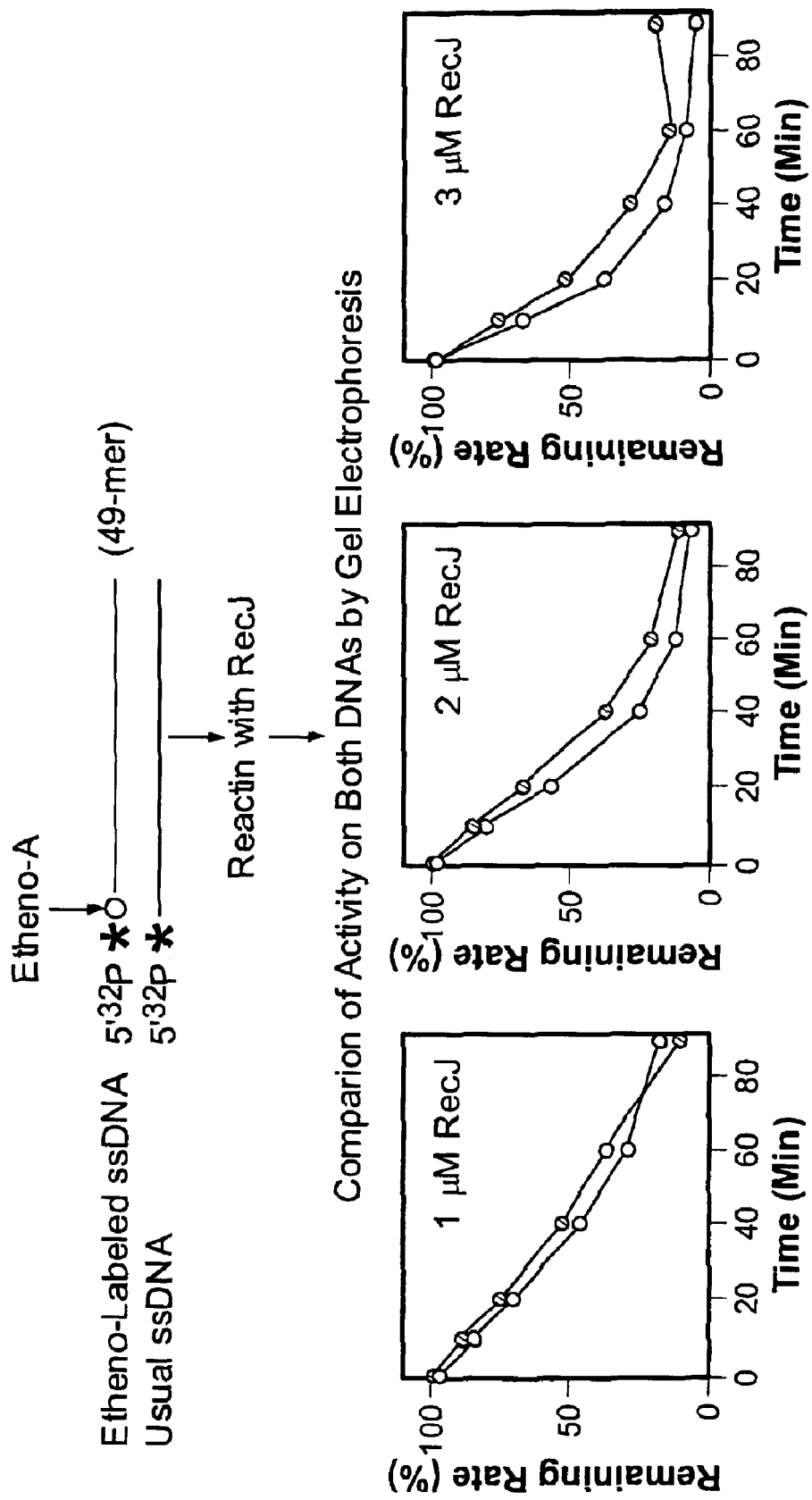
FIG. 20 shows the effect of etheno-nucleotide upon RecJ activity.

FIG. 20 shows the results of examination of the effect of etheno-nucleotide upon RecJ exonuclease activity. Etheno-nucleotide is a fluorescently labeled nucleotide, which is characterized by emitting more intense fluorescence when it is liberated from DNA than when integrated in DNA. Thus, it is possible to know whether etheno-nucleotide has been liberated or not, i.e., whether DNA has been degraded or not, by measuring its fluorescence intensity. The RecJ exonuclease activity on etheno-nucleotide-labeled DNA and that on usual DNA were almost comparable. Thus, it was found that etheno-nucleotide-labeled DNA can be a substrate for RecJ.

Figure 21:
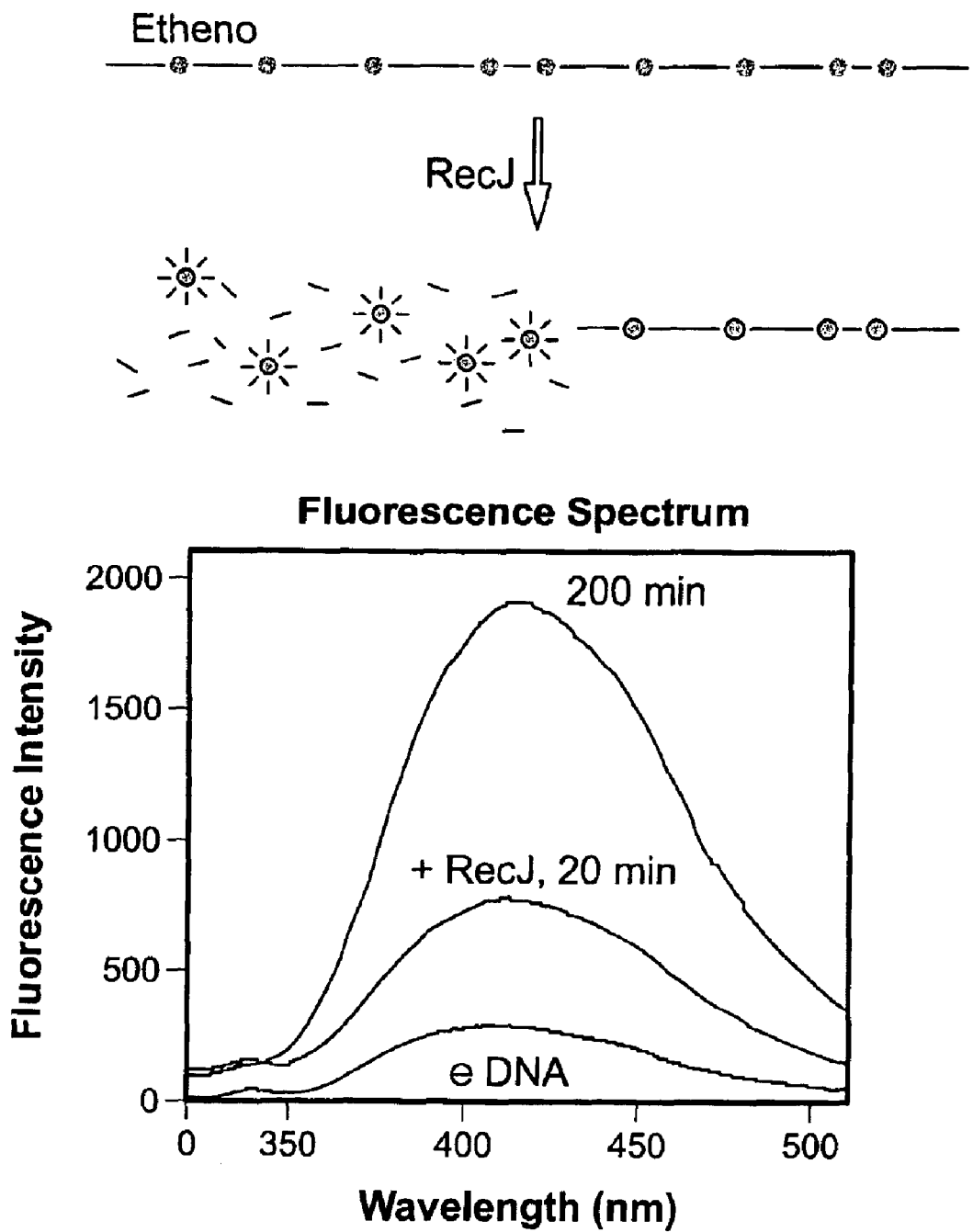
FIG. 21 shows results of measurement of the exonuclease activity of RecJ (fluorescence spectrum).

Subsequently, a reaction solution containing 32 μM etheno-nucleotide (εDNA), 0.4 μM RecJ, 20 mM Tris-HCl, 10 mM MgCl$_2$ and 100 mM KCl (pH 7.5) was incubated at 37° C., followed by detection of fluorescence with an excitation wavelength of 305 nm. The results are shown in FIG. 21 (lower panel titled "Fluorescent Spectrum"). Liberation of the etheno-nucleotide from DNA by the exonuclease activity of RecJ increased fluorescence intensity.

Further, a reaction solution containing 32 μM etheno-nucleotide (εDNA), 0.4 μM RecJ, 20 mM Tris-HCl, 10 mM MgCl$_2$ and 100 mM KCl (pH 7.5) was incubated at 37° C., followed by measurement of the time course of fluorescence intensity and the degree of fluorescence polarization with an excitation wavelength of 305 nm and a fluorescence wavelength of 410 nm.

Figure 22A:
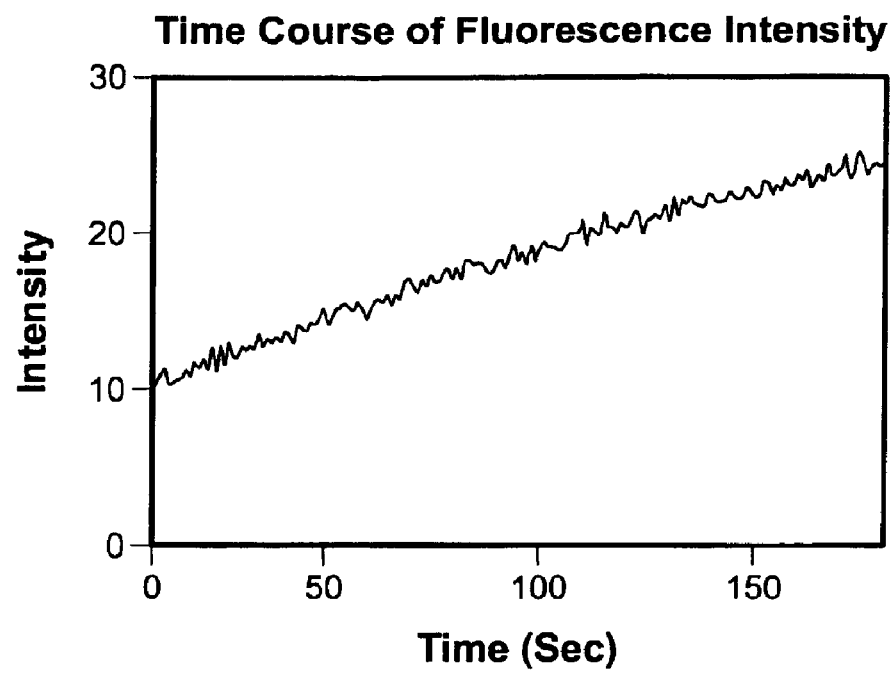
FIG. 22 shows the results of measurement of the exonuclease activity of RecJ (time course of fluorescence intensity and the degree of fluorescence polarization).
Figure 22B:
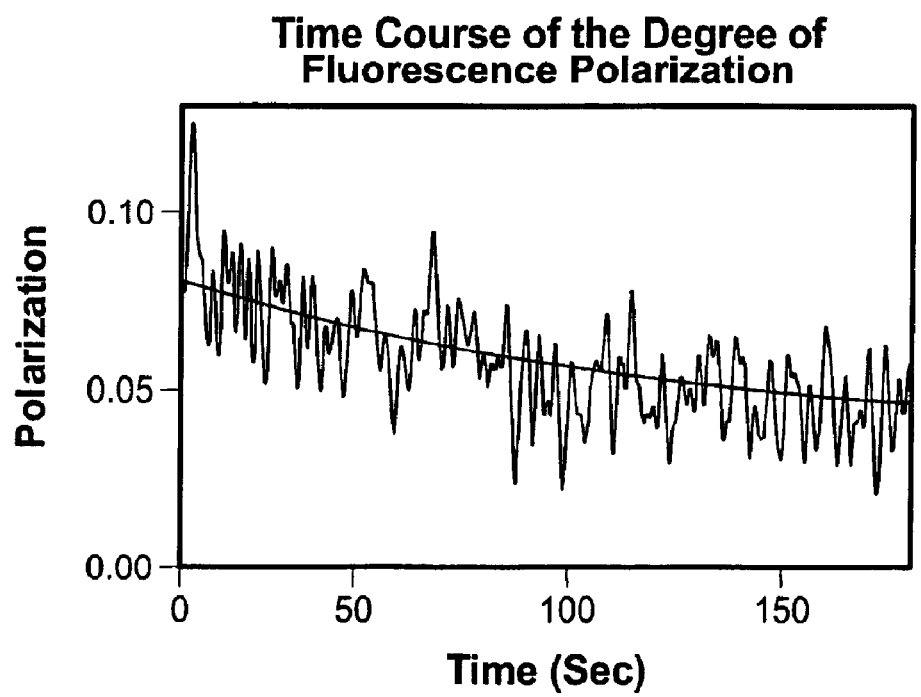

The results are shown in FIG. 22. The upper panel shows the time course of fluorescence intensity, and the lower panel the time course of the degree of fluorescence polarization. When RecJ was reacted with etheno-nucleotide, the degree of fluorescence polarization that indicates the degree of freedom of fluorescent material increased. It is believed that this fact demonstrates the liberalization of the etheno-nucleotide from DNA.

Further, a reaction solution containing 0.1 μM RecJ, 20 mM Tris-HCl, 10 mM MgCl$_2$ and 100 mM KCl (pH 7.5) was incubated at 37° C., followed by detection of fluorescence with an excitation wavelength of 305 nm and a fluorescence wavelength of 410 nm and measurement of the dependency of exonuclease activity upon DNA concentration.

Figure 23:
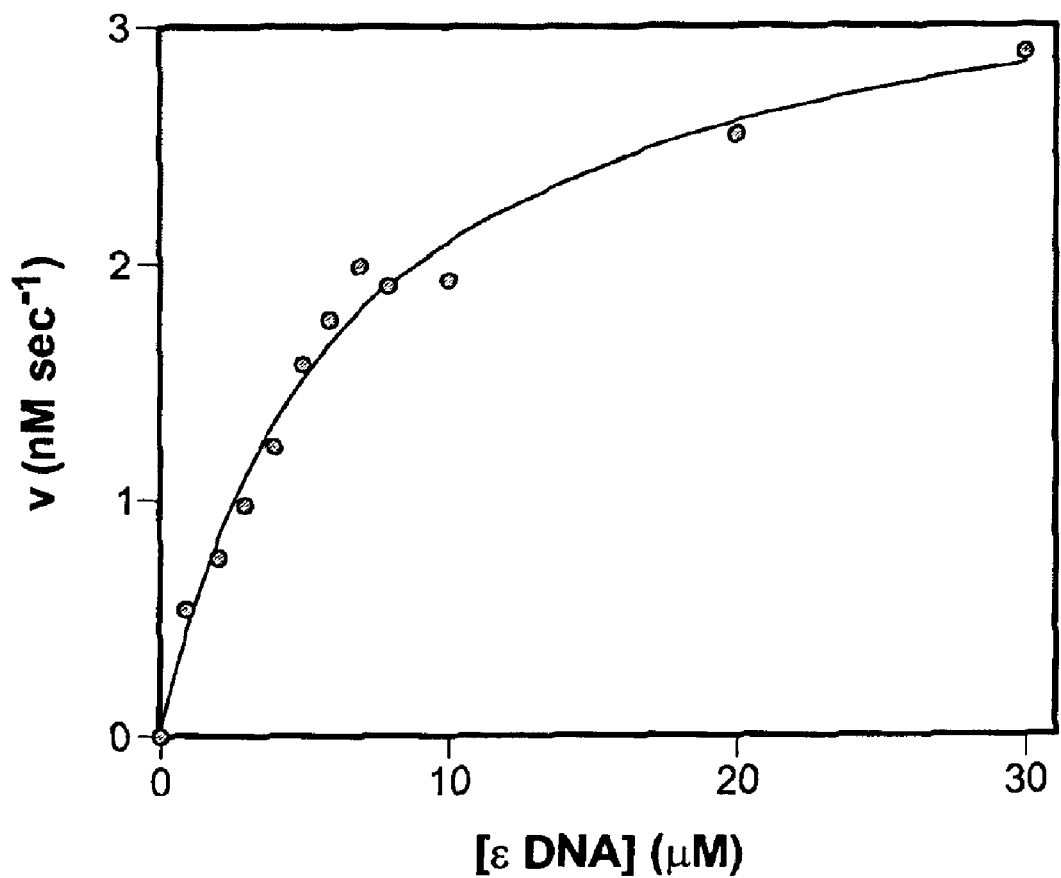
FIG. 23 shows results of measurement of the exonuclease activity of RecJ (dependency on DNA concentration).

The results are shown in FIG. 23. The results of calculation of kinetic parameters according to Michaelis-Menten equation were as follows: $k_{cat}$=0.034/sec and $K_m$=6.2 μM.

Example 7

Preparation of *Thermus thermophilus* HB8-Derived RecF Gene Product

Using genomic DNA from *Thermus thermophilus* HB8 as a template, a PCR reaction was carried out in the same manner as in Example 1, except that the following primers were used.

```
5' primer: 5'-ATATCATATgCgTCTTCTCCTCTTCCggCAACggAACT-3'    (SEQ ID NO:14)

3' primer: 5'-ATATAgATCTTTATTAggCgCCAgggCACAggACCACCCCT-3' (SEQ ID NO:15)
```

A vector pET-15b that had been digested with NdeI and BamHI and treated with a bacterial alkaline phosphatase for removal of its terminal phosphate group was ligated in a ligation reaction to the PCR product treated as described in Example 1 to thereby obtain a recombinant vector pET-15b-RecF. Using this recombinant vector, E. coli BL21 (DE3) pLysE was transformed.

The nucleotide sequence of the gene encoding RecF was determined in the same manner as in Example 1. As a result, the nucleotide sequence as shown in SEQ ID NO: 5 was obtained. The amino acid sequence encoded by this gene is shown in SEQ ID NO: 6.

The transformant prepared above was inoculated into 2 ml of LBamp medium and cultured at 37° C. for 16 hrs. The resultant culture broth was added to 1 L of LBamp medium and cultured at 37° C. for 3–4 hr. When cells reached the logarithmic phase, 50 μg/ml isopropyl-1-thio-β-D-galactoside (IPTG) was added thereto, followed by cultivation for 5–6 hr. The cells were harvested by centrifugation, washed with TE buffer and suspended in 20 ml of an adsorption buffer (20 mM Tris-HCl, 0.2 M NaCl, 5 mM imidazol and 1 mM 2-mercaptoethanol, pH 8.0), followed by sonication to disrupt cells. The resultant disrupted material was centrifuged at 10,000 g for 30 min to obtain a supernatant.

His-tagged RecF protein in the resultant supernatant was adsorbed onto a chelating Sepharose column. Briefly, the supernatant was applied to a chelating Sepharose column that had been bound with Ni ions and equilibrated with the adsorption buffer. Then, the column was washed with the adsorption buffer. Subsequently, His-tagged RecF protein was eluted with an elution buffer (20 mM Tris-HCl, 0.2 M NaCl, 500 mM imidazol, 1 mM 2-mercaptoethanol, pH 8.0). The purity of this His-tagged RecF protein was confirmed by 12.5% SDS-polyacrylamide gel electrophoresis (FIG. 25).

In FIG. 25, individual lanes are as follows:

M: molecular weight marker

T: total cell lysate

S: cell lysate (supernatant)

His: histidine-tagged protein

HA: hydroxy apatite column chromatography fraction

Example 8

Physicochemical Properties of RecF (1) CD Spectrum

CD spectrum was measured on 1.4 μM RecF in a solution containing 50 mM Tris-HCl and 100 mM KCl (pH 7.5). The results revealed that the α-helix content of RecF is ~40%.

(2) Thermostability Test

Thermostability was examined by analyzing CD spectrum in a solution containing 50 mM Tris-HCl and 100 mM KCl (pH 7.5) while varying temperatures.

The results revealed that RecF is stable up to 50° C.

(3) Analysis of Binding Action

Figure 28A:
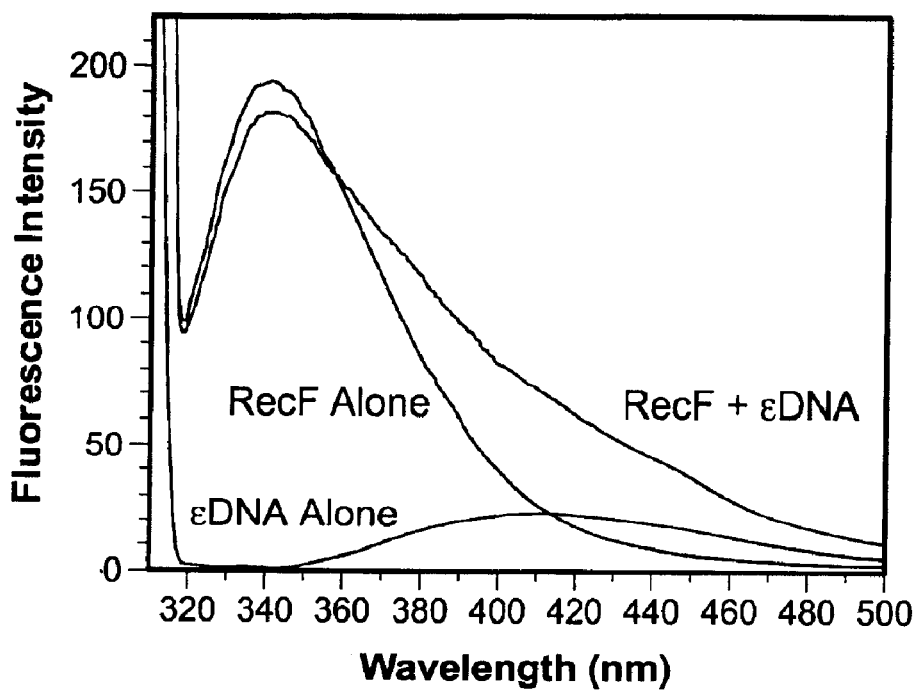
FIG. 28 presents graphs showing the linking of RecF to εDNA.
Figure 28B:
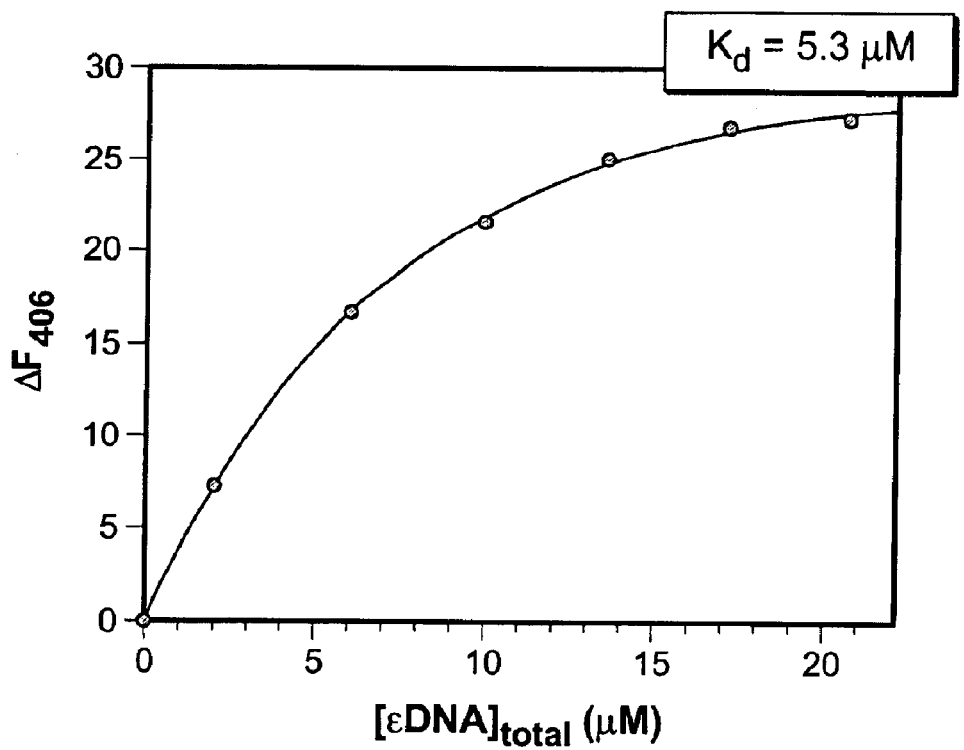

A reaction solution containing 5 μM RecF, 50 mM Tris-HCl, 100 mM KCl, 0.1 mM EDTA, and 5 mM 2-mercaptoethanol (pH 7.5) was incubated with εDNA at 25° C., followed by analysis of fluorescence spectrum with an excitation wavelength of 310 nm. Since changes were observed in the spectrum of RecF in the presence of εDNA, it was found that RecF binds to DNA. The dissociation constant was 5.3 μM (FIG. 28).

(4) ATPase Activity

A reaction solution containing 1 μM RecF, 50 mM Tris-HCl (pH 7.5), 10 mM magnesium acetate, 100 mM KCl, 2 mM phosphoenolpyruvic acid, 0.3 mM NADH, 1 mM DTE, 25 U of pyruvate kinase and 25 U of lactate dehydrogenase was incubated, followed by measurement of ATPase activity. As a result, it was found that RecF, even alone, has ATPase activity and that this activity increases when the temperature is raised from 25° C. to 37° C. (FIG. 29).

Further, a reaction solution containing 1 μM RecF, 50 mM Tris-HCl (pH 7.5), 6 μM poly(dT) or 6 μM poly(dA) poly(dT), 10 mM magnesium acetate, 100 mM KCl, 2 mM phosphoenolpyruvic acid, 0.3 mM NADH, 1 mM DTE, 25 U of pyruvate kinase and 25 U of lactate dehydrogenase was incubated at 25° C., followed by measurement of ATPase activity. The results revealed that ATPase activity increases in the presence of single-stranded DNA (poly(dT)) and decreases in the presence of double-stranded DNA (poly(dA) poly(dT)) (FIG. 30).

Example 9

Preparation of *Thermus thermophilus* HB8-Derived TRCF (Transcription-Repair Coupling Factor) Gene Product Using genomic DNA from *Thermus thermophilus* HB8 as a template, a PCR reaction was carried out in the same manner as in Example 1, except that the following primers were used.

```
5' primer: 5'-ATATCATATggAAATCgCgCTAgAgAggATCTACggCC-3'    (SEQ ID NO: 16)

3' primer: 5'-ATATAgATCTTTATTAGAGGTCGGCGAAGAGGTAGAGCACC-3' (SEQ ID NO: 17)
```

A vector pET-15b that had been digested with NdeI and BamHI and treated with a bacterial alkaline phosphatase for removal of its terminal phosphate group was ligated in a ligation reaction to the PCR product treated as described in Example 1 to thereby obtain a recombinant vector pET-15b-TRCF. Using this recombinant vector, E. coli BL21 (DE3) pLysE was transformed.

The nucleotide sequence of the gene encoding TRCF was determined in the same manner as in Example 1. As a result, the nucleotide sequence as shown in SEQ ID NO: 7 was obtained. The amino acid sequence encoded by this gene is shown in SEQ ID NO: 8.

The transformant prepared above was inoculated into 2 ml of LBamp medium and cultured at 37° C. for 16 hrs. The resultant culture broth was added to 1 L of LBamp medium and cultured at 37° C. for 3–4 hr. When cells reached the logarithmic phase, 50 μg/ml isopropyl-1-thio-β-D-galactoside (IPTG) was added thereto, followed by cultivation for 5–6 hr. The cells were harvested by centrifugation, washed with TE buffer and suspended in 20 ml of an adsorption buffer (20 mM Tris-HCl, 0.2 M NaCl, 5 mM imidazol and 1 mM 2-mercaptoethanol, pH 8.0), followed by sonication to disrupt cells. The resultant disrupted material was centrifuged at 10,000 g for 30 min to obtain a supernatant.

His-tagged TRCF protein in the resultant supernatant was adsorbed onto a chelating Sepharose column. Briefly, the supernatant was applied to a chelating Sepharose column that had been bound with Ni ions and equilibrated with the adsorption buffer. Then, the column was washed with the adsorption buffer. Subsequently, His-tagged TRCF protein was eluted with an elution buffer (20 mM Tris-HCl, 0.2 M NaCl, 500 mM imidazol, 1 mM 2-mercaptoethanol, pH 8.0). The purity of this His-tagged TRCF protein was confirmed by 12.5% SDS-polyacrylamide gel electrophoresis (FIG. 33). In FIG. 33, the upper panel shows the results of purification of UvrB-β, and the lower panel shows the results of purification of TRCF-β. The lanes in the upper panel are as follows: M: molecular weight marker; 1: total cell lysate; 2: cell lysate (supernatant from centrifugation); 3: nickel column chromatography fraction; 4: butyl column chromatography fraction. The lanes in the lower panel are as follows: M: molecular weight marker; 1: total cell lysate; 2: nickel column & butyl column chromatography fraction.

Example 10

Physicochemical Properties of TRCF (1) CD Spectrum

CD spectrum was measured on UvrB-β and TRCF-β at 25° C. in a solution containing 50 mM Tris-HCl and 100 mM KCl (pH 7.9). The results are shown in FIG. 35. It was found that UvrB-β and TRCF-β have similar three-dimensional structures.

(2) Thermostability Test

Thermostability was examined by analyzing the CD spectra of UvrB-β and TRCF-β in a solution containing 50 mM Tris-HCl and 100 mM KCl (pH 7.9) while varying temperatures. The results revealed that both UvrB-β and TRCF-β are stable at temperatures from 20° C. to 75° C. at pH 7.9 (FIG. 36).

(3) pH Stability

The CD spectra of UvrB-β and TRCF-β, were measured in various buffers containing 100 mM KCl and having different pH values.

The results revealed that TRCF-β is stable at pH 4 to 9 at 25° C. (FIG. 37).

(4) Analysis of Binding Action $NiCl_2$ was injected to a sensor chip NTA. Then, β domain was injected thereto and immobilized. Since it is known that UvrA and UvrB interact with each other only in the presence of ATP, the interaction between each β domain and UvrA was measured both in the presence of ATP and in the absence of ATP (FIG. 38).

As a result, it was found that the dissociation constant ($K_d$) is 0.5 μM in the presence of ATP and 1.3 μM in the absence of ATP (FIG. 39).

EFFECT OF THE INVENTION

According to the present invention, DNA repair enzymes and genes encoding the same are provided. The enzymes of the invention have DNA repair activity and are excellent in thermostability. Therefore, they are useful as reagents for researches in molecular biology and other fields or as reagents for preventing or repairing errors in various DNA synthesis reactions.

Sequence Listing Free Text

SEQ ID NO: 9: synthetic DNA
SEQ ID NO: 10: synthetic DNA
SEQ ID NO: 11: synthetic DNA
SEQ ID NO: 12: synthetic DNA
SEQ ID NO: 13: synthetic DNA
SEQ ID NO: 14: synthetic DNA
SEQ ID NO: 15: synthetic DNA
SEQ ID NO: 16: synthetic DNA
SEQ ID NO: 17: synthetic DNA

What is claimed is:

1. An isolated protein comprising the amino acid sequence as set forth in SEQ ID NO: 2.

2. An isolated protein consisting of the amino acid sequence as set forth in SEQ ID NO: 2.

3. A fusion protein comprising the amino acid sequence as set forth in SEQ ID NO: 2, and a second heterologous sequence.

* * * * *

SEQUENCE LISTING

```
<160> NUMBER OF SEQ ID NOS: 65

<210> SEQ ID NO 1
<211> LENGTH: 975
<212> TYPE: DNA
<213> ORGANISM: Thermus thermophilus
<220> FEATURE:
<221> NAME/KEY: CDS
<222> LOCATION: (1)..(975)

<400> SEQUENCE: 1 atg gag gcc tgg cgg aaa gcc ctc ctc gcc tgg tac cgg gaa aac gcc      48
Met Glu Ala Trp Arg Lys Ala Leu Leu Ala Trp Tyr Arg Glu Asn Ala
1               5                   10                  15 cgc ccc ctc ccc tgg cgg ggg gag aag gac cct tac cgc gtc ctg gtc      96
```

```
                                                       -continued

Arg Pro Leu Pro Trp Arg Gly Glu Lys Asp Pro Tyr Arg Val Leu Val
            20                  25                  30 tcc gag gtc ctt ctg cag cag acc cgg gtg gag cag gcc ctc ccc tat        144
Ser Glu Val Leu Leu Gln Gln Thr Arg Val Glu Gln Ala Leu Pro Tyr
            35                  40                  45 tac cgc cgc ttt ctg gag cgc ttt ccc acc ctg aag gcc ctg gcc gcg        192
Tyr Arg Arg Phe Leu Glu Arg Phe Pro Thr Leu Lys Ala Leu Ala Ala
 50                  55                  60 gct tcc ctg gaa gag gtc ctt agg gtc tgg cag ggg gcg ggc tac tac        240
Ala Ser Leu Glu Glu Val Leu Arg Val Trp Gln Gly Ala Gly Tyr Tyr
 65                  70                  75                  80 cgg cgg gcg gaa cac ctc cac cgc ctg gcc cga agc gtg gag gag ctt        288
Arg Arg Ala Glu His Leu His Arg Leu Ala Arg Ser Val Glu Glu Leu
                85                  90                  95 ccc ccg agc ttc gcc gag ctt cgg ggg ctt cct ggt ctc ggg cct tac        336
Pro Pro Ser Phe Ala Glu Leu Arg Gly Leu Pro Gly Leu Gly Pro Tyr
               100                 105                 110 acc gcg gcg gcg gtg gcc tcc atc gcc ttc ggg gag cgg gtg gcg gcg        384
Thr Ala Ala Ala Val Ala Ser Ile Ala Phe Gly Glu Arg Val Ala Ala
           115                 120                 125 gtg gac ggg aac gtc cgg agg gtc ctc tcc cgc ctc ttc gcc cgg gaa        432
Val Asp Gly Asn Val Arg Arg Val Leu Ser Arg Leu Phe Ala Arg Glu
130                 135                 140 agc ccc aag gag aag gag ctt ttc gcc ctc gcc cag ggc ctc ctc ccc        480
Ser Pro Lys Glu Lys Glu Leu Phe Ala Leu Ala Gln Gly Leu Leu Pro
145                 150                 155                 160 gag ggc gtg gac ccg ggg gtg tgg aac cag gcc ctc atg gag ctc ggg        528
Glu Gly Val Asp Pro Gly Val Trp Asn Gln Ala Leu Met Glu Leu Gly
                165                 170                 175 gcc acg gtc tgc ctg ccg aaa cgg ccc cgt tgc ggg gcc tgc ccc cta        576
Ala Thr Val Cys Leu Pro Lys Arg Pro Arg Cys Gly Ala Cys Pro Leu
            180                 185                 190 ggg gcc ttc tgc cgg ggg aag gag gcc ccc ggg cgc tac ccc gcg ccc        624
Gly Ala Phe Cys Arg Gly Lys Glu Ala Pro Gly Arg Tyr Pro Ala Pro
        195                 200                 205 agg aag cgc cgg gcg aag gag gag cgc ctc gtc gcc ctc gtc ctc ctc        672
Arg Lys Arg Arg Ala Lys Glu Glu Arg Leu Val Ala Leu Val Leu Leu
210                 215                 220 ggg cgg aag ggg gtg cac ctg gaa agg ctt gag ggg cgc ttc cag ggc        720
Gly Arg Lys Gly Val His Leu Glu Arg Leu Glu Gly Arg Phe Gln Gly
225                 230                 235                 240 ctc tac ggc gtc ccc ctc ttt ccc cct gag gag ctt ccc ggg cgg gag        768
Leu Tyr Gly Val Pro Leu Phe Pro Pro Glu Glu Leu Pro Gly Arg Glu
                245                 250                 255 gcg gcc ttc ggg gtg agg tct agg ccc cta ggc gag gtg cgc cac gcc        816
Ala Ala Phe Gly Val Arg Ser Arg Pro Leu Gly Glu Val Arg His Ala
            260                 265                 270 ctc acc cac cgg agg ctt cgc gtg gag gtg cgg ggg gcc ctt tgg gaa        864
Leu Thr His Arg Arg Leu Arg Val Glu Val Arg Gly Ala Leu Trp Glu
        275                 280                 285 ggg gag ggg gag gac ccc tgg aag agg ccc cta ccc aag ctc atg gag        912
Gly Glu Gly Glu Asp Pro Trp Lys Arg Pro Leu Pro Lys Leu Met Glu
290                 295                 300 aag gtg ctc cgc aag gcg ctt ccc ctc ctc gct cat gcg ggc gta gtc        960
Lys Val Leu Arg Lys Ala Leu Pro Leu Leu Ala His Ala Gly Val Val
305                 310                 315                 320 ccc ctc ccg gac gca                                                    975
Pro Leu Pro Asp Ala
                325
```

<210> SEQ ID NO 2
<211> LENGTH: 325
<212> TYPE: PRT
<213> ORGANISM: Thermus thermophilus

<400> SEQUENCE: 2

Met Glu Ala Trp Arg Lys Ala Leu Leu Ala Trp Tyr Arg Glu Asn Ala
1               5                   10                  15

Arg Pro Leu Pro Trp Arg Gly Glu Lys Asp Pro Tyr Arg Val Leu Val
            20                  25                  30

Ser Glu Val Leu Leu Gln Gln Thr Arg Val Glu Gln Ala Leu Pro Tyr
        35                  40                  45

Tyr Arg Arg Phe Leu Glu Arg Phe Pro Thr Leu Lys Ala Leu Ala Ala
    50                  55                  60

Ala Ser Leu Glu Glu Val Leu Arg Val Trp Gln Gly Ala Gly Tyr Tyr
65                  70                  75                  80

Arg Arg Ala Glu His Leu His Arg Leu Ala Arg Ser Val Glu Glu Leu
                85                  90                  95

Pro Pro Ser Phe Ala Glu Leu Arg Gly Leu Pro Gly Leu Gly Pro Tyr
            100                 105                 110

Thr Ala Ala Val Ala Ser Ile Ala Phe Gly Glu Arg Val Ala Ala
        115                 120                 125

Val Asp Gly Asn Val Arg Arg Val Leu Ser Arg Leu Phe Ala Arg Glu
130                 135                 140

Ser Pro Lys Glu Lys Glu Leu Phe Ala Leu Ala Gln Gly Leu Leu Pro
145                 150                 155                 160

Glu Gly Val Asp Pro Gly Val Trp Asn Gln Ala Leu Met Glu Leu Gly
                165                 170                 175

Ala Thr Val Cys Leu Pro Lys Arg Pro Arg Cys Gly Ala Cys Pro Leu
            180                 185                 190

Gly Ala Phe Cys Arg Gly Lys Glu Ala Pro Gly Arg Tyr Pro Ala Pro
        195                 200                 205

Arg Lys Arg Arg Ala Lys Glu Glu Arg Leu Val Ala Leu Val Leu Leu
210                 215                 220

Gly Arg Lys Gly Val His Leu Glu Arg Leu Glu Gly Arg Phe Gln Gly
225                 230                 235                 240

Leu Tyr Gly Val Pro Leu Phe Pro Pro Glu Glu Leu Pro Gly Arg Glu
                245                 250                 255

Ala Ala Phe Gly Val Arg Ser Arg Pro Leu Gly Glu Val Arg His Ala
            260                 265                 270

Leu Thr His Arg Arg Leu Arg Val Glu Val Arg Gly Ala Leu Trp Glu
        275                 280                 285

Gly Glu Gly Glu Asp Pro Trp Lys Arg Pro Leu Pro Lys Leu Met Glu
290                 295                 300

Lys Val Leu Arg Lys Ala Leu Pro Leu Leu Ala His Ala Gly Val Val
305                 310                 315                 320

Pro Leu Pro Asp Ala
                325

<210> SEQ ID NO 3
<211> LENGTH: 1998
<212> TYPE: DNA
<213> ORGANISM: Thermus thermophilus
<220> FEATURE:
<221> NAME/KEY: CDS
<222> LOCATION: (1)..(1998)

<400> SEQUENCE: 3

```
atg agg gac cgg gtc cgc tgg cgg gtg ctt tcc ctc cct ccc ctc gcc      48
Met Arg Asp Arg Val Arg Trp Arg Val Leu Ser Leu Pro Pro Leu Ala
1               5                   10                  15 cag tgg cgg gag gtg atg gcg gcc ttg gag gtg ggg ccg gag gcc gcc      96
Gln Trp Arg Glu Val Met Ala Ala Leu Glu Val Gly Pro Glu Ala Ala
            20                  25                  30 ctg gcc tac tgg cac cgg ggc ttt agg cgc aag gag gac ctg gac ccc     144
Leu Ala Tyr Trp His Arg Gly Phe Arg Arg Lys Glu Asp Leu Asp Pro
        35                  40                  45 ccc ctc gcc ctc ctt ccc ctc aag ggc ctg agg gag gcg gcg gcc ctc     192
Pro Leu Ala Leu Leu Pro Leu Lys Gly Leu Arg Glu Ala Ala Ala Leu
    50                  55                  60 ctg gag gag gcg ctc cgc cag ggg aag cgg atc cgc gtc cac ggg gac     240
Leu Glu Glu Ala Leu Arg Gln Gly Lys Arg Ile Arg Val His Gly Asp
65                  70                  75                  80 tac gac gcc gac ggg ctc acg ggc acg gcc atc ctg gtt cgg ggc ctc     288
Tyr Asp Ala Asp Gly Leu Thr Gly Thr Ala Ile Leu Val Arg Gly Leu
                85                  90                  95 gcc gcc ttg ggc gcc gac gtc cac ccc ttc atc ccc cac cgg ctg gag     336
Ala Ala Leu Gly Ala Asp Val His Pro Phe Ile Pro His Arg Leu Glu
            100                 105                 110 gaa ggg tac ggg gtg ctg atg gag cgg gtt ccc gag cac ctc gag gcc     384
Glu Gly Tyr Gly Val Leu Met Glu Arg Val Pro Glu His Leu Glu Ala
        115                 120                 125 tcg gac ctc ttc ctc acc gtg gac tgc ggg atc acg aac cac gcc gag     432
Ser Asp Leu Phe Leu Thr Val Asp Cys Gly Ile Thr Asn His Ala Glu
    130                 135                 140 ctc agg gag ctt ttg gaa aac ggg gtg gag gtg atc gtc acc gac cac     480
Leu Arg Glu Leu Leu Glu Asn Gly Val Glu Val Ile Val Thr Asp His
145                 150                 155                 160 cac acc ccc ggc aag acc cct tcc ccc ggc ctc gtg gtc cac ccc gcc     528
His Thr Pro Gly Lys Thr Pro Ser Pro Gly Leu Val Val His Pro Ala
                165                 170                 175 ctc acc ccg gac ctt aag gag aag ccc acg ggg gcg ggg gtg gtc ttc     576
Leu Thr Pro Asp Leu Lys Glu Lys Pro Thr Gly Ala Gly Val Val Phe
            180                 185                 190 ctc ctc ctc tgg gcc ctc cac gag cgc ctg ggc ctt ccc cca ccc ctg     624
Leu Leu Leu Trp Ala Leu His Glu Arg Leu Gly Leu Pro Pro Pro Leu
        195                 200                 205 gag tac gcc gac ctc gcc gcg gtg ggc acc atc gcc gac gtg gcc ccc     672
Glu Tyr Ala Asp Leu Ala Ala Val Gly Thr Ile Ala Asp Val Ala Pro
    210                 215                 220 ctt tgg ggc tgg aac cgg gcc ttg gtg aag gag ggc ctg gcc cgc atc     720
Leu Trp Gly Trp Asn Arg Ala Leu Val Lys Glu Gly Leu Ala Arg Ile
225                 230                 235                 240 ccc gcc tcc tcc tgg gtt ggg ctc agg ctt ctg gcc gag gcg gtg ggg     768
Pro Ala Ser Ser Trp Val Gly Leu Arg Leu Leu Ala Glu Ala Val Gly
                245                 250                 255 tac acg ggg aag gcg gtg gag gtg gcc ttc cgc atc gcc ccc cgg atc     816
Tyr Thr Gly Lys Ala Val Glu Val Ala Phe Arg Ile Ala Pro Arg Ile
            260                 265                 270 aac gcg gca agc cgc ctc ggg gag gct gag aag gcc cta agg ctc ctc     864
Asn Ala Ala Ser Arg Leu Gly Glu Ala Glu Lys Ala Leu Arg Leu Leu
        275                 280                 285 ctc acc gac gac gcg gcc gag gcc cag gcc ctc gtg ggg gaa ctc cac     912
Leu Thr Asp Asp Ala Ala Glu Ala Gln Ala Leu Val Gly Glu Leu His
    290                 295                 300
```

-continued

| | |
|---|---|
| cgg ctg aac gcc cgc cgc cag acc ctg gag gag gcc atg ctc agg aag<br>Arg Leu Asn Ala Arg Arg Gln Thr Leu Glu Glu Ala Met Leu Arg Lys<br>305     310     315     320 | 960 |
| ctc ctc ccc cag gcg gac ccc gag gcc aag gcc atc gtc ctc ctg gac<br>Leu Leu Pro Gln Ala Asp Pro Glu Ala Lys Ala Ile Val Leu Leu Asp<br>     325     330     335 | 1008 |
| ccc gag ggg cac ccg ggg gtg atg ggc atc gtg gcg agc cgc atc ctg<br>Pro Glu Gly His Pro Gly Val Met Gly Ile Val Ala Ser Arg Ile Leu<br>340     345     350 | 1056 |
| gag gcc acc ctc cgg ccc gtc ttc ctg gtg gcc cag ggc aag ggg acg<br>Glu Ala Thr Leu Arg Pro Val Phe Leu Val Ala Gln Gly Lys Gly Thr<br>355     360     365 | 1104 |
| gtg cgg agc ctc gcc ccc atc agc gcc gtg gag gcc cta agg agc gcc<br>Val Arg Ser Leu Ala Pro Ile Ser Ala Val Glu Ala Leu Arg Ser Ala<br>370     375     380 | 1152 |
| gag gac ctt ttg ttg cgc tac ggg ggg cac aag gag gcg gcg ggc ttc<br>Glu Asp Leu Leu Leu Arg Tyr Gly Gly His Lys Glu Ala Ala Gly Phe<br>385     390     395     400 | 1200 |
| gcc atg gac gag gcc ctc ttc ccc gcc ttc aag gcc cgg gtg gag gcc<br>Ala Met Asp Glu Ala Leu Phe Pro Ala Phe Lys Ala Arg Val Glu Ala<br>     405     410     415 | 1248 |
| tac gcc gcc cgc ttc ccc gac ccc gtg cgc gag gtg gcc ctt ttg gac<br>Tyr Ala Ala Arg Phe Pro Asp Pro Val Arg Glu Val Ala Leu Leu Asp<br>420     425     430 | 1296 |
| ctg ctt ccg gag ccc ggc ctc ctc ccc cag gtc ttc cgg gag ctc gcc<br>Leu Leu Pro Glu Pro Gly Leu Leu Pro Gln Val Phe Arg Glu Leu Ala<br>435     440     445 | 1344 |
| ctt ttg gag ccc tac ggc gag gga aac ccc gag ccc ctc ttc ctc ctc<br>Leu Leu Glu Pro Tyr Gly Glu Gly Asn Pro Glu Pro Leu Phe Leu Leu<br>450     455     460 | 1392 |
| ttc ggc gcc ccg gag gag gcc cgg cgc ctc ggg gag ggc cgc cac ctc<br>Phe Gly Ala Pro Glu Glu Ala Arg Arg Leu Gly Glu Gly Arg His Leu<br>465     470     475     480 | 1440 |
| gcc ttc cgc ctg aag ggg gtg cgg gtc ctg gcc tgg aaa cag ggg gac<br>Ala Phe Arg Leu Lys Gly Val Arg Val Leu Ala Trp Lys Gln Gly Asp<br>     485     490     495 | 1488 |
| ctc gcc ctg ccc ccg gag gtg gag gtg gcg ggc ctc ctc agc gaa aac<br>Leu Ala Leu Pro Pro Glu Val Glu Val Ala Gly Leu Leu Ser Glu Asn<br>500     505     510 | 1536 |
| gcc tgg aac ggc cac ctc gcc tac gag gtc cag gcg gtg gac ctg cga<br>Ala Trp Asn Gly His Leu Ala Tyr Glu Val Gln Ala Val Asp Leu Arg<br>515     520     525 | 1584 |
| aag cca gag gcg ctg gag ggc ggg atc gcg ccc ttc gcc tac ccc ctg<br>Lys Pro Glu Ala Leu Glu Gly Gly Ile Ala Pro Phe Ala Tyr Pro Leu<br>530     535     540 | 1632 |
| ccc ctc ctc gag gcc ctg gcc cgg gcc cgc ctg ggg gaa ggg gtc tac<br>Pro Leu Leu Glu Ala Leu Ala Arg Ala Arg Leu Gly Glu Gly Val Tyr<br>545     550     555     560 | 1680 |
| gtc ccc gag gac aac cct gag ggg ctg gac tac gcc agg aag gcg ggc<br>Val Pro Glu Asp Asn Pro Glu Gly Leu Asp Tyr Ala Arg Lys Ala Gly<br>     565     570     575 | 1728 |
| ttc cgc ctc ctc ccc ccc gag gag gcc ggg ctt tgg ctc ggc ctc ccc<br>Phe Arg Leu Leu Pro Pro Glu Glu Ala Gly Leu Trp Leu Gly Leu Pro<br>580     585     590 | 1776 |
| cca agg ccg gtc ctg ggc agg cgg gtg gag gtg gcc ctg ggg cgg gag<br>Pro Arg Pro Val Leu Gly Arg Arg Val Glu Val Ala Leu Gly Arg Glu<br>595     600     605 | 1824 |
| gcg cgg gcc agg ctt tcc gcc ccc ccc gtc ctc cac acc ccc gag gcc<br>Ala Arg Ala Arg Leu Ser Ala Pro Pro Val Leu His Thr Pro Glu Ala<br>610     615     620 | 1872 |

-continued

```
cgg ctc aaa gcc ctc gtc cac cgc cgc ctc ctc ttc gcc tac gag cgc      1920
Arg Leu Lys Ala Leu Val His Arg Arg Leu Leu Phe Ala Tyr Glu Arg
625                 630                 635                 640 cgt cac ccg ggc ctc ttc agc gag gcc ctc ctc gcc tac tgg gag gtg      1968
Arg His Pro Gly Leu Phe Ser Glu Ala Leu Leu Ala Tyr Trp Glu Val
                645                 650                 655 aac cgt gta cag gag ccc gcg gga agc cca                              1998
Asn Arg Val Gln Glu Pro Ala Gly Ser Pro
            660                 665

<210> SEQ ID NO 4
<211> LENGTH: 666
<212> TYPE: PRT
<213> ORGANISM: Thermus thermophilus

<400> SEQUENCE: 4
```

Met Arg Asp Arg Val Arg Trp Arg Val Leu Ser Leu Pro Pro Leu Ala
1               5                   10                  15

Gln Trp Arg Glu Val Met Ala Ala Leu Glu Val Gly Pro Glu Ala Ala
            20                  25                  30

Leu Ala Tyr Trp His Arg Gly Phe Arg Arg Lys Glu Asp Leu Asp Pro
        35                  40                  45

Pro Leu Ala Leu Leu Pro Leu Lys Gly Leu Arg Glu Ala Ala Ala Leu
    50                  55                  60

Leu Glu Glu Ala Leu Arg Gln Gly Lys Arg Ile Arg Val His Gly Asp
65                  70                  75                  80

Tyr Asp Ala Asp Gly Leu Thr Gly Thr Ala Ile Leu Val Arg Gly Leu
                85                  90                  95

Ala Ala Leu Gly Ala Asp Val His Pro Phe Ile Pro His Arg Leu Glu
            100                 105                 110

Glu Gly Tyr Gly Val Leu Met Glu Arg Val Pro Glu His Leu Glu Ala
        115                 120                 125

Ser Asp Leu Phe Leu Thr Val Asp Cys Gly Ile Thr Asn His Ala Glu
    130                 135                 140

Leu Arg Glu Leu Leu Glu Asn Gly Val Glu Val Ile Val Thr Asp His
145                 150                 155                 160

His Thr Pro Gly Lys Thr Pro Ser Pro Gly Leu Val Val His Pro Ala
                165                 170                 175

Leu Thr Pro Asp Leu Lys Glu Lys Pro Thr Gly Ala Gly Val Val Phe
            180                 185                 190

Leu Leu Leu Trp Ala Leu His Glu Arg Leu Gly Leu Pro Pro Pro Leu
        195                 200                 205

Glu Tyr Ala Asp Leu Ala Ala Val Gly Thr Ile Ala Asp Val Ala Pro
    210                 215                 220

Leu Trp Gly Trp Asn Arg Ala Leu Val Lys Glu Gly Leu Ala Arg Ile
225                 230                 235                 240

Pro Ala Ser Ser Trp Val Gly Leu Arg Leu Leu Ala Glu Ala Val Gly
                245                 250                 255

Tyr Thr Gly Lys Ala Val Glu Val Ala Phe Arg Ile Ala Pro Arg Ile
            260                 265                 270

Asn Ala Ala Ser Arg Leu Gly Glu Ala Glu Lys Ala Leu Arg Leu Leu
        275                 280                 285

Leu Thr Asp Asp Ala Ala Glu Ala Gln Ala Leu Val Gly Glu Leu His
    290                 295                 300

Arg Leu Asn Ala Arg Arg Gln Thr Leu Glu Glu Ala Met Leu Arg Lys

-continued

```
305                 310                 315                 320

Leu Leu Pro Gln Ala Asp Pro Glu Ala Lys Ala Ile Val Leu Leu Asp
                325                 330                 335

Pro Glu Gly His Pro Gly Val Met Gly Ile Val Ala Ser Arg Ile Leu
            340                 345                 350

Glu Ala Thr Leu Arg Pro Val Phe Leu Val Ala Gln Gly Lys Gly Thr
        355                 360                 365

Val Arg Ser Leu Ala Pro Ile Ser Ala Val Glu Ala Leu Arg Ser Ala
    370                 375                 380

Glu Asp Leu Leu Arg Tyr Gly Gly His Lys Glu Ala Ala Gly Phe
385                 390                 395                 400

Ala Met Asp Glu Ala Leu Phe Pro Ala Phe Lys Ala Arg Val Glu Ala
                405                 410                 415

Tyr Ala Ala Arg Phe Pro Asp Pro Val Arg Glu Val Ala Leu Leu Asp
            420                 425                 430

Leu Leu Pro Glu Pro Gly Leu Leu Pro Gln Val Phe Arg Glu Leu Ala
        435                 440                 445

Leu Leu Glu Pro Tyr Gly Glu Gly Asn Pro Glu Pro Leu Phe Leu Leu
    450                 455                 460

Phe Gly Ala Pro Glu Glu Ala Arg Arg Leu Gly Glu Gly Arg His Leu
465                 470                 475                 480

Ala Phe Arg Leu Lys Gly Val Arg Val Leu Ala Trp Lys Gln Gly Asp
                485                 490                 495

Leu Ala Leu Pro Pro Glu Val Glu Val Ala Gly Leu Leu Ser Glu Asn
            500                 505                 510

Ala Trp Asn Gly His Leu Ala Tyr Glu Val Gln Ala Val Asp Leu Arg
        515                 520                 525

Lys Pro Glu Ala Leu Glu Gly Gly Ile Ala Pro Phe Ala Tyr Pro Leu
    530                 535                 540

Pro Leu Leu Glu Ala Leu Ala Arg Ala Arg Leu Gly Glu Gly Val Tyr
545                 550                 555                 560

Val Pro Glu Asp Asn Pro Glu Gly Leu Asp Tyr Ala Arg Lys Ala Gly
                565                 570                 575

Phe Arg Leu Leu Pro Pro Glu Glu Ala Gly Leu Trp Leu Gly Leu Pro
            580                 585                 590

Pro Arg Pro Val Leu Gly Arg Val Glu Val Ala Leu Gly Arg Glu
        595                 600                 605

Ala Arg Ala Arg Leu Ser Ala Pro Pro Val Leu His Thr Pro Glu Ala
    610                 615                 620

Arg Leu Lys Ala Leu Val His Arg Arg Leu Leu Phe Ala Tyr Glu Arg
625                 630                 635                 640

Arg His Pro Gly Leu Phe Ser Glu Ala Leu Leu Ala Tyr Trp Glu Val
                645                 650                 655

Asn Arg Val Gln Glu Pro Ala Gly Ser Pro
            660                 665
```

<210> SEQ ID NO 5
<211> LENGTH: 1029
<212> TYPE: DNA
<213> ORGANISM: Thermus thermophilus
<220> FEATURE:
<221> NAME/KEY: CDS
<222> LOCATION: (1)..(1029)

<400> SEQUENCE: 5

-continued

| | |
|---|---|
| atg cgg ctt ctc ctc ttc cgg caa cgg aac ttc cgc aac ctg gcc ctg<br>Met Arg Leu Leu Leu Phe Arg Gln Arg Asn Phe Arg Asn Leu Ala Leu<br>1                          5                      10                   15 | 48 |
| gag gcc tac cgc ccc ccg ccg ggc ctt tcc gcc ctg gtg ggg gcc aac<br>Glu Ala Tyr Arg Pro Pro Pro Gly Leu Ser Ala Leu Val Gly Ala Asn<br>                    20                    25                      30 | 96 |
| gcc cag ggg aag acg agc ctc ctc ctg ggg atc cac ctg gcc cta ggg<br>Ala Gln Gly Lys Thr Ser Leu Leu Leu Gly Ile His Leu Ala Leu Gly<br>              35                    40                    45 | 144 |
| ggg gag gtc ccc ctg ggc ctt gcc gac ctc gtc cgc ttc ggg gag gag<br>Gly Glu Val Pro Leu Gly Leu Ala Asp Leu Val Arg Phe Gly Glu Glu<br>50                         55                    60 | 192 |
| gag gcc tgg ctc cac gcc gag gtg gag acg gag ctc ggg gcc tac cgc<br>Glu Ala Trp Leu His Ala Glu Val Glu Thr Glu Leu Gly Ala Tyr Arg<br>65                         70                    75                   80 | 240 |
| ctg gag cac cgc ctg ggc ccc ggg ggg cgg gag gtc ctc ctc aac ggg<br>Leu Glu His Arg Leu Gly Pro Gly Gly Arg Glu Val Leu Leu Asn Gly<br>                    85                    90                    95 | 288 |
| aag cgg gtg agc ctt cgg acc ctt tgg gag ctt ccc ggc tcg gtc ctc<br>Lys Arg Val Ser Leu Arg Thr Leu Trp Glu Leu Pro Gly Ser Val Leu<br>                  100                 105               110 | 336 |
| gtc tcc cct ctg gac ctc gag gcg gtc ctc ggg ccc aag gag gag cgg<br>Val Ser Pro Leu Asp Leu Glu Ala Val Leu Gly Pro Lys Glu Glu Arg<br>         115                 120               125 | 384 |
| cgg gcc tac ctg gac cgg ctc atc gcc cgc ttc tcc cgc cgc tac gcc<br>Arg Ala Tyr Leu Asp Arg Leu Ile Ala Arg Phe Ser Arg Arg Tyr Ala<br>      130               135               140 | 432 |
| gcc ctc ctt tcc gcc tac gag aag gcg ctg cgc cag cgg aac gcc ctc<br>Ala Leu Leu Ser Ala Tyr Glu Lys Ala Leu Arg Gln Arg Asn Ala Leu<br>145                      150                 155               160 | 480 |
| ctc aag gcc ggg ggg gag ggc ctt tcc gcc tgg gac cgg gag ctc gcc<br>Leu Lys Ala Gly Gly Glu Gly Leu Ser Ala Trp Asp Arg Glu Leu Ala<br>                  165                 170               175 | 528 |
| cgc tac ggg gac gag atc gtg gcc ctg agg cgc cgc ttc ctc cgg cgc<br>Arg Tyr Gly Asp Glu Ile Val Ala Leu Arg Arg Arg Phe Leu Arg Arg<br>              180                 185               190 | 576 |
| ttc gcc ccc atc ctg cgg gag gtc cac gcc gcc ctc gcc gcc aag gag<br>Phe Ala Pro Ile Leu Arg Glu Val His Ala Ala Leu Ala Ala Lys Glu<br>         195                 200               205 | 624 |
| gcg ggg ctt cgc ttg gag gag acc gcg ggg gaa ggg gtg ctc cgg gcc<br>Ala Gly Leu Arg Leu Glu Glu Thr Ala Gly Glu Gly Val Leu Arg Ala<br>      210               215               220 | 672 |
| ctc gag gcc agc cgg gcc gag gag cgg gaa cgg ggc cag acc ctg gtg<br>Leu Glu Ala Ser Arg Ala Glu Glu Arg Glu Arg Gly Gln Thr Leu Val<br>225                      230                 235               240 | 720 |
| ggg ccc cac cgg gac gac ctg gtc ttc ctc ctg gag ggg cgg ccc gcc<br>Gly Pro His Arg Asp Asp Leu Val Phe Leu Leu Glu Gly Arg Pro Ala<br>                  245                 250               255 | 768 |
| cac cgg ttc gcc agc cgc ggg gag gcc aag acc ctg gcc ctg gcc ctg<br>His Arg Phe Ala Ser Arg Gly Glu Ala Lys Thr Leu Ala Leu Ala Leu<br>         260                 265               270 | 816 |
| cgc ctc gcc gag cac cgc ctc ctc ggc gag cac cac ggc gag ccc ccc<br>Arg Leu Ala Glu His Arg Leu Leu Gly Glu His His Gly Glu Pro Pro<br>      275               280               285 | 864 |
| ctc ctc ctc gtg gac gag tgg ggg gag gag ctg gac gag gcc cgc agg<br>Leu Leu Leu Val Asp Glu Trp Gly Glu Glu Leu Asp Glu Ala Arg Arg<br>290                      295                 300 | 912 |
| cgg gcc gtc ctc gcc tac gcc cag gcc ctg ccc cag gcc atc ctg gcg<br>Arg Ala Val Leu Ala Tyr Ala Gln Ala Leu Pro Gln Ala Ile Leu Ala<br>305                      310                 315               320 | 960 |

```
ggg ctg gaa gcc ccc ccg ggg gtg ccg gta tgc tcg gtg gta cga ggg      1008
Gly Leu Glu Ala Pro Pro Gly Val Pro Val Cys Ser Val Val Arg Gly
            325                 330                 335 gtg gtc ctg tgc cct ggc gcc                                           1029
Val Val Leu Cys Pro Gly Ala
            340
```

<210> SEQ ID NO 6
<211> LENGTH: 343
<212> TYPE: PRT
<213> ORGANISM: Thermus thermophilus

<400> SEQUENCE: 6

```
Met Arg Leu Leu Leu Phe Arg Gln Arg Asn Phe Arg Asn Leu Ala Leu
1               5                   10                  15

Glu Ala Tyr Arg Pro Pro Gly Leu Ser Ala Leu Val Gly Ala Asn
            20                  25                  30

Ala Gln Gly Lys Thr Ser Leu Leu Gly Ile His Leu Ala Leu Gly
        35                  40                  45

Gly Glu Val Pro Leu Gly Leu Ala Asp Leu Val Arg Phe Gly Glu Glu
    50                  55                  60

Glu Ala Trp Leu His Ala Glu Val Glu Thr Glu Leu Gly Ala Tyr Arg
65                  70                  75                  80

Leu Glu His Arg Leu Gly Pro Gly Gly Arg Glu Val Leu Leu Asn Gly
                85                  90                  95

Lys Arg Val Ser Leu Arg Thr Leu Trp Glu Leu Pro Gly Ser Val Leu
            100                 105                 110

Val Ser Pro Leu Asp Leu Glu Ala Val Leu Gly Pro Lys Glu Glu Arg
        115                 120                 125

Arg Ala Tyr Leu Asp Arg Leu Ile Ala Arg Phe Ser Arg Arg Tyr Ala
130                 135                 140

Ala Leu Leu Ser Ala Tyr Glu Lys Ala Leu Arg Gln Arg Asn Ala Leu
145                 150                 155                 160

Leu Lys Ala Gly Gly Glu Gly Leu Ser Ala Trp Asp Arg Glu Leu Ala
                165                 170                 175

Arg Tyr Gly Asp Glu Ile Val Ala Leu Arg Arg Arg Phe Leu Arg Arg
            180                 185                 190

Phe Ala Pro Ile Leu Arg Glu Val His Ala Ala Leu Ala Ala Lys Glu
        195                 200                 205

Ala Gly Leu Arg Leu Glu Glu Thr Ala Gly Glu Gly Val Leu Arg Ala
    210                 215                 220

Leu Glu Ala Ser Arg Ala Glu Glu Arg Glu Arg Gly Gln Thr Leu Val
225                 230                 235                 240

Gly Pro His Arg Asp Asp Leu Val Phe Leu Leu Glu Gly Arg Pro Ala
                245                 250                 255

His Arg Phe Ala Ser Arg Gly Glu Ala Lys Thr Leu Ala Leu Ala Leu
            260                 265                 270

Arg Leu Ala Glu His Arg Leu Leu Gly Glu His Gly Glu Pro Pro
        275                 280                 285

Leu Leu Leu Val Asp Glu Trp Gly Glu Glu Leu Asp Glu Ala Arg Arg
    290                 295                 300

Arg Ala Val Leu Ala Tyr Ala Gln Ala Leu Pro Gln Ala Ile Leu Ala
305                 310                 315                 320

Gly Leu Glu Ala Pro Pro Gly Val Pro Val Cys Ser Val Val Arg Gly
                325                 330                 335
```

Val Val Leu Cys Pro Gly Ala
340

<210> SEQ ID NO 7
<211> LENGTH: 2934
<212> TYPE: DNA
<213> ORGANISM: Thermus thermophilus
<220> FEATURE:
<221> NAME/KEY: CDS
<222> LOCATION: (1)..(2934)

<400> SEQUENCE: 7

| | | | | | | | | | | | | | | | | |
|---|---|---|---|---|---|---|---|---|---|---|---|---|---|---|---|---|
| atg | gaa | atc | gcg | cta | gag | agg | atc | tac | ggc | cac | cgc | ctg | gcg | ctc | ccg | 48 |
| Met | Glu | Ile | Ala | Leu | Glu | Arg | Ile | Tyr | Gly | His | Arg | Leu | Ala | Leu | Pro | |
| 1 | | | | 5 | | | | | 10 | | | | | 15 | | |
| cag | gtg | ggg | gcg | gcc | ttg | ctt | ttc | gcc | cag | gag | gcc | ccc | ccg | gcc | ctc | 96 |
| Gln | Val | Gly | Ala | Ala | Leu | Leu | Phe | Ala | Gln | Glu | Ala | Pro | Pro | Ala | Leu | |
| | | | 20 | | | | | 25 | | | | | 30 | | | |
| ctc | ctc | gtc | ccc | gag | gcg | cgg | ctt | agg | cgc | tac | cgg | gac | ctc | tcc | gcc | 144 |
| Leu | Leu | Val | Pro | Glu | Ala | Arg | Leu | Arg | Arg | Tyr | Arg | Asp | Leu | Ser | Ala | |
| | | 35 | | | | | 40 | | | | | 45 | | | | |
| ttc | ggg | gcc | aag | gtc | tac | gtg | aac | ccc | ggc | ctc | gag | gcc | ctg | gag | gaa | 192 |
| Phe | Gly | Ala | Lys | Val | Tyr | Val | Asn | Pro | Gly | Leu | Glu | Ala | Leu | Glu | Glu | |
| | 50 | | | | | 55 | | | | | 60 | | | | | |
| aaa | gcc | ctc | ttc | gtc | ctc | tcc | tac | gag | gag | gcc | cta | agc | ccc | ttc | ccc | 240 |
| Lys | Ala | Leu | Phe | Val | Leu | Ser | Tyr | Glu | Glu | Ala | Leu | Ser | Pro | Phe | Pro | |
| 65 | | | | | 70 | | | | | 75 | | | | | 80 | |
| gag | gac | cct | gag | gcc | tgg | cgg | ctt | ctt | ctg | gag | gtg | ggc | cgc | gcc | tac | 288 |
| Glu | Asp | Pro | Glu | Ala | Trp | Arg | Leu | Leu | Leu | Glu | Val | Gly | Arg | Ala | Tyr | |
| | | | | 85 | | | | | 90 | | | | | 95 | | |
| ccc | cgg | gag | gcc | ctc | ctc | tcc | cgc | ctc | ctc | aag | ctg | ggc | tac | gcc | cgg | 336 |
| Pro | Arg | Glu | Ala | Leu | Leu | Ser | Arg | Leu | Leu | Lys | Leu | Gly | Tyr | Ala | Arg | |
| | | | 100 | | | | | 105 | | | | | 110 | | | |
| gac | gag | gac | tac | cgc | gtc | ctg | ggg | gag | gtg | gtg | gag | ctc | ggc | gag | gtg | 384 |
| Asp | Glu | Asp | Tyr | Arg | Val | Leu | Gly | Glu | Val | Val | Glu | Leu | Gly | Glu | Val | |
| | | 115 | | | | | 120 | | | | | 125 | | | | |
| cgc | ctg | gag | ttc | ttc | ggg | gac | gag | ctg | gaa | agg | ctt | gtg | gtc | cgg | ggg | 432 |
| Arg | Leu | Glu | Phe | Phe | Gly | Asp | Glu | Leu | Glu | Arg | Leu | Val | Val | Arg | Gly | |
| | 130 | | | | | 135 | | | | | 140 | | | | | |
| gag | gaa | agg | cgg | cgc | cac | gtc | ctt | ctg | ccc | aag | ccg | ggg | aag | gcg | gag | 480 |
| Glu | Glu | Arg | Arg | Arg | His | Val | Leu | Leu | Pro | Lys | Pro | Gly | Lys | Ala | Glu | |
| 145 | | | | | 150 | | | | | 155 | | | | | 160 | |
| ggc | ttc | acc | tcc | aag | aag | gtc | ctc | cac | ttc | cct | ggc | ccc | gtc | tac | ctg | 528 |
| Gly | Phe | Thr | Ser | Lys | Lys | Val | Leu | His | Phe | Pro | Gly | Pro | Val | Tyr | Leu | |
| | | | | 165 | | | | | 170 | | | | | 175 | | |
| gac | acc | ccc | gcc | ctc | gcc | ccc | aag | gcc | ctt | tgg | ccc | ctc | ctc | gcg | gga | 576 |
| Asp | Thr | Pro | Ala | Leu | Ala | Pro | Lys | Ala | Leu | Trp | Pro | Leu | Leu | Ala | Gly | |
| | | | 180 | | | | | 185 | | | | | 190 | | | |
| agg | ccc | tgg | gtg | gcc | ctg | ggc | ggc | ggg | gtg | gag | ctc | ccc | ccc | ttg | gag | 624 |
| Arg | Pro | Trp | Val | Ala | Leu | Gly | Gly | Gly | Val | Glu | Leu | Pro | Pro | Leu | Glu | |
| | | 195 | | | | | 200 | | | | | 205 | | | | |
| ctc | ggg | gcg | agg | ccc | ctt | cct | cct | tac | cgg | gga | agc | ctg | aag | gcc | ctg | 672 |
| Leu | Gly | Ala | Arg | Pro | Leu | Pro | Pro | Tyr | Arg | Gly | Ser | Leu | Lys | Ala | Leu | |
| | 210 | | | | | 215 | | | | | 220 | | | | | |
| gaa | aag | gac | ctc | gcc | cgc | tgg | ctt | gcc | gag | ggg | aag | cgg | gtc | cac | ctc | 720 |
| Glu | Lys | Asp | Leu | Ala | Arg | Trp | Leu | Ala | Glu | Gly | Lys | Arg | Val | His | Leu | |
| 225 | | | | | 230 | | | | | 235 | | | | | 240 | |
| ttc | gtg | ggc | cac | gcc | cgc | acc | ttg | gag | tac | ctc | aaa | agg | cgc | ctc | cag | 768 |
| Phe | Val | Gly | His | Ala | Arg | Thr | Leu | Glu | Tyr | Leu | Lys | Arg | Arg | Leu | Gln | |
| | | | | 245 | | | | | 250 | | | | | 255 | | |

```
gcc ttc tcg ccc ctc atc ctg gac cgc ttc ccc ggc ccc aag ggg cgg      816
Ala Phe Ser Pro Leu Ile Leu Asp Arg Phe Pro Gly Pro Lys Gly Arg
            260                 265                 270 ctt gcc ctc ctc ccc ggg gac ttt gag ggc ggg gcg gag tgg gga gag      864
Leu Ala Leu Leu Pro Gly Asp Phe Glu Gly Gly Ala Glu Trp Gly Glu
        275                 280                 285 tgg gtc ctc ctc acc gag gcc ctg gtc ttc gcc acc ggg ggg gtg cgg      912
Trp Val Leu Leu Thr Glu Ala Leu Val Phe Ala Thr Gly Gly Val Arg
    290                 295                 300 gcc agg gtc cgg gta ggg gag ggg ctc agc gac ccc ggg gcc ctt tcc      960
Ala Arg Val Arg Val Gly Glu Gly Leu Ser Asp Pro Gly Ala Leu Ser
305                 310                 315                 320 cca ggg gac tac ctc atc cac ccg gag cac ggc gtc ggg cag tac ctg     1008
Pro Gly Asp Tyr Leu Ile His Pro Glu His Gly Val Gly Gln Tyr Leu
                325                 330                 335 ggc ctc gag acc cgg gag gtc ctg ggg gtc aag cgg gac tac ctg gtc     1056
Gly Leu Glu Thr Arg Glu Val Leu Gly Val Lys Arg Asp Tyr Leu Val
            340                 345                 350 ctg cgc tac aag ggg gaa ggg aag ctc tac ctc ccc gtg gag cag ctt     1104
Leu Arg Tyr Lys Gly Glu Gly Lys Leu Tyr Leu Pro Val Glu Gln Leu
        355                 360                 365 ccc ctc ctc aag cgc cac ccc ggg acc acc gac gac ccc ccg gag ctt     1152
Pro Leu Leu Lys Arg His Pro Gly Thr Thr Asp Asp Pro Pro Glu Leu
    370                 375                 380 tcc tcc ctg ggc aag aac gag tgg caa agg gcc aag gag cgg gcg cgg     1200
Ser Ser Leu Gly Lys Asn Glu Trp Gln Arg Ala Lys Glu Arg Ala Arg
385                 390                 395                 400 aag gac gtg gag gag ctg gct ggg cgc ctc ctc gtc ctc cag gcc aag     1248
Lys Asp Val Glu Glu Leu Ala Gly Arg Leu Leu Val Leu Gln Ala Lys
                405                 410                 415 cgc aag gcc acc ccg ggc cgg gcc ttt ccc cct ttg ccc gag tgg gat     1296
Arg Lys Ala Thr Pro Gly Arg Ala Phe Pro Pro Leu Pro Glu Trp Asp
            420                 425                 430 cct ctg gtg gag aag ggg ttc ccc tac gag ctc acc ccc gac cag aag     1344
Pro Leu Val Glu Lys Gly Phe Pro Tyr Glu Leu Thr Pro Asp Gln Lys
        435                 440                 445 cgg gcc ctg gag gag gtc ctc cgc gac ctg gaa agc ccc cac ccc atg     1392
Arg Ala Leu Glu Glu Val Leu Arg Asp Leu Glu Ser Pro His Pro Met
    450                 455                 460 gac cgc ctg gtc tcg ggg gac gtg ggc ttc ggc aag acg gag gtg gcc     1440
Asp Arg Leu Val Ser Gly Asp Val Gly Phe Gly Lys Thr Glu Val Ala
465                 470                 475                 480 ctg agg gcc gcc cac cgg gtg gtg ggg cac ggg gcc cag gtg gcc ttc     1488
Leu Arg Ala Ala His Arg Val Val Gly His Gly Ala Gln Val Ala Phe
                485                 490                 495 ctg ggg cca acc acc ctc ctc gcc gag cag cac ggg aag acc ttt agg     1536
Leu Gly Pro Thr Thr Leu Leu Ala Glu Gln His Gly Lys Thr Phe Arg
            500                 505                 510 gag cgc ttc cag ggg ctt ccc gtg agg gtt gcg gtc ctc tcc cgc ttc     1584
Glu Arg Phe Gln Gly Leu Pro Val Arg Val Ala Val Leu Ser Arg Phe
        515                 520                 525 acc ccg ccc aag gag gag gag gcc atc cta aaa ggc ctc gcc gag ggg     1632
Thr Pro Pro Lys Glu Glu Glu Ala Ile Leu Lys Gly Leu Ala Glu Gly
    530                 535                 540 acg gtg gac atc gtc atc ggc acc cac cgc ctc ctc cag gag gac gtg     1680
Thr Val Asp Ile Val Ile Gly Thr His Arg Leu Leu Gln Glu Asp Val
545                 550                 555                 560 cgc ttc agg gac ctc ggc ctc ctc atc gtg gac gag gag cac cgc ttc     1728
Arg Phe Arg Asp Leu Gly Leu Leu Ile Val Asp Glu Glu His Arg Phe
                565                 570                 575
```

-continued

| | |
|---|---|
| ggc gtg gcc caa aag gag agg atc cgg gag ctc aag gcg gag gtg gac<br>Gly Val Ala Gln Lys Glu Arg Ile Arg Glu Leu Lys Ala Glu Val Asp<br>580 585 590 | 1776 |
| acc ctc tac ctc tcc gcc acc ccc atc ccc cgc acc ctc tac tcc gcc<br>Thr Leu Tyr Leu Ser Ala Thr Pro Ile Pro Arg Thr Leu Tyr Ser Ala<br>595 600 605 | 1824 |
| ctg gtg ggc ctc aaa gac ctt tcc agc atc cag acc ccg ccc ccg ggg<br>Leu Val Gly Leu Lys Asp Leu Ser Ser Ile Gln Thr Pro Pro Pro Gly<br>610 615 620 | 1872 |
| cgc aag ccc atc aag acc ttc ctc gct ccc ttt gat ccc ctc ttg gtg<br>Arg Lys Pro Ile Lys Thr Phe Leu Ala Pro Phe Asp Pro Leu Leu Val<br>625 630 635 640 | 1920 |
| cgg gag gcc atc ctc ttt gag ctg gag cgt ggg ggc aag gtc ttc tac<br>Arg Glu Ala Ile Leu Phe Glu Leu Glu Arg Gly Gly Lys Val Phe Tyr<br>645 650 655 | 1968 |
| gtc cac gac cgg gtg gcc tcc ata gag gcc agg cgg cgc ttt ctg gaa<br>Val His Asp Arg Val Ala Ser Ile Glu Ala Arg Arg Arg Phe Leu Glu<br>660 665 670 | 2016 |
| aac ctc gtc ccc gag gcc cgc atc ggg gtg gtc cac ggc cag atg ccc<br>Asn Leu Val Pro Glu Ala Arg Ile Gly Val Val His Gly Gln Met Pro<br>675 680 685 | 2064 |
| gaa agc ctc att gag gag acc atg ctc ctc ttc gcc gaa ggg gcg tac<br>Glu Ser Leu Ile Glu Glu Thr Met Leu Leu Phe Ala Glu Gly Ala Tyr<br>690 695 700 | 2112 |
| gac gtc ctc ctc gcc acc acc atc att gag gcg ggc ctg gac gtg ccc<br>Asp Val Leu Leu Ala Thr Thr Ile Ile Glu Ala Gly Leu Asp Val Pro<br>705 710 715 720 | 2160 |
| gag gcg aac acc atc ctc att gag cgg gcg gac cgc ctg ggc ctc gcc<br>Glu Ala Asn Thr Ile Leu Ile Glu Arg Ala Asp Arg Leu Gly Leu Ala<br>725 730 735 | 2208 |
| acc ttg tac cag ctc cgg ggc cgg gtg ggg cgg agg gag gag gag gcc<br>Thr Leu Tyr Gln Leu Arg Gly Arg Val Gly Arg Arg Glu Glu Glu Ala<br>740 745 750 | 2256 |
| tac gcc tac ctc ttc cac ccg cct cgc ctc acc gag gcc gcg gag aag<br>Tyr Ala Tyr Leu Phe His Pro Pro Arg Leu Thr Glu Ala Ala Glu Lys<br>755 760 765 | 2304 |
| cgc ctc gcc gcc atc gcc gac ctc tcc gat ctg ggc tcg ggc cac ctc<br>Arg Leu Ala Ala Ile Ala Asp Leu Ser Asp Leu Gly Ser Gly His Leu<br>770 775 780 | 2352 |
| ctg gcc gaa agg gac atg gaa atc cgg ggc gtg ggg aac ctt ttg ggg<br>Leu Ala Glu Arg Asp Met Glu Ile Arg Gly Val Gly Asn Leu Leu Gly<br>785 790 795 800 | 2400 |
| ccg gag cag cac ggg cac atc cgg gcg ctt tcc ctc gag gtc tac acc<br>Pro Glu Gln His Gly His Ile Arg Ala Leu Ser Leu Glu Val Tyr Thr<br>805 810 815 | 2448 |
| gag ctt ctg gaa gag gcc atc cgc aag ctc aag ggg gag gcc aag gag<br>Glu Leu Leu Glu Glu Ala Ile Arg Lys Leu Lys Gly Glu Ala Lys Glu<br>820 825 830 | 2496 |
| gag cgg cgg cac gtg acc ctg gac ctc gcc ctc tcc gcc cgg ctg ccc<br>Glu Arg Arg His Val Thr Leu Asp Leu Ala Leu Ser Ala Arg Leu Pro<br>835 840 845 | 2544 |
| gcg gag tac gtg ggg agc ctc gag gcc agg agc cgc tac tac agc cgt<br>Ala Glu Tyr Val Gly Ser Leu Glu Ala Arg Ser Arg Tyr Tyr Ser Arg<br>850 855 860 | 2592 |
| ttt gcc gag gcg aaa agc ctc gcc gag ctt tcc cgc ctg gtg cgg gag<br>Phe Ala Glu Ala Lys Ser Leu Ala Glu Leu Ser Arg Leu Val Arg Glu<br>865 870 875 880 | 2640 |
| ctc aaa gag cgc tac ggg ccc ctt cct gag gag gcg gag aac ttc gtg<br>Leu Lys Glu Arg Tyr Gly Pro Leu Pro Glu Glu Ala Glu Asn Phe Val | 2688 |

```
                    885             890             895
gcc ctc gcc cgg ctc cgc ctg gtg gcg gag agg aag ggg gtg gtg tcc          2736
Ala Leu Ala Arg Leu Arg Leu Val Ala Glu Arg Lys Gly Val Val Ser
            900             905             910 atc acg gag ggc ctc acc cac ctg gag gtg gtc ttc ccc cgc tac ccc          2784
Ile Thr Glu Gly Leu Thr His Leu Glu Val Val Phe Pro Arg Tyr Pro
        915             920             925 ctg gac tac gac gcc cgc ggc ctc aag ggg ctt ccc tac cgg gtg gag          2832
Leu Asp Tyr Asp Ala Arg Gly Leu Lys Gly Leu Pro Tyr Arg Val Glu
    930             935             940 ctt acg cag tac ccg ccc ggg ttc cgc ctg gag aag aag ggc ctg agg          2880
Leu Thr Gln Tyr Pro Pro Gly Phe Arg Leu Glu Lys Lys Gly Leu Arg
945             950             955             960 ccc cgg gac tac ccc gag gcc ctg atg gag gtg ctc tac ctc ttc gcc          2928
Pro Arg Asp Tyr Pro Glu Ala Leu Met Glu Val Leu Tyr Leu Phe Ala
            965             970             975 gac ctc                                                                  2934
Asp Leu <210> SEQ ID NO 8
<211> LENGTH: 978
<212> TYPE: PRT
<213> ORGANISM: Thermus thermophilus

<400> SEQUENCE: 8

Met Glu Ile Ala Leu Glu Arg Ile Tyr Gly His Arg Leu Ala Leu Pro
1               5                   10                  15

Gln Val Gly Ala Ala Leu Leu Phe Ala Gln Glu Ala Pro Pro Ala Leu
            20                  25                  30

Leu Leu Val Pro Glu Ala Arg Leu Arg Arg Tyr Arg Asp Leu Ser Ala
        35                  40                  45

Phe Gly Ala Lys Val Tyr Val Asn Pro Gly Leu Glu Ala Leu Glu Glu
    50                  55                  60

Lys Ala Leu Phe Val Leu Ser Tyr Glu Glu Ala Leu Ser Pro Phe Pro
65                  70                  75                  80

Glu Asp Pro Glu Ala Trp Arg Leu Leu Leu Glu Val Gly Arg Ala Tyr
                85                  90                  95

Pro Arg Glu Ala Leu Leu Ser Arg Leu Leu Lys Leu Gly Tyr Ala Arg
            100                 105                 110

Asp Glu Asp Tyr Arg Val Leu Gly Glu Val Val Glu Leu Gly Glu Val
        115                 120                 125

Arg Leu Glu Phe Phe Gly Asp Glu Leu Glu Arg Leu Val Val Arg Gly
    130                 135                 140

Glu Glu Arg Arg Arg His Val Leu Leu Pro Lys Pro Gly Lys Ala Glu
145                 150                 155                 160

Gly Phe Thr Ser Lys Lys Val Leu His Phe Pro Gly Pro Val Tyr Leu
                165                 170                 175

Asp Thr Pro Ala Leu Ala Pro Lys Ala Leu Trp Pro Leu Leu Ala Gly
            180                 185                 190

Arg Pro Trp Val Ala Leu Gly Gly Gly Val Glu Leu Pro Pro Leu Glu
        195                 200                 205

Leu Gly Ala Arg Pro Leu Pro Pro Tyr Arg Gly Ser Leu Lys Ala Leu
    210                 215                 220

Glu Lys Asp Leu Ala Arg Trp Leu Ala Glu Gly Lys Arg Val His Leu
225                 230                 235                 240

Phe Val Gly His Ala Arg Thr Leu Glu Tyr Leu Lys Arg Arg Leu Gln
```

-continued

```
                245                 250                 255
Ala Phe Ser Pro Leu Ile Leu Asp Arg Phe Pro Gly Pro Lys Gly Arg
                260                 265                 270
Leu Ala Leu Leu Pro Gly Asp Phe Glu Gly Ala Glu Trp Gly Glu
                275                 280             285
Trp Val Leu Leu Thr Glu Ala Leu Val Phe Ala Thr Gly Gly Val Arg
    290                 295                 300
Ala Arg Val Arg Val Gly Glu Gly Leu Ser Asp Pro Gly Ala Leu Ser
305                 310                 315                 320
Pro Gly Asp Tyr Leu Ile His Pro Glu His Gly Val Gly Gln Tyr Leu
                325                 330                 335
Gly Leu Glu Thr Arg Glu Val Leu Gly Val Lys Arg Asp Tyr Leu Val
                340                 345                 350
Leu Arg Tyr Lys Gly Glu Gly Lys Leu Tyr Leu Pro Val Glu Gln Leu
                355                 360                 365
Pro Leu Leu Lys Arg His Pro Gly Thr Thr Asp Asp Pro Pro Glu Leu
                370                 375                 380
Ser Ser Leu Gly Lys Asn Glu Trp Gln Arg Ala Lys Glu Arg Ala Arg
385                 390                 395                 400
Lys Asp Val Glu Glu Leu Ala Gly Arg Leu Val Leu Gln Ala Lys
                405                 410                 415
Arg Lys Ala Thr Pro Gly Arg Ala Phe Pro Pro Leu Pro Glu Trp Asp
                420                 425                 430
Pro Leu Val Glu Lys Gly Phe Pro Tyr Glu Leu Thr Pro Asp Gln Lys
                435                 440                 445
Arg Ala Leu Glu Glu Val Leu Arg Asp Leu Glu Ser Pro His Pro Met
            450                 455                 460
Asp Arg Leu Val Ser Gly Asp Val Gly Phe Gly Lys Thr Glu Val Ala
465                 470                 475                 480
Leu Arg Ala Ala His Arg Val Val Gly His Gly Ala Gln Val Ala Phe
                485                 490                 495
Leu Gly Pro Thr Thr Leu Leu Ala Glu Gln His Gly Lys Thr Phe Arg
                500                 505                 510
Glu Arg Phe Gln Gly Leu Pro Val Arg Val Ala Val Leu Ser Arg Phe
                515                 520                 525
Thr Pro Pro Lys Glu Glu Ala Ile Leu Lys Gly Leu Ala Glu Gly
                530                 535             540
Thr Val Asp Ile Val Ile Gly Thr His Arg Leu Leu Gln Glu Asp Val
545                 550                 555                 560
Arg Phe Arg Asp Leu Gly Leu Leu Ile Val Asp Glu Glu His Arg Phe
                565                 570                 575
Gly Val Ala Gln Lys Glu Arg Ile Arg Glu Leu Lys Ala Glu Val Asp
                580                 585                 590
Thr Leu Tyr Leu Ser Ala Thr Pro Ile Pro Arg Thr Leu Tyr Ser Ala
                595                 600                 605
Leu Val Gly Leu Lys Asp Leu Ser Ser Ile Gln Thr Pro Pro Gly
                610                 615                 620
Arg Lys Pro Ile Lys Thr Phe Leu Ala Pro Phe Asp Pro Leu Leu Val
625                 630                 635                 640
Arg Glu Ala Ile Leu Phe Glu Leu Glu Arg Gly Gly Lys Val Phe Tyr
                645                 650                 655
Val His Asp Arg Val Ala Ser Ile Glu Ala Arg Arg Phe Leu Glu
                660                 665             670
```

Asn Leu Val Pro Glu Ala Arg Ile Gly Val His Gly Gln Met Pro
            675                 680                 685

Glu Ser Leu Ile Glu Glu Thr Met Leu Leu Phe Ala Glu Gly Ala Tyr
        690                 695                 700

Asp Val Leu Leu Ala Thr Thr Ile Ile Glu Ala Gly Leu Asp Val Pro
705                 710                 715                 720

Glu Ala Asn Thr Ile Leu Ile Glu Arg Ala Asp Arg Leu Gly Leu Ala
                725                 730                 735

Thr Leu Tyr Gln Leu Arg Gly Arg Val Gly Arg Arg Glu Glu Glu Ala
            740                 745                 750

Tyr Ala Tyr Leu Phe His Pro Pro Arg Leu Thr Glu Ala Ala Glu Lys
        755                 760                 765

Arg Leu Ala Ala Ile Ala Asp Leu Ser Asp Leu Gly Ser Gly His Leu
    770                 775                 780

Leu Ala Glu Arg Asp Met Glu Ile Arg Gly Val Gly Asn Leu Leu Gly
785                 790                 795                 800

Pro Glu Gln His Gly His Ile Arg Ala Leu Ser Leu Glu Val Tyr Thr
                805                 810                 815

Glu Leu Leu Glu Glu Ala Ile Arg Lys Leu Lys Gly Glu Ala Lys Glu
            820                 825                 830

Glu Arg Arg His Val Thr Leu Asp Leu Ala Leu Ser Ala Arg Leu Pro
        835                 840                 845

Ala Glu Tyr Val Gly Ser Leu Glu Ala Arg Ser Arg Tyr Tyr Ser Arg
    850                 855                 860

Phe Ala Glu Ala Lys Ser Leu Ala Glu Leu Ser Arg Leu Val Arg Glu
865                 870                 875                 880

Leu Lys Glu Arg Tyr Gly Pro Leu Pro Glu Glu Ala Glu Asn Phe Val
                885                 890                 895

Ala Leu Ala Arg Leu Arg Leu Val Ala Glu Arg Lys Gly Val Val Ser
            900                 905                 910

Ile Thr Glu Gly Leu Thr His Leu Glu Val Val Phe Pro Arg Tyr Pro
        915                 920                 925

Leu Asp Tyr Asp Ala Arg Gly Leu Lys Gly Leu Pro Tyr Arg Val Glu
    930                 935                 940

Leu Thr Gln Tyr Pro Pro Gly Phe Arg Leu Glu Lys Lys Gly Leu Arg
945                 950                 955                 960

Pro Arg Asp Tyr Pro Glu Ala Leu Met Glu Val Leu Tyr Leu Phe Ala
                965                 970                 975

Asp Leu

<210> SEQ ID NO 9
<211> LENGTH: 38
<212> TYPE: DNA
<213> ORGANISM: Artificial Sequence
<220> FEATURE:
<223> OTHER INFORMATION: Synthetic DNA

<400> SEQUENCE: 9
atatcatatg gaagcctggc ggaaagccct cctcgcct                    38

<210> SEQ ID NO 10
<211> LENGTH: 41
<212> TYPE: DNA
<213> ORGANISM: Artificial Sequence
<220> FEATURE:
<223> OTHER INFORMATION: Synthetic DNA

<400> SEQUENCE: 10
atatagatct ttattatgcg tccgggaggg ggactacgcc c                41

<210> SEQ ID NO 11
<211> LENGTH: 31
<212> TYPE: DNA
<213> ORGANISM: Artificial Sequence
<220> FEATURE:
<223> OTHER INFORMATION: Synthetic DNA

<400> SEQUENCE: 11
atcatatgag agaccgggtc cgctggcggg t                           31

<210> SEQ ID NO 12
<211> LENGTH: 32
<212> TYPE: DNA
<213> ORGANISM: Artificial Sequence
<220> FEATURE:
<223> OTHER INFORMATION: Synthetic DNA

<400> SEQUENCE: 12
atagatcttt acaggtccac cgcctggacc tc                          32

<210> SEQ ID NO 13
<211> LENGTH: 49
<212> TYPE: DNA
<213> ORGANISM: Artificial Sequence
<220> FEATURE:
<223> OTHER INFORMATION: Synthetic DNA

<400> SEQUENCE: 13
actacttggt acactgacgc gagcacgcag gagctcattc cagtgcgca        49

<210> SEQ ID NO 14
<211> LENGTH: 38
<212> TYPE: DNA
<213> ORGANISM: Artificial Sequence
<220> FEATURE:
<223> OTHER INFORMATION: Synthetic DNA

<400> SEQUENCE: 14
atatcatatg cgtcttctcc tcttccggca acggaact                    38

<210> SEQ ID NO 15
<211> LENGTH: 41
<212> TYPE: DNA
<213> ORGANISM: Artificial Sequence
<220> FEATURE:
<223> OTHER INFORMATION: Synthetic DNA

<400> SEQUENCE: 15
atatagatct ttattaggcg ccagggcaca ggaccacccc t                41

<210> SEQ ID NO 16
<211> LENGTH: 38
<212> TYPE: DNA
<213> ORGANISM: Artificial Sequence
<220> FEATURE:
<223> OTHER INFORMATION: Synthetic DNA

<400> SEQUENCE: 16
atatcatatg gaaatcgcgc tagagaggat ctacggcc                    38

<210> SEQ ID NO 17

-continued

```
<211> LENGTH: 41
<212> TYPE: DNA
<213> ORGANISM: Artificial Sequence
<220> FEATURE:
<223> OTHER INFORMATION: Synthetic DNA

<400> SEQUENCE: 17
atatagatct ttattagagg tcggcgaaga ggtagagcac c            41

<210> SEQ ID NO 18
<211> LENGTH: 41
<212> TYPE: DNA
<213> ORGANISM: Artificial Sequence
<220> FEATURE:
<223> OTHER INFORMATION: Synthetic DNA

<400> SEQUENCE: 18
agatcttgac ggggaaaycc gaattcggcg aacgtggcga g            41

<210> SEQ ID NO 19
<211> LENGTH: 45
<212> TYPE: DNA
<213> ORGANISM: Artificial sequence
<220> FEATURE:
<223> OTHER INFORMATION: Synthetic DNA
<220> FEATURE:
<221> NAME/KEY: misc_feature
<222> LOCATION: (26)..(26)
<223> OTHER INFORMATION: n is a, c, g, or t

<400> SEQUENCE: 19
ttctcgccac gttcgccgaa ttcggntttc cccgtcaaga tctaa         45

<210> SEQ ID NO 20
<211> LENGTH: 485
<212> TYPE: PRT
<213> ORGANISM: Homo sapiens

<400> SEQUENCE: 20
```

Cys Asp Gly Leu Ala Arg Gln Pro Glu Glu Val Val Leu Gln Ala Ser
1               5                   10                  15

Val Ser Ser Tyr His Leu Phe Arg Asp Val Ala Glu Val Thr Ala Phe
            20                  25                  30

Arg Gly Ser Leu Leu Ser Trp Tyr Asp Gln Glu Lys Arg Asp Leu Pro
        35                  40                  45

Trp Arg Arg Arg Ala Glu Asp Glu Met Asp Leu Asp Arg Arg Ala Tyr
    50                  55                  60

Ala Val Trp Val Ser Glu Val Met Leu Gln Gln Thr Gln Val Ala Thr
65                  70                  75                  80

Val Ile Asn Tyr Tyr Thr Gly Trp Met Gln Lys Trp Pro Thr Leu Gln
                85                  90                  95

Asp Leu Ala Ser Ala Ser Leu Glu Glu Val Asn Gln Leu Trp Ala Gly
            100                 105                 110

Leu Gly Tyr Tyr Ser Arg Gly Arg Arg Leu Gln Glu Gly Ala Arg Lys
        115                 120                 125

Val Val Glu Glu Leu Gly Gly His Met Pro Arg Thr Ala Glu Thr Leu
    130                 135                 140

Gln Gln Leu Leu Pro Gly Val Gly Arg Tyr Thr Ala Gly Ala Ile Ala
145                 150                 155                 160

Ser Ile Ala Phe Gly Gln Ala Thr Gly Val Val Asp Gly Asn Val Ala
                165                 170                 175

-continued

```
Arg Val Leu Cys Arg Val Arg Ala Ile Gly Ala Asp Pro Ser Ser Thr
            180                 185                 190

Leu Val Ser Gln Gln Leu Trp Gly Leu Ala Gln Gln Leu Val Asp Pro
            195                 200                 205

Ala Arg Pro Gly Asp Phe Asn Gln Ala Ala Met Glu Leu Gly Ala Thr
            210                 215                 220

Val Cys Thr Pro Gln Arg Pro Leu Cys Ser Gln Cys Pro Val Glu Ser
225                 230                 235                 240

Leu Cys Arg Ala Arg Gln Arg Val Glu Gln Glu Gln Leu Leu Ala Ser
            245                 250                 255

Gly Ser Leu Ser Gly Ser Pro Asp Val Glu Glu Cys Ala Pro Asn Thr
            260                 265                 270

Gly Gln Cys His Leu Cys Leu Pro Pro Ser Glu Pro Trp Asp Gln Thr
            275                 280                 285

Leu Gly Val Val Asn Phe Pro Arg Lys Ala Ser Arg Lys Pro Pro Arg
            290                 295                 300

Glu Glu Ser Ser Ala Thr Cys Val Leu Glu Gln Pro Gly Ala Leu Gly
305                 310                 315                 320

Ala Gln Ile Leu Leu Val Gln Arg Pro Asn Ser Gly Leu Leu Ala Gly
            325                 330                 335

Leu Trp Glu Phe Pro Ser Val Thr Trp Glu Pro Ser Glu Gln Leu Gln
            340                 345                 350

Arg Lys Ala Leu Leu Gln Glu Leu Gln Arg Trp Ala Gly Pro Leu Pro
            355                 360                 365

Ala Thr His Leu Arg His Leu Gly Glu Val Val His Thr Phe Ser His
            370                 375                 380

Ile Lys Leu Thr Tyr Gln Val Tyr Gly Leu Ala Leu Glu Gly Gln Thr
385                 390                 395                 400

Pro Val Thr Thr Val Pro Pro Gly Ala Arg Trp Leu Thr Gln Glu Glu
            405                 410                 415

Phe His Thr Ala Ala Val Ser Thr Ala Met Lys Lys Val Phe Arg Val
            420                 425                 430

Tyr Gln Gly Gln Gln Pro Gly Thr Cys Met Gly Ser Lys Arg Ser Gln
            435                 440                 445

Val Ser Ser Pro Cys Ser Arg Lys Lys Pro Arg Met Gly Gln Gln Val
450                 455                 460

Leu Asp Asn Phe Phe Arg Ser His Ile Ser Thr Asp Ala His Ser Leu
465                 470                 475                 480

Asn Ser Ala Ala Gln
            485
```

<210> SEQ ID NO 21
<211> LENGTH: 461
<212> TYPE: PRT
<213> ORGANISM: Schizosaccharomyces pombe

<400> SEQUENCE: 21

```
Met Ser Asp Ser Asn His Phe Leu Asp Leu His Ser Tyr Thr Gln Leu
1               5                   10                  15

Glu Val Glu Arg Phe Arg Glu Ser Leu Ile Gln Phe Tyr Asp Lys Thr
            20                  25                  30

Lys Arg Ile Leu Pro Trp Arg Lys Lys Glu Cys Ile Pro Pro Ser Glu
        35                  40                  45

Asp Ser Pro Leu Glu Asp Trp Glu Gln Pro Val Gln Arg Leu Tyr Glu
    50                  55                  60
```

```
Val Leu Val Ser Glu Ile Met Leu Gln Gln Thr Arg Val Glu Thr Val
 65                  70                  75                  80

Lys Arg Tyr Tyr Thr Lys Trp Met Glu Thr Leu Pro Thr Leu Lys Ser
                 85                  90                  95

Cys Ala Glu Ala Glu Tyr Asn Thr Gln Val Met Pro Leu Trp Ser Gly
            100                 105                 110

Met Gly Phe Tyr Thr Arg Cys Lys Arg Leu His Gln Ala Cys Gln His
            115                 120                 125

Leu Ala Lys Leu His Pro Ser Glu Ile Pro Arg Thr Gly Asp Glu Trp
130                 135                 140

Ala Lys Gly Ile Pro Gly Val Gly Pro Tyr Thr Ala Gly Ala Val Leu
145                 150                 155                 160

Ser Ile Ala Trp Lys Gln Pro Thr Gly Ile Val Asp Gly Asn Val Ile
                165                 170                 175

Arg Val Leu Ser Arg Ala Leu Ala Ile His Ser Asp Cys Ser Lys Gly
            180                 185                 190

Lys Ala Asn Ala Leu Ile Trp Lys Leu Ala Asn Glu Leu Val Asp Pro
            195                 200                 205

Val Arg Pro Gly Asp Glu Asn Gln Ala Leu Met Glu Leu Gly Ala Ile
            210                 215                 220

Thr Cys Thr Pro Gln Ser Pro Arg Cys Ser Val Cys Pro Ile Ser Glu
225                 230                 235                 240

Ile Cys Lys Ala Tyr Gln Glu Gln Asn Val Ile Arg Asp Gly Asn Thr
                245                 250                 255

Ile Lys Tyr Asp Ile Glu Asp Val Pro Cys Asn Ile Cys Ile Thr Asp
            260                 265                 270

Ile Pro Ser Lys Glu Asp Leu Gln Asn Trp Val Val Ala Arg Tyr Pro
            275                 280                 285

Val His Pro Ala Lys Thr Lys Gln Arg Glu Glu Arg Ala Leu Val Val
290                 295                 300

Ile Phe Gln Lys Thr Asp Pro Ser Thr Lys Glu Lys Phe Phe Leu Ile
305                 310                 315                 320

Arg Lys Arg Pro Ser Ala Gly Leu Leu Ala Gly Leu Trp Asp Phe Pro
                325                 330                 335

Thr Ile Glu Phe Gly Gln Glu Ser Trp Pro Lys Asp Met Asp Ala Glu
            340                 345                 350

Phe Gln Lys Ser Ile Ala Gln Trp Ile Ser Asn Asp Ser Arg Ser Leu
            355                 360                 365

Ile Lys Lys Tyr Gln Ser Arg Gly Arg Tyr Leu His Ile Phe Ser His
370                 375                 380

Ile Arg Lys Thr Ser His Val Phe Tyr Ala Ile Ala Ser Pro Asp Ile
385                 390                 395                 400

Val Thr Asn Glu Asp Phe Phe Trp Ile Ser Gln Ser Asp Leu Glu His
                405                 410                 415

Val Gly Met Cys Glu Leu Gly Leu Lys Asn Tyr Arg Ala Ala Leu Glu
            420                 425                 430

Ile Lys Lys Arg Lys Val Thr Ser Leu Ser Asn Phe Lys Glu Pro Lys
            435                 440                 445

Leu Thr Ser Ala Arg Arg Ile Val Thr Lys Ala Glu Cys
450                 455                 460

<210> SEQ ID NO 22
<211> LENGTH: 350
```

<212> TYPE: PRT
<213> ORGANISM: Escherichia coli

<400> SEQUENCE: 22

```
Met Gln Ala Ser Gln Phe Ser Ala Gln Val Leu Asp Trp Tyr Asp Lys
1               5                   10                  15

Tyr Gly Arg Lys Thr Leu Pro Trp Gln Ile Asp Lys Thr Pro Tyr Lys
            20                  25                  30

Val Trp Leu Ser Glu Val Met Leu Gln Gln Thr Gln Val Ala Thr Val
        35                  40                  45

Ile Pro Tyr Phe Glu Arg Phe Met Ala Arg Phe Pro Thr Val Thr Asp
50                  55                  60

Leu Ala Asn Ala Pro Leu Asp Glu Val Leu His Leu Trp Thr Gly Leu
65                  70                  75                  80

Gly Tyr Tyr Ala Arg Ala Arg Asn Leu His Lys Ala Ala Gln Gln Val
                85                  90                  95

Ala Thr Leu His Gly Gly Lys Phe Pro Glu Thr Phe Glu Glu Val Ala
            100                 105                 110

Ala Leu Pro Gly Val Gly Arg Ser Thr Ala Gly Ala Ile Leu Ser Leu
        115                 120                 125

Ser Leu Gly Lys His Phe Pro Ile Leu Asp Gly Asn Val Lys Arg Val
130                 135                 140

Leu Ala Arg Cys Tyr Ala Val Ser Gly Trp Pro Gly Lys Lys Glu Val
145                 150                 155                 160

Glu Asn Lys Leu Trp Ser Leu Ser Glu Gln Val Thr Pro Ala Val Gly
                165                 170                 175

Val Glu Arg Phe Asn Gln Ala Met Met Asp Leu Gly Ala Met Ile Cys
            180                 185                 190

Thr Arg Ser Lys Pro Lys Cys Ser Leu Cys Pro Leu Gln Asn Gly Cys
        195                 200                 205

Ile Ala Ala Asn Asn Ser Trp Ala Leu Tyr Pro Gly Lys Lys Pro
210                 215                 220

Lys Gln Thr Leu Pro Glu Arg Thr Gly Tyr Phe Leu Leu Leu Gln His
225                 230                 235                 240

Glu Asp Glu Val Leu Leu Ala Gln Arg Pro Pro Ser Gly Leu Trp Gly
                245                 250                 255

Gly Leu Tyr Cys Phe Pro Gln Phe Ala Asp Glu Glu Ser Leu Arg Gln
            260                 265                 270

Trp Leu Ala Gln Arg Gln Ile Ala Ala Asp Asn Leu Thr Gln Leu Thr
        275                 280                 285

Ala Phe Arg His Thr Phe Ser His Phe His Leu Asp Ile Val Pro Met
290                 295                 300

Trp Leu Pro Val Ser Ser Phe Thr Gly Cys Met Asp Glu Gly Asn Ala
305                 310                 315                 320

Leu Trp Tyr Asn Leu Ala Gln Pro Pro Ser Val Gly Leu Ala Ala Pro
                325                 330                 335

Val Glu Arg Leu Leu Gln Gln Leu Arg Thr Gly Ala Pro Val
            340                 345                 350
```

<210> SEQ ID NO 23
<211> LENGTH: 211
<212> TYPE: PRT
<213> ORGANISM: Escherichia coli

<400> SEQUENCE: 23

```
Met Asn Lys Ala Lys Arg Leu Glu Ile Leu Thr Arg Leu Arg Glu Asn
1               5                   10                  15

Asn Pro His Pro Thr Thr Glu Leu Asn Phe Ser Ser Pro Phe Glu Leu
                20                  25                  30

Leu Ile Ala Val Leu Leu Ser Ala Gln Ala Thr Asp Val Ser Val Asn
            35                  40                  45

Lys Ala Thr Ala Lys Leu Tyr Pro Val Ala Asn Thr Pro Ala Ala Met
50                  55                  60

Leu Glu Leu Gly Val Glu Gly Val Lys Thr Tyr Ile Lys Thr Ile Gly
65                  70                  75                  80

Leu Tyr Asn Ser Lys Ala Glu Asn Ile Ile Lys Thr Cys Arg Ile Leu
                85                  90                  95

Leu Glu Gln His Asn Gly Glu Val Pro Glu Asp Arg Ala Ala Leu Glu
            100                 105                 110

Ala Leu Pro Gly Val Gly Arg Lys Thr Ala Asn Val Val Leu Asn Thr
        115                 120                 125

Ala Phe Gly Trp Pro Thr Ile Ala Val Asp Thr His Ile Phe Arg Val
130                 135                 140

Cys Asn Arg Thr Gln Phe Ala Pro Gly Lys Asn Val Glu Gln Val Glu
145                 150                 155                 160

Glu Lys Leu Leu Lys Val Val Pro Ala Glu Phe Lys Val Asp Cys His
                165                 170                 175

His Trp Leu Ile Leu His Gly Arg Tyr Thr Cys Ile Ala Arg Lys Pro
            180                 185                 190

Arg Cys Gly Ser Cys Ile Ile Glu Asp Leu Cys Glu Tyr Lys Glu Lys
        195                 200                 205

Val Asp Ile
    210

<210> SEQ ID NO 24
<211> LENGTH: 28
<212> TYPE: PRT
<213> ORGANISM: Thermus thermophilus

<400> SEQUENCE: 24

Lys Arg Ile Arg Val His Gly Asp Tyr Asp Ala Asp Gly Leu Thr Gly
1               5                   10                  15

Thr Ala Ile Leu Val Arg Gly Leu Ala Ala Leu Gly
            20                  25

<210> SEQ ID NO 25
<211> LENGTH: 28
<212> TYPE: PRT
<213> ORGANISM: escherichia coli

<400> SEQUENCE: 25

Thr Arg Ile Ile Val Val Gly Asp Phe Asp Ala Asp Gly Ala Thr Ser
1               5                   10                  15

Thr Ala Leu Ser Val Leu Ala Met Arg Ser Leu Gly
            20                  25

<210> SEQ ID NO 26
<211> LENGTH: 28
<212> TYPE: PRT
<213> ORGANISM: aquifex aeolicus

<400> SEQUENCE: 26

Lys Arg Ile Ile Ile Tyr Gly Asp Tyr Asp Val Asp Gly Ile Thr Gly
```

```
                 1               5                  10                 15
Thr Ala Ile Leu Tyr Arg Val Leu Lys Leu Leu Gly
                20                  25

<210> SEQ ID NO 27
<211> LENGTH: 28
<212> TYPE: PRT
<213> ORGANISM: helicobacter pylori

<400> SEQUENCE: 27

Thr Glu Ile Leu Val Val Gly Asp Tyr Asp Ala Asp Gly Val Ile Ser
1               5                  10                 15

Ser Ala Ile Met Ala Lys Phe Phe Glu Ser Leu Asn
                20                  25

<210> SEQ ID NO 28
<211> LENGTH: 28
<212> TYPE: PRT
<213> ORGANISM: Haemophilus influenzae

<400> SEQUENCE: 28

Gln Lys Ile Val Ile Val Gly Asp Phe Asp Ala Asp Gly Ala Thr Ser
1               5                  10                 15

Thr Ala Leu Ser Val Leu Ala Leu Arg Gln Leu Gly
                20                  25

<210> SEQ ID NO 29
<211> LENGTH: 28
<212> TYPE: PRT
<213> ORGANISM: saccharomyces cerevisiae

<400> SEQUENCE: 29

Thr Ile Cys Val Gly Asn Glu Ser Ala Asp Met Asp Ser Ile Ala Ser
1               5                  10                 15

Ala Ile Thr Tyr Ser Tyr Cys Gln Tyr Ile Tyr Asn
                20                  25

<210> SEQ ID NO 30
<211> LENGTH: 28
<212> TYPE: PRT
<213> ORGANISM: drosophila melanogaster

<400> SEQUENCE: 30

His Leu Val Met Gly Asn Glu Ser Cys Asp Leu Asp Ser Ala Val Ser
1               5                  10                 15

Ala Val Thr Leu Ala Phe Val Tyr Ala Ala Ser Ser
                20                  25

<210> SEQ ID NO 31
<211> LENGTH: 19
<212> TYPE: PRT
<213> ORGANISM: thermus thermophilus

<400> SEQUENCE: 31

Ser Asp Leu Phe Leu Thr Val Asp Cys Gly Ile Thr Asn His Ala Glu
1               5                  10                 15

Leu Arg Glu

<210> SEQ ID NO 32
<211> LENGTH: 19
<212> TYPE: PRT
<213> ORGANISM: escherichia coli
```

-continued

```
<400> SEQUENCE: 32

Ala Gln Leu Ile Val Thr Val Asp Asn Gly Ile Ser Ser His Ala Gly
1               5                   10                  15

Val Glu His

<210> SEQ ID NO 33
<211> LENGTH: 19
<212> TYPE: PRT
<213> ORGANISM: aquifex aeolicus

<400> SEQUENCE: 33

Gly Asp Phe Leu Ile Thr Val Asp Asn Gly Thr Ser Ala Val Glu Glu
1               5                   10                  15

Ile Asp Gln

<210> SEQ ID NO 34
<211> LENGTH: 19
<212> TYPE: PRT
<213> ORGANISM: helicobacter pylori

<400> SEQUENCE: 34

Ala Pro Leu Ile Ile Thr Val Asp Asn Gly Ile Asn Ala Phe Glu Ala
1               5                   10                  15

Ala Arg Phe

<210> SEQ ID NO 35
<211> LENGTH: 19
<212> TYPE: PRT
<213> ORGANISM: haemophilus influenzae

<400> SEQUENCE: 35

Val Gln Leu Leu Met Thr Val Asp Asn Gly Val Ser Ser Phe Asp Gly
1               5                   10                  15

Val Ala Phe

<210> SEQ ID NO 36
<211> LENGTH: 19
<212> TYPE: PRT
<213> ORGANISM: saccharomyces cerevisiae

<400> SEQUENCE: 36

Glu Leu Asn Ser Tyr Leu Val Asp Asn Asp Thr Pro Lys Asn Leu
1               5                   10                  15

Lys Asn Tyr

<210> SEQ ID NO 37
<211> LENGTH: 19
<212> TYPE: PRT
<213> ORGANISM: drosophila melanogaster

<400> SEQUENCE: 37

Pro Leu Val Cys Glu Met Trp Asp Cys Arg Ala Arg Val Ala Leu Pro
1               5                   10                  15

Arg Arg Tyr

<210> SEQ ID NO 38
<211> LENGTH: 13
<212> TYPE: PRT
<213> ORGANISM: thermus thermophilus
```

```
<400> SEQUENCE: 38

Val Glu Val Ile Val Thr Asp His His Thr Pro Gly Lys
1               5                   10

<210> SEQ ID NO 39
<211> LENGTH: 13
<212> TYPE: PRT
<213> ORGANISM: escherichia coli

<400> SEQUENCE: 39

Ile Pro Val Ile Val Thr Asp His His Leu Pro Gly Asp
1               5                   10

<210> SEQ ID NO 40
<211> LENGTH: 13
<212> TYPE: PRT
<213> ORGANISM: aquifex aeolicus

<400> SEQUENCE: 40

Leu Glu Thr Val Val Ile Asp His His Asn Val Pro Pro
1               5                   10

<210> SEQ ID NO 41
<211> LENGTH: 13
<212> TYPE: PRT
<213> ORGANISM: helicobacter pylori

<400> SEQUENCE: 41

Tyr Thr Leu Ile Ile Thr Asp His His Cys Leu His His
1               5                   10

<210> SEQ ID NO 42
<211> LENGTH: 13
<212> TYPE: PRT
<213> ORGANISM: haemophilus influenzae

<400> SEQUENCE: 42

Ile Arg Val Leu Val Thr Asp His His Leu Pro Pro Glu
1               5                   10

<210> SEQ ID NO 43
<211> LENGTH: 13
<212> TYPE: PRT
<213> ORGANISM: saccharomyces cerevisiae

<400> SEQUENCE: 43

Asn Val Val Gly Ile Ile Asp His His Phe Asp Leu Gln
1               5                   10

<210> SEQ ID NO 44
<211> LENGTH: 13
<212> TYPE: PRT
<213> ORGANISM: drosophila melanogaster

<400> SEQUENCE: 44

Asn Val Ile Glu Ile Leu Asp His Arg Pro Leu Glu Asp
1               5                   10

<210> SEQ ID NO 45
<211> LENGTH: 19
<212> TYPE: PRT
<213> ORGANISM: thermus thermophilus

<400> SEQUENCE: 45
```

```
Tyr Ala Asp Leu Ala Ala Val Gly Thr Ile Ala Asp Val Ala Pro Leu
1               5                   10                  15
Trp Gly Trp

<210> SEQ ID NO 46
<211> LENGTH: 19
<212> TYPE: PRT
<213> ORGANISM: escherichia coli

<400> SEQUENCE: 46

Leu Leu Asp Leu Val Ala Leu Gly Thr Val Ala Asp Val Val Pro Leu
1               5                   10                  15
Asp Ala Asn

<210> SEQ ID NO 47
<211> LENGTH: 19
<212> TYPE: PRT
<213> ORGANISM: aquifex aeolicus

<400> SEQUENCE: 47

Phe Leu Asp Leu Val Ala Leu Gly Leu Leu Ala Asp Tyr Met Pro Val
1               5                   10                  15

Asn Pro Val

<210> SEQ ID NO 48
<211> LENGTH: 19
<212> TYPE: PRT
<213> ORGANISM: helicobacter pylori

<400> SEQUENCE: 48

Leu Leu Cys Leu Ala Gly Val Ala Thr Ile Ala Asp Met Met Pro Leu
1               5                   10                  15

Thr Phe Phe

<210> SEQ ID NO 49
<211> LENGTH: 19
<212> TYPE: PRT
<213> ORGANISM: haemophilus influenzae

<400> SEQUENCE: 49

Leu Leu Asp Leu Val Ala Leu Gly Thr Ile Ala Asp Val Val Pro Leu
1               5                   10                  15

Asp Gln Asn

<210> SEQ ID NO 50
<211> LENGTH: 19
<212> TYPE: PRT
<213> ORGANISM: saccharomyces cerevisiae

<400> SEQUENCE: 50

Ile Ala Leu Leu Leu Met Gly Ala Ile Leu Ile Asp Thr Ser Asn Met
1               5                   10                  15

Arg Arg Lys

<210> SEQ ID NO 51
<211> LENGTH: 19
<212> TYPE: PRT
<213> ORGANISM: drosophila melanogaster

<400> SEQUENCE: 51

Val Ala Gln Leu Leu His Ala Thr Ile Val Leu Asp Thr Ile Asn Phe
1               5                   10                  15
```

Ala Pro Ala

<210> SEQ ID NO 52
<211> LENGTH: 17
<212> TYPE: PRT
<213> ORGANISM: thermus thermophilus

<400> SEQUENCE: 52

Asp Leu Leu Leu Arg Tyr Gly Gly His Lys Glu Ala Ala Gly Phe Ala
1               5                   10                  15
Met

<210> SEQ ID NO 53
<211> LENGTH: 17
<212> TYPE: PRT
<213> ORGANISM: escherichia coli

<400> SEQUENCE: 53

Gly Met Met Leu Lys Phe Gly Gly His Ala Met Ala Ala Gly Leu Ser
1               5                   10                  15
Leu

<210> SEQ ID NO 54
<211> LENGTH: 17
<212> TYPE: PRT
<213> ORGANISM: aquifex aeolicus

<400> SEQUENCE: 54

Asp Met Phe Leu Lys Trp Gly Gly His Asp Lys Ala Met Gly Leu Thr
1               5                   10                  15
Leu

<210> SEQ ID NO 55
<211> LENGTH: 17
<212> TYPE: PRT
<213> ORGANISM: helicobacter pylori

<400> SEQUENCE: 55

Ser Leu Leu Leu Gly Tyr Gly Gly His Arg Gln Ala Cys Gly Leu Ser
1               5                   10                  15
Val

<210> SEQ ID NO 56
<211> LENGTH: 17
<212> TYPE: PRT
<213> ORGANISM: haemophilus influenzae

<400> SEQUENCE: 56

Asn Met Ile Leu Lys Phe Gly Gly His Ala Met Ala Ala Gly Leu Ser
1               5                   10                  15
Ile

<210> SEQ ID NO 57
<211> LENGTH: 49
<212> TYPE: DNA
<213> ORGANISM: Artificial sequence
<220> FEATURE:
<223> OTHER INFORMATION: Synthetic DNA

<400> SEQUENCE: 57
actacttggt acactgacgc gagcacgcag gagctcattc cagtgcgca          49

```
<210> SEQ ID NO 58
<211> LENGTH: 343
<212> TYPE: PRT
<213> ORGANISM: Thermus thermophilus

<400> SEQUENCE: 58

Met Arg Leu Leu Leu Phe Arg Gln Arg Asn Phe Arg Asn Leu Ala Leu
1               5                   10                  15

Glu Ala Tyr Arg Pro Pro Gly Leu Ser Ala Leu Val Gly Ala Asn
            20                  25                  30

Ala Gln Gly Lys Thr Ser Leu Leu Leu Gly Ile His Leu Ala Leu Gly
        35                  40                  45

Gly Glu Val Pro Leu Gly Leu Ala Asp Leu Val Arg Phe Gly Glu Glu
    50                  55                  60

Glu Ala Trp Leu His Ala Glu Val Glu Thr Glu Leu Gly Ala Tyr Arg
65                  70                  75                  80

Leu Glu His Arg Leu Gly Pro Gly Gly Arg Glu Val Leu Leu Asn Gly
                85                  90                  95

Lys Arg Val Ser Leu Arg Thr Leu Trp Glu Leu Pro Gly Ser Val Leu
            100                 105                 110

Val Ser Pro Leu Asp Leu Glu Ala Val Leu Gly Pro Lys Glu Glu Arg
        115                 120                 125

Arg Ala Tyr Leu Asp Arg Leu Ile Ala His Phe Ser Arg Arg Tyr Ala
130                 135                 140

Ala Leu Leu Ser Ala Tyr Glu Lys Ala Leu Arg Gln Arg Asn Ala Leu
145                 150                 155                 160

Leu Lys Ala Gly Gly Glu Gly Leu Ser Ala Trp Asp Arg Glu Leu Ala
                165                 170                 175

Arg Tyr Gly Asp Glu Ile Val Ala Leu Arg Arg Phe Leu Arg Arg
            180                 185                 190

Phe Ala Pro Ile Leu Arg Glu Val His Ala Ala Leu Ala Ala Lys Glu
            195                 200                 205

Ala Gly Leu Arg Leu Glu Glu Thr Ala Gly Glu Gly Val Leu Arg Ala
210                 215                 220

Leu Glu Ala Ser Arg Ala Glu Glu Arg Glu Arg Gly Gln Thr Leu Val
225                 230                 235                 240

Gly Pro His Arg Asp Asp Leu Val Phe Leu Leu Glu Gly Arg Pro Ala
                245                 250                 255

His Arg Phe Ala Ser Arg Gly Glu Ala Lys Thr Leu Ala Leu Ala Leu
            260                 265                 270

Arg Leu Ala Glu His Arg Leu Leu Gly Glu His His Gly Glu Pro Pro
275                 280                 285

Leu Leu Leu Val Asp Glu Trp Gly Glu Glu Leu Asp Glu Ala Arg Arg
290                 295                 300

Arg Ala Val Leu Ala Tyr Ala Gln Ala Leu Pro Gln Ala Ile Leu Ala
305                 310                 315                 320

Gly Leu Glu Ala Pro Pro Gly Val Pro Val Cys Ser Val Val Arg Gly
                325                 330                 335

Val Val Leu Cys Pro Gly Ala
            340

<210> SEQ ID NO 59
<211> LENGTH: 357
<212> TYPE: PRT
<213> ORGANISM: Escherichia coli
```

<400> SEQUENCE: 59

```
Met Ser Leu Thr Arg Leu Leu Ile Arg Asp Phe Arg Asn Ile Glu Thr
1               5                   10                  15

Ala Asp Leu Ala Leu Ser Pro Gly Phe Asn Phe Leu Val Gly Ala Asn
            20                  25                  30

Gly Ser Gly Lys Thr Ser Val Leu Glu Ala Ile Tyr Thr Leu Gly His
        35                  40                  45

Gly Arg Ala Phe Arg Ser Leu Gln Ile Gly Arg Val Ile Arg His Glu
    50                  55                  60

Gln Glu Ala Phe Val Leu His Gly Arg Leu Gln Gly Glu Glu Arg Glu
65                  70                  75                  80

Thr Ala Ile Gly Leu Thr Lys Asp Lys Gln Gly Asp Ser Lys Val Arg
                85                  90                  95

Ile Asp Gly Thr Asp Gly His Lys Val Ala Glu Leu Ala His Leu Met
            100                 105                 110

Pro Met Gln Leu Ile Thr Pro Glu Gly Phe Thr Leu Leu Asn Gly Gly
        115                 120                 125

Pro Lys Tyr Arg Arg Ala Phe Leu Asp Trp Gly Cys Phe His Asn Glu
    130                 135                 140

Pro Gly Phe Phe Thr Ala Trp Ser Asn Leu Lys Arg Leu Leu Lys Gln
145                 150                 155                 160

Arg Asn Ala Ala Leu Arg Gln Val Thr Arg Tyr Glu Gln Leu Arg Pro
                165                 170                 175

Trp Asp Lys Glu Leu Ile Pro Leu Ala Glu Gln Ile Ser Thr Trp Arg
            180                 185                 190

Ala Glu Tyr Ser Ala Gly Ile Ala Ala Asp Met Ala Asp Thr Cys Lys
        195                 200                 205

Gln Phe Leu Pro Glu Phe Ser Leu Thr Phe Ser Phe Gln Arg Gly Trp
    210                 215                 220

Glu Lys Glu Thr Glu Tyr Ala Glu Val Leu Glu Arg Asn Phe Glu Arg
225                 230                 235                 240

Asp Arg Gln Leu Thr Tyr Thr Ala His Gly Pro His Lys Ala Asp Leu
                245                 250                 255

Arg Ile Arg Ala Asp Gly Ala Pro Val Glu Asp Thr Leu Ser Arg Gly
            260                 265                 270

Gln Leu Lys Leu Leu Met Cys Ala Leu Arg Leu Ala Gln Gly Glu Phe
        275                 280                 285

Leu Thr Arg Glu Ser Gly Arg Arg Cys Leu Tyr Leu Ile Asp Asp Phe
    290                 295                 300

Ala Ser Glu Leu Asp Asp Glu Arg Arg Gly Leu Leu Ala Ser Arg Leu
305                 310                 315                 320

Lys Ala Thr Gln Ser Gln Val Phe Val Ser Ala Ile Ser Ala Glu His
                325                 330                 335

Val Ile Asp Met Ser Asp Glu Asn Ser Lys Met Phe Thr Val Glu Lys
            340                 345                 350

Gly Lys Ile Thr Asp
        355
```

<210> SEQ ID NO 60
<211> LENGTH: 233
<212> TYPE: PRT
<213> ORGANISM: Pseudomonas putida

<400> SEQUENCE: 60

```
Met Ser Leu Arg Arg Ile Met Val Thr Ala Val Arg Asn Leu His Pro
 1               5                  10                 15

Val Thr Leu Leu Pro Ser Pro Arg Ile Asn Ile Leu Tyr Gly Ala Asn
             20                  25                 30

Gly Ser Gly Lys Thr Ser Val Leu Glu Ala Val His Leu Leu Gly Leu
         35                  40                 45

Ala Arg Ser Phe Arg Ser Thr Arg Leu Asn Pro Val Ile Gln Tyr Glu
     50                  55                  60

Gln Ala Ala Cys Thr Val Phe Gly Val Gln Leu Thr Glu Gly Gly
65                  70                  75                  80

Thr Ser Asn Leu Gly Val Ser Arg Glu Arg Gln Gly Glu Phe Thr Ile
             85                  90                  95

Arg Ile Asp Ala Leu Lys Pro Val Phe Glu Arg Thr Leu Ser Glu Leu
             100                 105                110

Val Glu Leu Asp Gly Leu Thr Leu Ser Tyr Tyr Arg Gly Trp Asp Lys
             115                 120                125

Asp Arg Glu Leu Gln Glu Val Leu Ala Ser Ser Leu Leu Arg Asp Gln
    130                 135                 140

Gln Met Gly His Thr Gln Ala Gly Pro Gln Arg Ala Asp Leu Arg Leu
145                 150                 155                 160

Arg Leu Ala Gly Asn Asn Ala Ala Asp Ile Leu Ser Arg Gly Gln Gln
                165                 170                 175

Lys Leu Val Val Cys Ala Leu Arg Ile Ala Gln Gly His Leu Val Ser
            180                 185                 190

Gln Ala Arg Arg Gly His Cys Ile Tyr Leu Val Asp Asp Leu Pro Ser
        195                 200                 205

Glu Leu Asp Asp Gln His Arg Arg Ala Leu Cys Arg Leu Leu Glu Glu
    210                 215                 220

Leu Arg Cys Gln Cys Ser Ser Pro Val
225                 230

<210> SEQ ID NO 61
<211> LENGTH: 370
<212> TYPE: PRT
<213> ORGANISM: Bacillus subtilis

<400> SEQUENCE: 61

Met Tyr Ile Gln Asn Leu Glu Leu Thr Ser Tyr Arg Asn Tyr Asp His
 1               5                  10                 15

Ala Glu Leu Gln Phe Glu Asn Lys Val Asn Val Ile Ile Gly Glu Asn
             20                  25                 30

Ala Gln Gly Lys Thr Asn Leu Met Glu Ala Ile Tyr Val Leu Ser Met
         35                  40                 45

Ala Lys Ser His Arg Thr Ser Asn Asp Lys Glu Leu Ile Arg Trp Asp
     50                  55                  60

Lys Asp Tyr Ala Lys Ile Glu Gly Arg Val Met Lys Gln Asn Gly Ala
65                  70                  75                  80

Ile Pro Met Gln Leu Val Ile Ser Lys Lys Gly Lys Lys Gly Lys Val
             85                  90                  95

Asn His Ile Glu Gln Gln Lys Leu Ser Gln Tyr Val Gly Ala Leu Asn
             100                 105                110

Thr Ile Met Phe Ala Pro Glu Asp Leu Asn Leu Val Lys Gly Ser Pro
             115                 120                125

Gln Val Arg Arg Arg Phe Leu Asp Met Glu Ile Gly Gln Val Ser Pro
```

-continued

```
            130                 135                 140
Val Tyr Leu His Asp Leu Ser Leu Tyr Gln Lys Ile Leu Ser Gln Arg
145                 150                 155                 160

Asn His Phe Leu Lys Gln Leu Gln Thr Arg Lys Gln Thr Asp Arg Thr
                165                 170                 175

Met Leu Asp Val Leu Thr Asp Gln Leu Val Glu Val Ala Ala Lys Val
            180                 185                 190

Val Val Lys Arg Leu Gln Phe Thr Ala Gln Leu Glu Lys Trp Ala Gln
        195                 200                 205

Pro Ile His Ala Gly Ile Ser Arg Gly Leu Glu Glu Leu Thr Leu Lys
    210                 215                 220

Tyr His Thr Ala Leu Asp Val Ser Asp Pro Leu Asp Leu Ser Lys Ile
225                 230                 235                 240

Gly Asp Ser Tyr Gln Glu Ala Phe Ser Lys Leu Arg Glu Lys Glu Ile
                245                 250                 255

Glu Arg Gly Val Thr Leu Ser Gly Pro His Arg Asp Asp Val Leu Phe
            260                 265                 270

Tyr Val Asn Gly Arg Asp Val Gln Thr Tyr Gly Ser Gln Gly Gln Gln
        275                 280                 285

Arg Thr Thr Ala Leu Ser Leu Lys Leu Ala Glu Ile Asp Leu Ile His
    290                 295                 300

Glu Glu Ile Gly Glu Tyr Pro Ile Leu Leu Leu Asp Asp Val Leu Ser
305                 310                 315                 320

Glu Leu Asp Asp Tyr Arg Gln Ser His Leu Leu His Thr Ile Gln Gly
                325                 330                 335

Arg Val Gln Thr Phe Val Thr Thr Thr Ser Val Asp Gly Ile Asp His
            340                 345                 350

Glu Thr Leu Arg Gln Ala Gly Met Phe Arg Val Gln Asn Gly Ala Leu
        355                 360                 365

Val Lys
    370

<210> SEQ ID NO 62
<211> LENGTH: 385
<212> TYPE: PRT
<213> ORGANISM: Mycobacterium tuberculosis

<400> SEQUENCE: 62

Met Tyr Val Arg His Leu Gly Leu Arg Asp Phe Arg Ser Trp Ala Cys
1               5                   10                  15

Val Asp Leu Glu Leu His Pro Gly Arg Thr Val Phe Val Gly Pro Asn
            20                  25                  30

Gly Tyr Gly Lys Thr Asn Leu Ile Glu Ala Leu Trp Tyr Ser Thr Thr
        35                  40                  45

Leu Gly Ser His Arg Val Ser Ala Asp Leu Pro Leu Ile Arg Val Gly
    50                  55                  60

Thr Asp Arg Ala Val Ile Ser Thr Ile Val Asn Asp Gly Arg Glu
65                  70                  75                  80

Cys Ala Val Asp Leu Glu Ile Ala Thr Gly Arg Val Asn Lys Ala Arg
                85                  90                  95

Leu Asn Arg Ser Ser Val Arg Ser Thr Arg Asp Val Val Gly Val Leu
            100                 105                 110

Arg Ala Val Leu Phe Ala Pro Glu Asp Leu Gly Leu Val Arg Gly Asp
        115                 120                 125
```

```
Pro Ala Asp Arg Arg Tyr Leu Asp Asp Leu Ala Ile Val Arg Arg
    130                 135                 140

Pro Ala Ile Ala Ala Val Arg Ala Glu Tyr Glu Arg Val Leu Arg Gln
145                 150                 155                 160

Arg Thr Ala Leu Leu Lys Ser Val Pro Gly Ala Arg Tyr Arg Gly Asp
                165                 170                 175

Arg Gly Val Phe Asp Thr Leu Asp Leu Trp Asp Ser Arg Leu Ala Glu
            180                 185                 190

His Gly Ala Glu Leu Val Ala Ala Arg Ile Asp Leu Val Asn Gln Leu
        195                 200                 205

Ala Pro Glu Val Lys Lys Ala Tyr Gln Leu Leu Ala Pro Glu Ser Arg
    210                 215                 220

Ser Ala Ser Ile Gly Tyr Arg Ala Ser Met Asp Val Thr Gly Pro Ser
225                 230                 235                 240

Glu Gln Ser Asp Ile Asp Arg Gln Leu Leu Ala Ala Arg Leu Leu Ala
                245                 250                 255

Ala Leu Ala Ala Arg Arg Asp Ala Glu Leu Glu Arg Gly Val Cys Leu
            260                 265                 270

Val Gly Pro His Arg Asp Asp Leu Ile Leu Arg Leu Gly Asp Gln Pro
        275                 280                 285

Ala Lys Gly Phe Ala Ser His Gly Glu Ala Trp Ser Leu Ala Val Ala
    290                 295                 300

Leu Arg Leu Ala Ala Tyr Gln Leu Leu Arg Val Asp Gly Gly Glu Pro
305                 310                 315                 320

Val Leu Leu Leu Asp Asp Val Phe Ala Glu Leu Asp Val Met Arg Arg
                325                 330                 335

Arg Ala Leu Ala Thr Ala Ala Glu Ser Ala Glu Gln Val Leu Val Thr
            340                 345                 350

Ala Ala Val Leu Glu Asp Ile Pro Ala Gly Trp Asp Ala Arg Arg Val
        355                 360                 365

His Ile Asp Val Arg Ala Asp Asp Thr Gly Ser Met Ser Val Val Leu
    370                 375                 380

Pro
385

<210> SEQ ID NO 63
<211> LENGTH: 359
<212> TYPE: PRT
<213> ORGANISM: Deinococcus radiodurans

<400> SEQUENCE: 63

Met Gly Asp Val Arg Leu Ser Ala Leu Ser Thr Leu Asn Tyr Arg Asn
1               5                   10                  15

Leu Ala Pro Gly Thr Leu Asn Phe Pro Glu Gly Val Thr Gly Ile Tyr
                20                  25                  30

Gly Glu Asn Gly Ala Gly Lys Thr Asn Leu Leu Glu Ala Ala Tyr Leu
            35                  40                  45

Ala Leu Thr Gly Gln Thr Asp Ala Pro Arg Ile Glu Gln Leu Ile Gln
        50                  55                  60

Ala Gly Glu Thr Glu Ala Tyr Val Arg Ala Asp Leu Gln Gln Gly Gly
65                  70                  75                  80

Ser Leu Ser Ile Gln Glu Val Gly Leu Gly Arg Gly Arg Gln Leu
                85                  90                  95

Lys Val Asp Gly Val Arg Ala Arg Thr Gly Asp Leu Pro Arg Gly Gly
            100                 105                 110
```

```
Ala Val Trp Ile Arg Pro Glu Asp Ser Glu Leu Val Phe Gly Pro Pro
        115                 120                 125

Ser Gly Arg Arg Ala Tyr Leu Asp Ser Leu Leu Ser Arg Leu Ser Ala
    130                 135                 140

Arg Tyr Gly Glu Gln Leu Ser Arg Tyr Glu Arg Thr Val Ser Gln Arg
145                 150                 155                 160

Asn Ala Ala Leu Arg Gly Gly Glu Glu Trp Ala Met His Val Trp Asp
                165                 170                 175

Asp Val Leu Leu Lys Leu Gly Thr Glu Ile Met Leu Phe Arg Arg Arg
            180                 185                 190

Ala Leu Thr Arg Leu Asp Glu Leu Ala Arg Glu Ala Asn Ala Gln Leu
        195                 200                 205

Gly Ser Arg Lys Thr Leu Ala Leu Thr Leu Thr Glu Ser Thr Ser Pro
    210                 215                 220

Glu Thr Tyr Ala Ala Asp Leu Arg Gly Arg Arg Ala Glu Glu Leu Ala
225                 230                 235                 240

Arg Gly Ser Thr Val Thr Gly Pro His Arg Asp Asp Leu Leu Leu Thr
                245                 250                 255

Leu Gly Asp Phe Pro Ala Ser Asp Tyr Ala Ser Arg Gly Glu Gly Arg
            260                 265                 270

Thr Val Ala Leu Ala Leu Arg Arg Ala Glu Leu Glu Leu Leu Arg Glu
        275                 280                 285

Lys Phe Gly Glu Asp Pro Val Leu Leu Leu Asp Asp Phe Thr Ala Glu
    290                 295                 300

Leu Asp Pro His Arg Arg Gln Tyr Leu Leu Asp Leu Ala Ala Ser Val
305                 310                 315                 320

Pro Gln Ala Ile Val Thr Gly Thr Glu Leu Ala Pro Gly Ala Ala Leu
                325                 330                 335

Thr Leu Arg Ala Gln Ala Gly Arg Phe Thr Pro Val Ala Asp Glu Glu
            340                 345                 350

Met Gln Ala Glu Gly Thr Ala
        355

<210> SEQ ID NO 64
<211> LENGTH: 89
<212> TYPE: PRT
<213> ORGANISM: Artificial sequence
<220> FEATURE:
<223> OTHER INFORMATION: UvrB-beta artificial fragment

<400> SEQUENCE: 64

Arg Asn Leu Val Val Glu Arg Gly Lys Pro Tyr Pro Arg Glu Val Leu
1               5                   10                  15

Leu Glu Arg Leu Leu Glu Leu Gly Tyr Gln Arg Asn Asp Ile Asp Leu
            20                  25                  30

Ser Pro Gly Arg Phe Arg Ala Lys Gly Glu Val Leu Glu Ile Phe Pro
        35                  40                  45

Ala Tyr Glu Thr Glu Pro Ile Arg Val Glu Leu Phe Gly Asp Glu Val
    50                  55                  60

Glu Arg Ile Ser Gln Val His Pro Val Thr Gly Glu Arg Leu Arg Glu
65                  70                  75                  80

Leu Pro Gly Phe Val Leu Phe Pro Ala
                85

<210> SEQ ID NO 65
```

-continued

```
<211> LENGTH: 87
<212> TYPE: PRT
<213> ORGANISM: Artificial sequence
<220> FEATURE:
<223> OTHER INFORMATION: TRCF-beta artificial fragment

<400> SEQUENCE: 65

Trp Arg Leu Leu Leu Glu Val Gly Arg Ala Tyr Pro Arg Glu Ala Leu
1               5                   10                  15

Leu Ser Arg Leu Leu Lys Leu Gly Tyr Ala Arg Asp Glu Asp Tyr Arg
            20                  25                  30

Val Leu Gly Glu Val Val Glu Leu Gly Glu Val Arg Leu Glu Phe Phe
        35                  40                  45

Gly Asp Glu Leu Glu Arg Leu Val Val Arg Gly Glu Glu Arg Arg Arg
    50                  55                  60

His Val Leu Leu Pro Lys Pro Gly Lys Ala Glu Gly Phe Thr Ser Lys
65                  70                  75                  80

Lys Val Leu His Glu Pro Gly
                85
```